US009827658B2

(12) United States Patent
Gregory et al.

(10) Patent No.: US 9,827,658 B2
(45) **Date of Patent: *Nov. 28, 2017**

(54) POWER TOOL HAVING LATCHED PUSHER ASSEMBLY

(71) Applicant: Black & Decker, Inc., Newark, DE (US)

(72) Inventors: Larry E. Gregory, Baltimore, MD (US); Michael P. Baron, Phoenix, MD (US); Lee M. Brendel, Bel Air, MD (US); Todd A. Hagan, Windsor, PA (US); Stuart E. Garber, Towson, MD (US)

(73) Assignee: Black & Decker Inc., Newark, DE (US)

( * ) Notice: Subject to any disclaimer, the term of this patent is extended or adjusted under 35 U.S.C. 154(b) by 982 days.

This patent is subject to a terminal disclaimer.

(21) Appl. No.: 13/986,732

(22) Filed: May 30, 2013

(65) Prior Publication Data

US 2013/0320066 A1 Dec. 5, 2013

Related U.S. Application Data

(63) Continuation-in-part of application No. 13/485,007, filed on May 31, 2012, now Pat. No. 9,643,305.

(51) Int. Cl.

| | |
|---|---|
| ***B25C 1/00*** | (2006.01) |
| ***B25C 5/16*** | (2006.01) |
| ***A61B 17/32*** | (2006.01) |

(52) U.S. Cl.

CPC .............. *B25C 1/001* (2013.01); *B25C 1/005* (2013.01); *B25C 5/162* (2013.01)

(58) Field of Classification Search

CPC .................................. B25C 1/00; B25C 1/008

(Continued)

(56) References Cited

U.S. PATENT DOCUMENTS

| | | | |
|---|---|---|---|
| 618,085 | A | 1/1899 | Grandy |
| 2,522,931 | A | 9/1950 | Curtiss |

(Continued)

FOREIGN PATENT DOCUMENTS

| | | | |
|---|---|---|---|
| EP | 0387211 | A2 | 12/1990 |
| EP | 0927605 | A2 | 7/1999 |

(Continued)

OTHER PUBLICATIONS

European Search Report for EP 13170119.5, EPO (dated Apr. 29, 2016).

(Continued)

*Primary Examiner* — Andrew M Tecco
*Assistant Examiner* — Praachi M Pathak
(74) *Attorney, Agent, or Firm* — Wright IP & International Law; Eric G. Wright

(57) ABSTRACT

A magazine for use with a fastening tool. The magazine can have a pusher assembly that can be retracted into a recess in the magazine to facilitate loading and reloading of fasteners. The pusher assembly can have a pusher assembly knob which can be reversibly latched to a detent to maintain the pusher assembly in a retracted state. The fastening tool can use a magazine which can be reloaded by a method which has a step of reversibly retracting the pusher assembly into the retracted state to allow for feeding one or more fasteners to the magazine.

17 Claims, 41 Drawing Sheets

(58) Field of Classification Search
USPC .................................. 227/126, 125, 120, 130
See application file for complete search history.

(56) References Cited

U.S. PATENT DOCUMENTS

| | | | |
|---|---|---|---|
| 2,733,440 A | | 2/1956 | Jenny et al. |
| 3,708,095 A | | 1/1973 | Briggs, Jr. |
| 3,908,884 A | | 9/1975 | Schrepferman |
| 4,053,094 A | | 10/1977 | Males |
| 4,197,974 A | | 4/1980 | Morton et al. |
| 4,253,598 A | | 3/1981 | Haytayan |
| 4,463,888 A | | 8/1984 | Geist et al. |
| 4,597,517 A | | 7/1986 | Wagdy |
| 4,624,401 A | | 11/1986 | Gassner et al. |
| 4,688,710 A | | 8/1987 | Massari, Jr. et al. |
| 4,832,245 A | | 5/1989 | Terayama et al. |
| 4,858,812 A | | 8/1989 | Fealey |
| 5,197,647 A | | 3/1993 | Howell |
| 5,297,713 A | | 3/1994 | Perra et al. |
| 5,433,367 A | | 7/1995 | Liu |
| 5,873,509 A | | 2/1999 | Liao |
| 6,012,622 A | | 1/2000 | Weinger et al. |
| 6,036,072 A | | 3/2000 | Lee |
| 6,053,389 A | | 4/2000 | Chu et al. |
| 6,131,787 A | | 10/2000 | Curtis |
| 6,199,739 B1 | | 3/2001 | Mukoyama et al. |
| 6,290,115 B1 | | 9/2001 | Chen |
| 6,296,167 B1 | | 10/2001 | Jen |
| 6,425,306 B1 | | 7/2002 | Habermehl |
| 6,499,642 B1 | | 12/2002 | Amada |
| 6,679,413 B2 | | 1/2004 | Miller et al. |
| 6,772,931 B2 | | 8/2004 | Miller et al. |
| 7,137,541 B2 | | 11/2006 | Baskar et al. |
| 7,138,595 B2 | | 11/2006 | Berry et al. |
| 7,165,305 B2 | | 1/2007 | Kenney et al. |
| 7,213,732 B2 | | 5/2007 | Schell et al. |
| 7,213,733 B1 | | 5/2007 | Wen |
| 7,314,155 B2 | | 1/2008 | Moeller et al. |
| 7,503,401 B2 | | 3/2009 | Gross et al. |
| 7,641,089 B2 | * | 1/2010 | Schell ..................... B25C 1/188 227/107 |
| 7,810,688 B2 | | 10/2010 | Wu et al. |
| 7,980,439 B2 | | 7/2011 | Akiba et al. |
| 2003/0042285 A1 | | 3/2003 | Wang |
| 2003/0230622 A1 | | 12/2003 | Rotharmel |
| 2005/0050712 A1 | | 3/2005 | Lat et al. |
| 2006/0016843 A1 | | 1/2006 | Ishizawa et al. |
| 2006/0169738 A1 | | 8/2006 | Ogawa et al. |
| 2006/0249554 A1 | | 11/2006 | Butzen et al. |
| 2007/0075112 A1 | | 4/2007 | Porth et al. |
| 2008/0099526 A1 | | 5/2008 | Brendel et al. |
| 2008/0251567 A1 | | 10/2008 | Shkolnikov et al. |
| 2008/0302846 A1 | | 12/2008 | Thompson |
| 2008/0308597 A1 | | 12/2008 | Wojcicki |
| 2009/0050667 A1 | | 2/2009 | Po |
| 2009/0200354 A1 | * | 8/2009 | Arata ...................... B25C 1/005 227/132 |
| 2009/0250500 A1 | | 10/2009 | Brendel et al. |
| 2010/0206934 A1 | | 8/2010 | Vallon et al. |
| 2011/0132959 A1 | | 6/2011 | Hlinka |

FOREIGN PATENT DOCUMENTS

| | | |
|---|---|---|
| EP | 2002935 A2 | 12/2008 |
| WO | 2007126735 A2 | 11/2007 |

OTHER PUBLICATIONS

European Patent Office. Eurpoean Search Report for or EP 13170109.6 (dated Jun. 2, 2016).

* cited by examiner

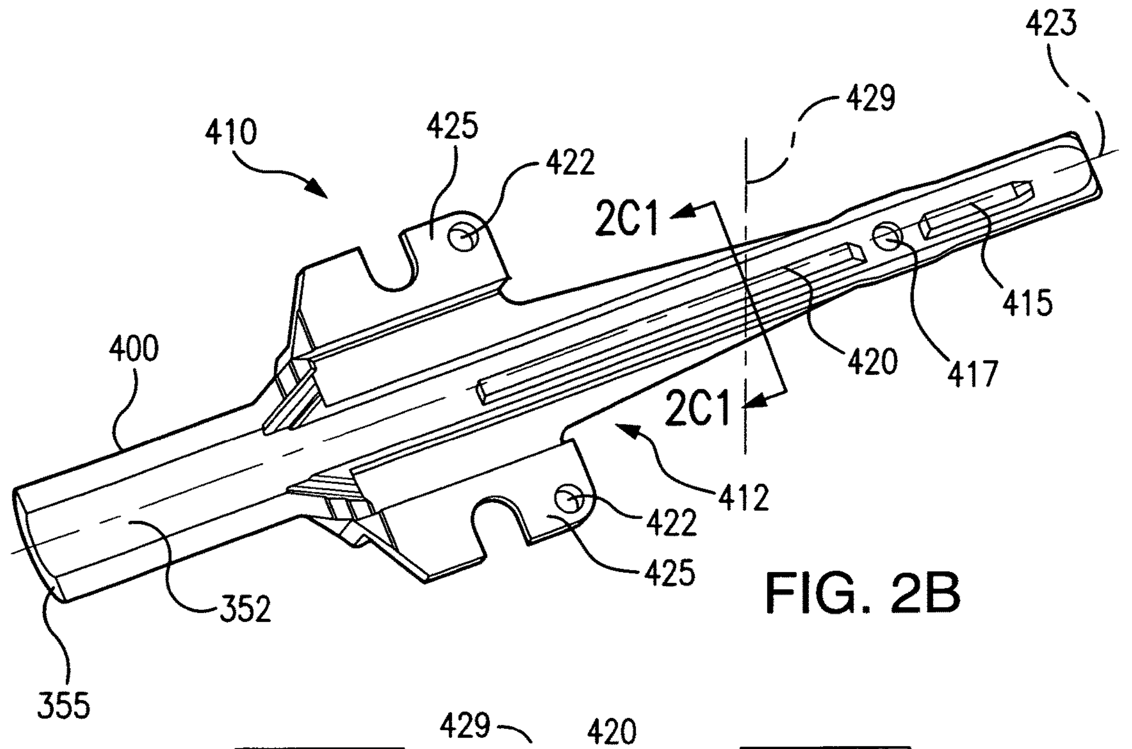
FIG. 2B
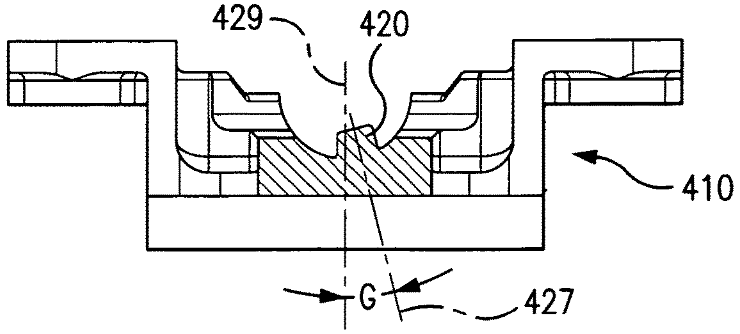
FIG. 2C1
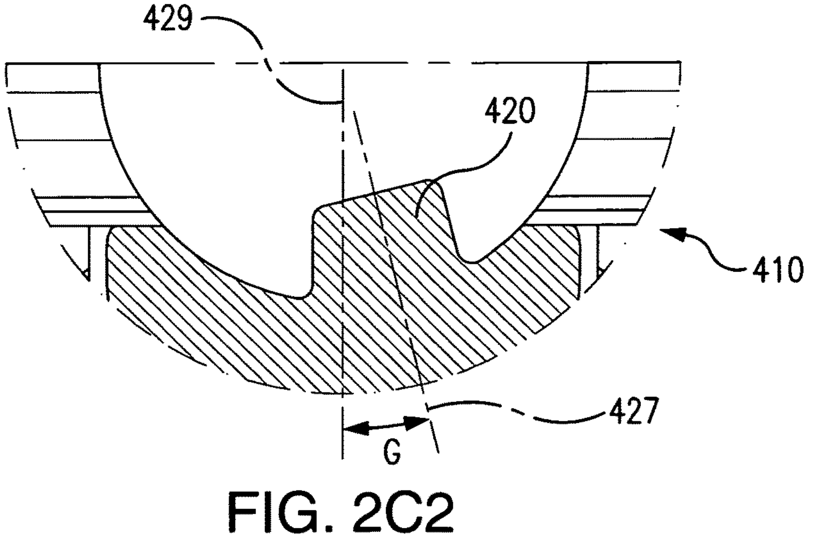
FIG. 2C2

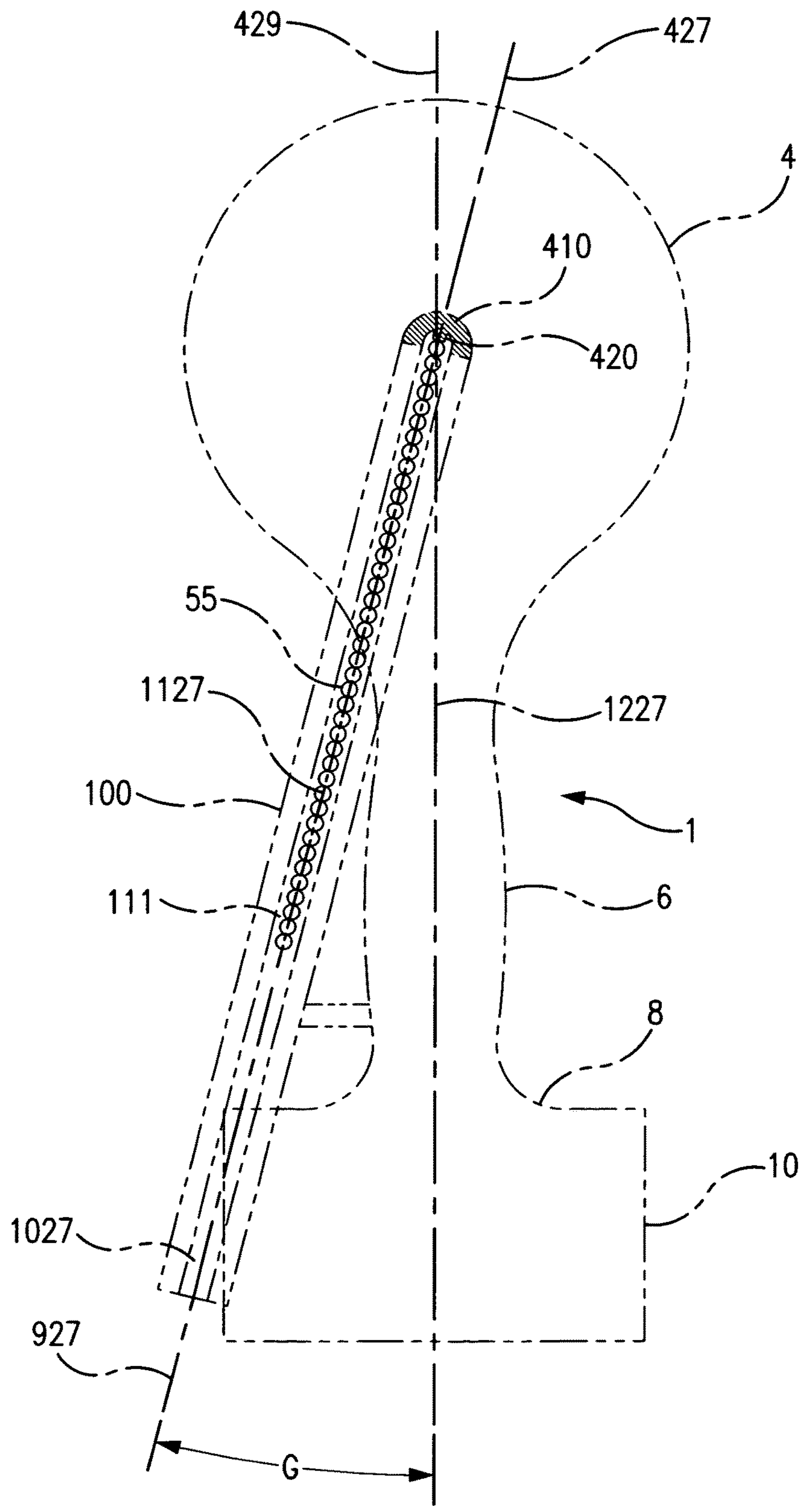
FIG. 2C2A

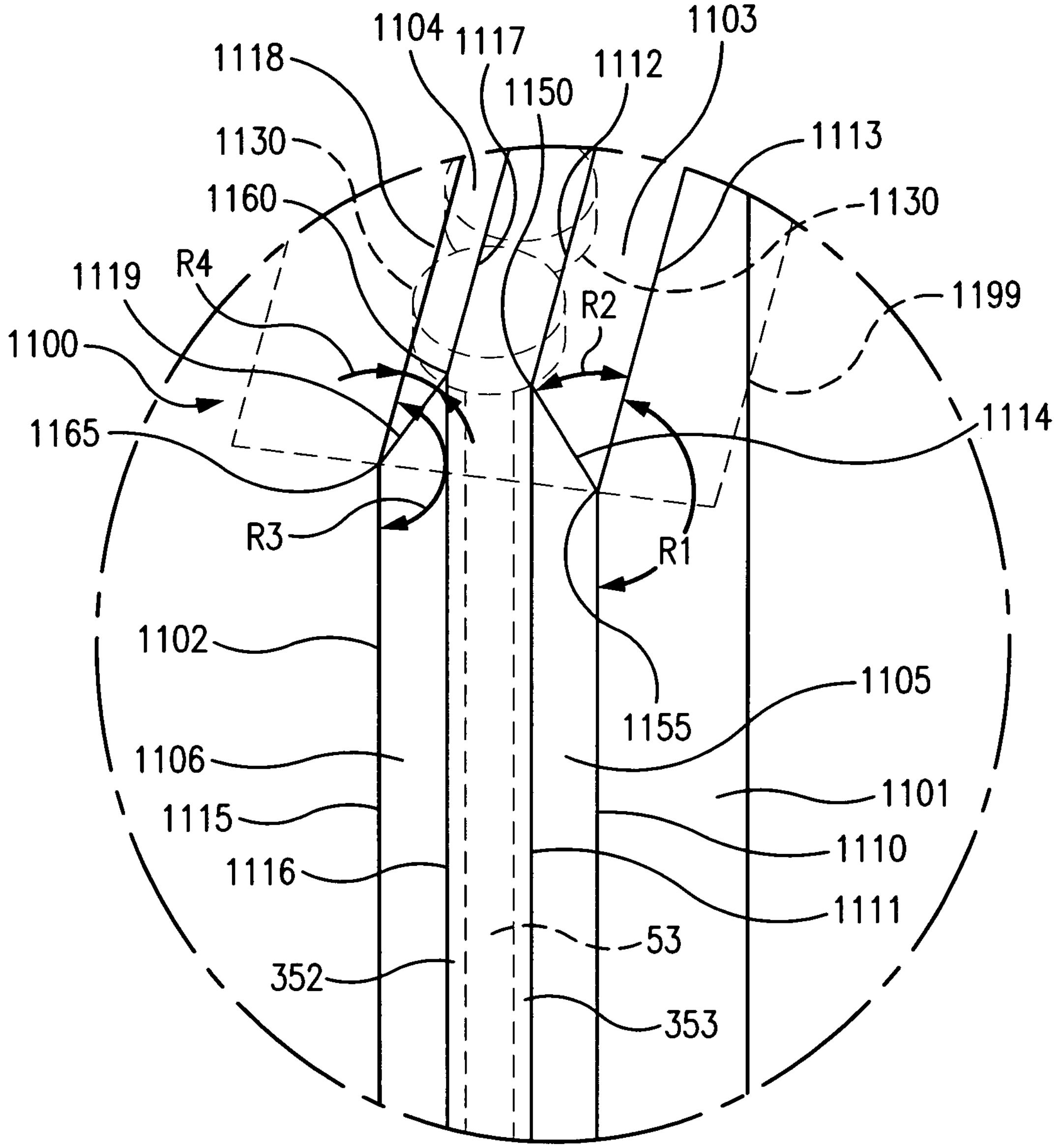
FIG. 2E1

FIG. 10A1

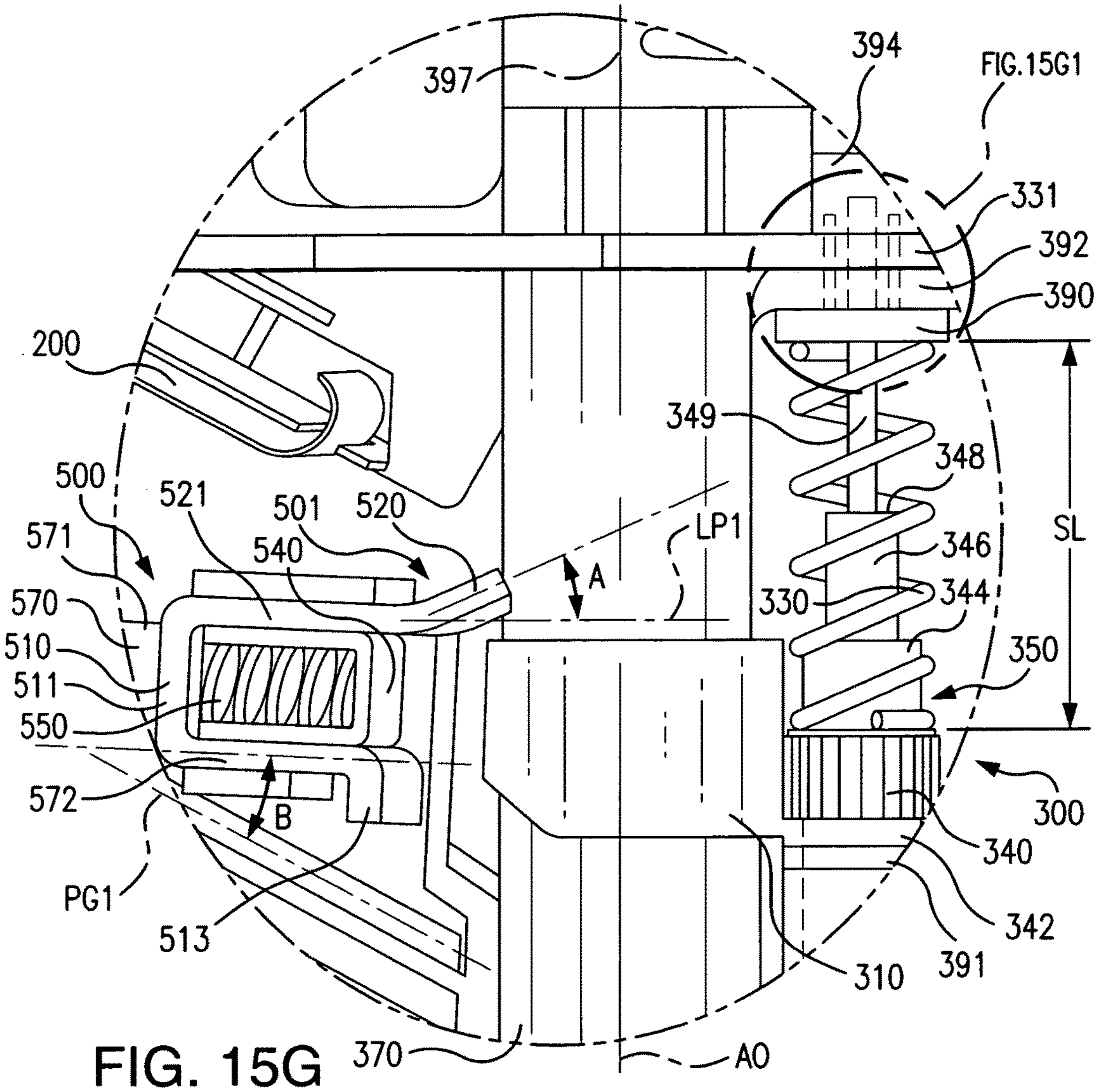
FIG. 15G
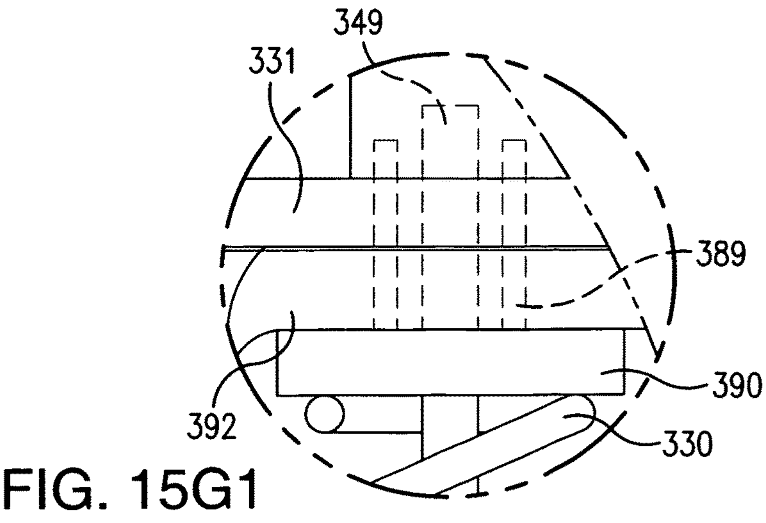
FIG. 15G1

POWER TOOL HAVING LATCHED PUSHER ASSEMBLY

CROSS-REFERENCE TO RELATED APPLICATIONS

This patent application is a continuation in part of and claims the benefit of the filing date of U.S. patent application Ser. No. 13/485,007 entitled "Magazine Assembly For Fastening Tool" filed on May 31, 2012, which issued as U.S. Pat. No. 9,643,305 on May 9, 2017.

INCORPORATION BY REFERENCE

This patent application incorporates by reference in its entirety copending U.S. patent application Ser. No. 13/485,007 entitled "Magazine Assembly For Fastening Tool" filed on May 31, 2012, which issued as U.S. Pat. No. 9,643,305 on May 9, 2017.

FIELD OF THE INVENTION

The present invention relates to a fastening tool having a latched pusher assembly.

BACKGROUND OF THE INVENTION

Fastening tools, such as nailers, are used in the construction trades. However, many fastening tools which are available do not provide an operator with fastener magazines which are capable of easily accomplished, efficient and effective use, operation and reloading. Often, available fastening tools have noses which are insufficient in design, heavy in weight, experience misfire, exhibit poor fastener positioning before firing and produce unacceptable rates of damaged fasteners when fired. Further, many available fastening tools do not adequately guard the moving parts of a nailer driving mechanism from damage.

Additional difficulties which exist regarding many available fastener magazines include difficult and inefficient fastener loading procedures. Inconvenient or problematic procedures are required to activate a fastening tool for use after fastener reloading. Reloading problems exist in magazines in which reloading requires a fastener feeder to be moved in a direction inconsistent with the loading of new fasteners and/or in which one or more internal pieces mechanically obstruct or impinge upon a fastener pathway. Many existing magazines for feeding fasteners are particularly problematic under field conditions in which fastening tools are used and in view of the number of fasteners typically fastened during the use of a fastening tool.

There is a strong need for an improved magazine for use with a fastening tool. There is also a strong need for an improved fastening tool nose. Additionally, there is a strong need for a reliable and an effective nose protection mechanism. Thus, there is a need for a fastening tool having improvements in its magazine, nose and nose protection.

SUMMARY OF THE INVENTION

In an embodiment, the fastening device disclosed herein can have a magazine having: a pusher assembly adapted to have an engaged state and a retracted state; the pusher assembly having a pusher assembly knob; the pusher assembly knob can be connected to a pusher; the pusher can be adapted to contact a nail and to impart a force upon the nail in a direction toward a nosepiece when the pusher assembly is in the engaged state; the magazine comprises a recess into which the pusher is reversibly retracted when the pusher assembly knob is moved to reversibly retract the pusher at least in part into the recess to achieve the retracted state; and a detent adapted to reversibly maintain the pusher assembly in the retracted state.

The pusher assembly can have a pusher assembly knob and a pusher which is adapted to contact a fastener and to impart a force upon the fastener in a direction toward a nose end of the magazine when the pusher assembly is in the engaged state. The magazine can also have the recess into which the pusher can be reversibly retracted at least in part when the pusher assembly knob is moved to reversibly retract the pusher to achieve the retracted state, as well as have a detent adapted to reversibly maintain the pusher assembly in the retracted state. The pusher assembly knob can be adapted to reversibly latch to the detent. The detent can have a latch portion to which the pusher assembly knob can be reversibly latched when the pusher assembly is in the retracted state. In an embodiment, the detent can have a detent base end to which the pusher assembly knob can reversibly latch. In another embodiment, the detent can have a spring latch to which the pusher assembly knob can reversibly latch.

In an embodiment, the pusher assembly can have a spring located between the pusher assembly knob and the pusher. The spring can allow the pusher assembly knob to be tilted to achieve an unlatched state from a latched state. The spring can be a compressive spring. In another embodiment, the pusher assembly can be free of a compressive spring between the pusher assembly knob and a portion of the pusher.

The pusher assembly can have a pusher assembly knob which optionally can be pivoted to release the pusher assembly knob from the detent to achieve an unlatched state from a latched state. In an embodiment, the pusher assembly optionally can have a pivot about which a pivot stem can move to release the pusher assembly knob from the detent to achieve an unlatched state from a latched state.

In an embodiment, the magazine can have a guide frame which has the detent. The detent can be located proximate to a pusher assembly guide path. The pusher assembly can be biased by a constant force spring. Optionally, the pusher assembly can be configured such that the pusher assembly knob has a knob clearance of 0.05 mm or greater when the pusher assembly is in an engaged state. The magazine disclosed herein, can be used with a nailer having one or a plurality of nails.

In an embodiment, the fastening device can have a nosepiece adapted to receive a fastener from a magazine, as well as having a power source adapted to power a fastener driving mechanism which can drive the fastener into a workpiece when triggered. The pusher assembly can be adapted to have an engaged state and a retracted state, as well as to have a pusher assembly knob and a pusher. The pusher can be adapted to contact a fastener and can impart a force upon the fastener in a direction toward the nosepiece when the pusher assembly is in the engaged state. The magazine can have a recess into which the pusher can be reversibly retracted at least in part when the pusher assembly knob is moved to reversibly retract the pusher to achieve the retracted state. A detent can be adapted to reversibly maintain the pusher assembly in the retracted state. In an embodiment, the detent can have a latch to which the pusher assembly knob is reversibly latched when the pusher is in the retracted state. The latch can be a spring latch.

In an embodiment, the fastening device can use a method for loading fasteners into a magazine of a fastening device, comprising the steps of: providing a magazine having a pusher assembly adapted to have an engaged state and a retracted state, the pusher assembly having a pusher assembly knob connected to a pusher, the pusher adapted to contact a fastener and to impart a force upon the fastener in a direction toward a nose end of the magazine when the pusher assembly is in the engaged state; providing a recess of the magazine into which the pusher is reversibly retracted at least in part when the pusher assembly knob is moved to reversibly retract the pusher to achieve the retracted state; providing a detent of the magazine adapted to reversibly maintain the pusher assembly in the retracted state in which the pusher assembly knob is adapted to reversibly latch to the detent; reversibly retracting the pusher assembly into the retracted state; maintaining the pusher assembly in the retracted state; feeding one or more fasteners to the track; and engaging the pusher assembly from the retracted state into the engaged state. In an embodiment, the step of feeding one or more fasteners into the track can also have the step of feeding one or more nails into the track.

In an embodiment, the fastening device can have a means for reversibly retracting a pusher assembly which can have a means for reversibly latching a pusher assembly knob to a detent. The means for reversibly latching a pusher assembly knob to the detent can be adapted to reversibly latch a portion of the pusher assembly knob to the detent when the pusher assembly is in a retracted state. In an embodiment, the means can be adapted to unlatch the pusher assembly knob when a pivoting motion is imparted to the pusher assembly knob.

The magazine can have a detent which has a raised portion located along the pusher assembly guide path and configured to reversibly mate with an indentation in a pusher assembly knob. The magazine can also have a spring loaded detent.

The magazine can have a pusher assembly knob which is configured to reversibly mate with a detent, and in which the pusher assembly knob can be reversibly fixed in place when the detent and the knob are reversibly mated together.

The magazine can have a detent having a detent base end portion configured to reversibly mate with a pusher assembly knob base portion.

The magazine can have a detent which has a raised portion configured to reversibly mate with the pusher assembly knob. A magazine for a fastening device according to claim which can have a stop which is located proximate to the detent.

The magazine can have a pusher guide track which can guide the path of the pusher.

The magazine can have a guide track ramp configured such that the pusher can be reversibly moved from a position at least in part in the recess guided by the guide track ramp to a position along the pusher guide track.

In another embodiment the fastening tool disclosed herein can have: a nosepiece adapted to receive a fastener from a magazine; a power source adapted to power a fastener driving mechanism which can drive the fastener when triggered; the magazine having a pusher assembly adapted to have an engaged state and a retracted state; the pusher assembly having a pusher assembly knob; the pusher assembly knob is connected to a pusher; the pusher adapted to impart a force upon a nail in a direction toward the nosepiece when the pusher assembly is in the engaged state; the magazine having a recess into which the pusher is reversibly retracted when the pusher assembly knob is moved to reversibly retract the pusher at least in part into the recess to achieve a retracted state; and a detent adapted to reversibly maintain the pusher assembly in the retracted state.

The fastening tool can be a nailer and the fastener can be a nail.

The fastening tool can have a detent which has a raised portion located along the pusher assembly guide path and configured to reversibly mate with an indentation in a pusher assembly knob.

The fastening tool can have a detent which can be a spring loaded detent.

The fastening tool can have a pusher assembly knob is configured to reversibly mate with the detent. The pusher assembly knob can be reversibly fixed in place when the detent and the knob are reversibly mated together.

In yet another embodiment, the magazine for a fastening device disclosed herein can have: a pusher assembly adapted to have an engaged state and a retracted state, the pusher assembly having a pusher; the magazine having a recess into which the pusher at least in part is reversibly retracted when the pusher assembly is in a retracted state; a means for reversibly retracting the pusher at least in part into the recess; and a means for reversibly maintaining the pusher assembly in a retracted state.

The fastening device can be a nailer and the fastener can be a nail.

The magazine can have a means for reversibly maintaining the pusher assembly in a retracted state. In an embodiment, such means can be a detent, latch or stop.

The magazine can have a means to apply a motive force to a pusher to engage the pusher with a fastener when the pusher is not maintained is a retracted state.

In an aspect, the fastening tool can be loaded with fasteners by a method having the steps of: providing a magazine with a pusher assembly adapted to have an engaged state and a retracted state, the magazine having a detent adapted to maintain the pusher assembly in the retracted state, the magazine also having a track for a feeding one or more fasteners, proving a recess in the magazine configured to receive at least a portion of the pusher assembly to allow for the feeding one or more fasteners when the pusher assembly is in the retracted state, reversibly retracting the pusher assembly into the retracted state, maintaining the retracted state by using the detent to maintain the pusher assembly in the retracted state, feeding one or more fasteners to the track, and engaging the pusher assembly from the retracted state into the engaged state.

The method for loading fasteners into a magazine for a fastening device can have a step of feeding one or more fasteners into the track and further have a step of feeding one or more nails into the track.

In another aspect, the fastening tool can have a nosepiece with a nosepiece insert which optionally can be investment cast and made of a light weight material such as aluminum, or steel. The nosepiece insert can have a nail stop which can be offset from a nosepiece insert centerline The nail stop can have a dimension such that a nail will not have contact with the nail stop after 10 percent of the length of the nail has been driven. The nail stop can be shorter than the length of the shortest nail used with the magazine.

In yet another aspect, a fastening tool can have a magazine having a lockout which can a locked out state when no nails, or a predetermined number of nails, are present in the magazine. The lockout can inhibit the movement of a contact trip when a predetermined number of nails (or zero (0) nails) are present in the magazine. This inhibition of movement of upper contact trip can make an operator aware that a nail is not going to be driven and that it is appropriate to reload nails or to add more nails.

The lockout can be an angled lockout having a locking leg which does not meet a contact trip at a perpendicular angle to the direction of motion of the contact trip.

The lockout can also protect the components constituting the fastening tool's nosepiece assembly from an application of force resulting from a drop or misuse. In an embodiment, a lockout override can occur when an override force is reached.

BRIEF DESCRIPTION OF THE DRAWINGS

The present invention in its several aspects and embodiments solves the problems discussed above and significantly advances the technology of fastening tools. The present invention can become more fully understood from the detailed description and the accompanying drawings, wherein:

FIG. 2B is a detailed view of a nosepiece insert viewed from the channel side;

FIG. 2C1 is a detailed view of nosepiece insert section 2C1 of FIG. 2B;

FIG. 2C2 is a detailed view of a nosepiece insert having nail stop offset at an angle;

FIG. 2C2A is a perspective view illustrating the alignment of the nailer, magazine, nails and nail stop;

FIG. 2E1 is a detailed view of a nail feed funnel;

FIG. 10A1 is a detail view of a knob stem and plug configuration;

FIG. 15G is a nail-side detailed view of the lockout mechanism in a locked out state and an upper contact trip in a position not in contact with the lockout mechanism;

FIG. 15G1 is a nail-side detail view of an upper stop having a bushing;

DETAILED DESCRIPTION OF THE INVENTION

The inventive fastening tool can be of a wide variety of designs and can be powered by a number of power sources. For example, power sources for the fastening tool can be manual, pneumatic, electric, combustion, solar or use other (or multiple) sources of energy.

In one aspect, an inventive magazine for a fastening tool can be easy for an operator to handle and use. It can also be reliable and efficient for reloading fasteners. The magazine provides a means to retract a fastener pusher from an engaged state and to hold the fastener pusher (herein also as "pusher") in a retracted state. Retraction of the pusher to a retracted state can free an operator from having to maintain the state of the pusher by using one or more hands. Freeing an operator's hands in this fashion facilitates an operator's loading of fasteners into the magazine, or removing fasteners from the magazine. The pusher of the magazine disclosed herein is easily reengaged to push fasteners. Its reengagement requires minimal operator actions (e.g. pushing a knob, or freeing a pusher assembly from a restriction on its motion by a detent).

Figure 1:
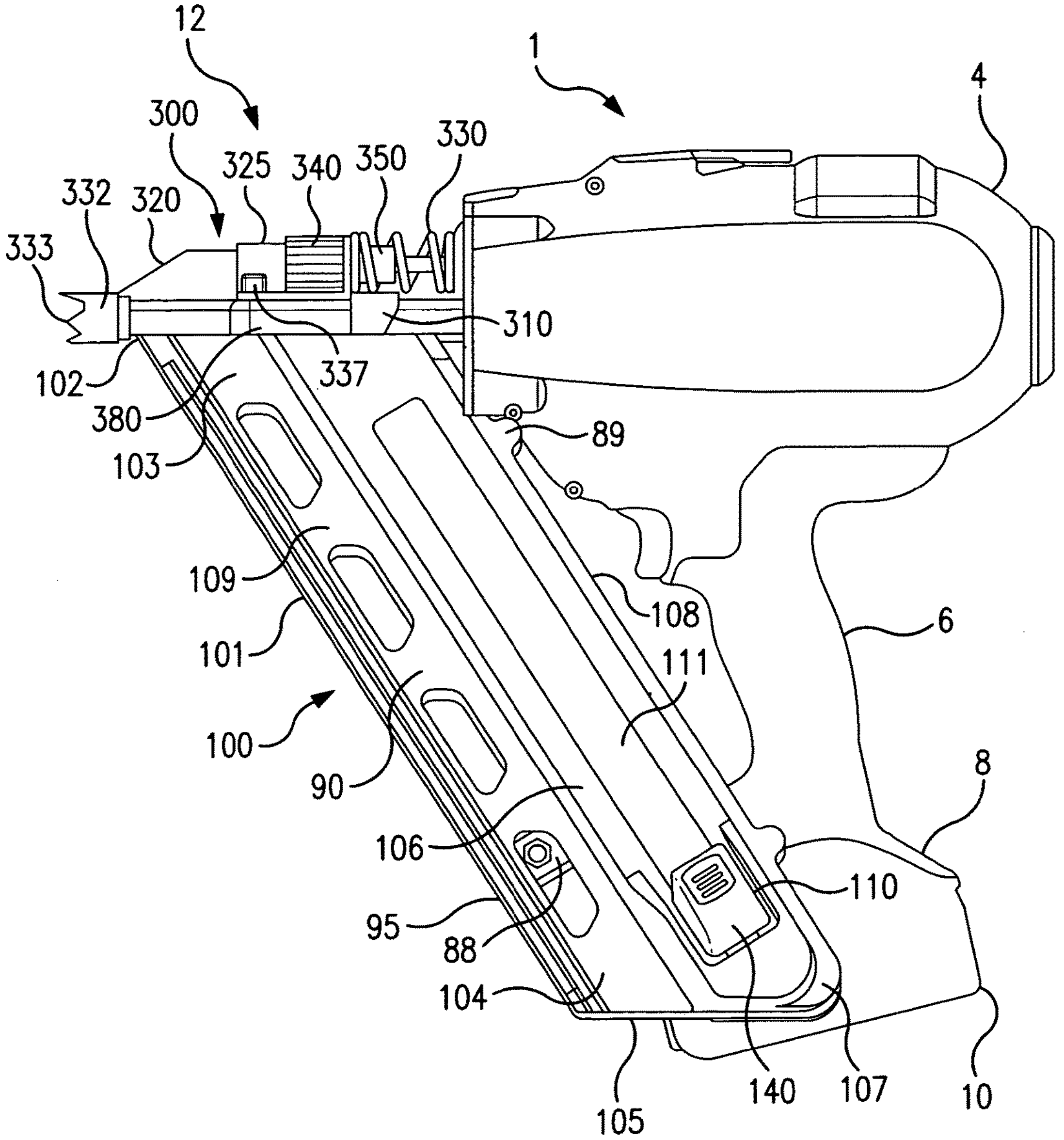
FIG. 1 is a knob-side side view of an exemplary nailer having a fixed nosepiece assembly and a magazine.

In an embodiment shown in FIG. 1, the pusher can be reengaged by a motion of an operator upon an element of the pusher assembly 110, such as moving a pusher assembly knob 140. In an embodiment, the fastener pusher is adapted for pushing nails.

Figure 2:
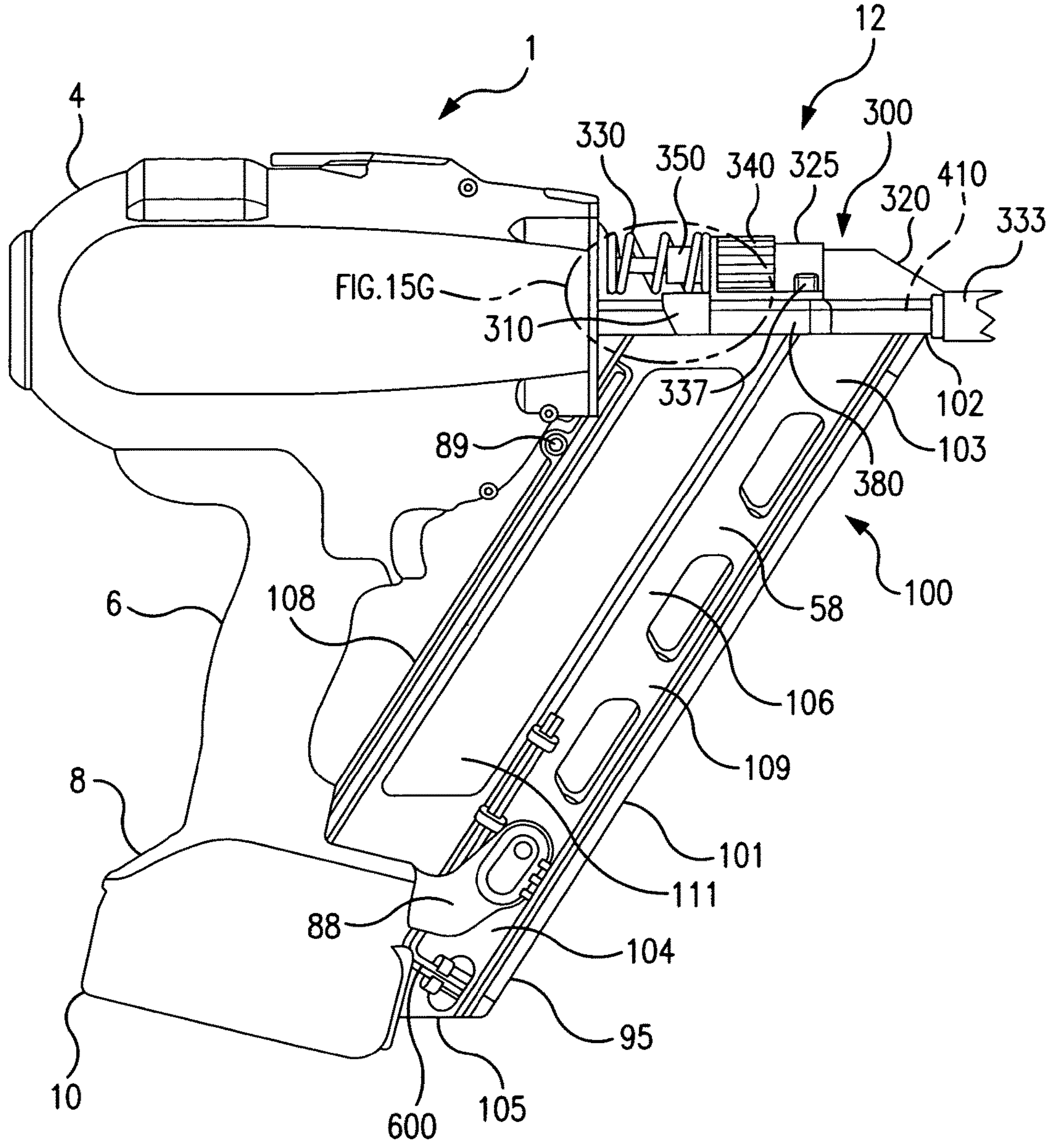
FIG. 2 is a nail-side view of an exemplary nailer having a fixed nosepiece assembly and a magazine.
Figure 2A:
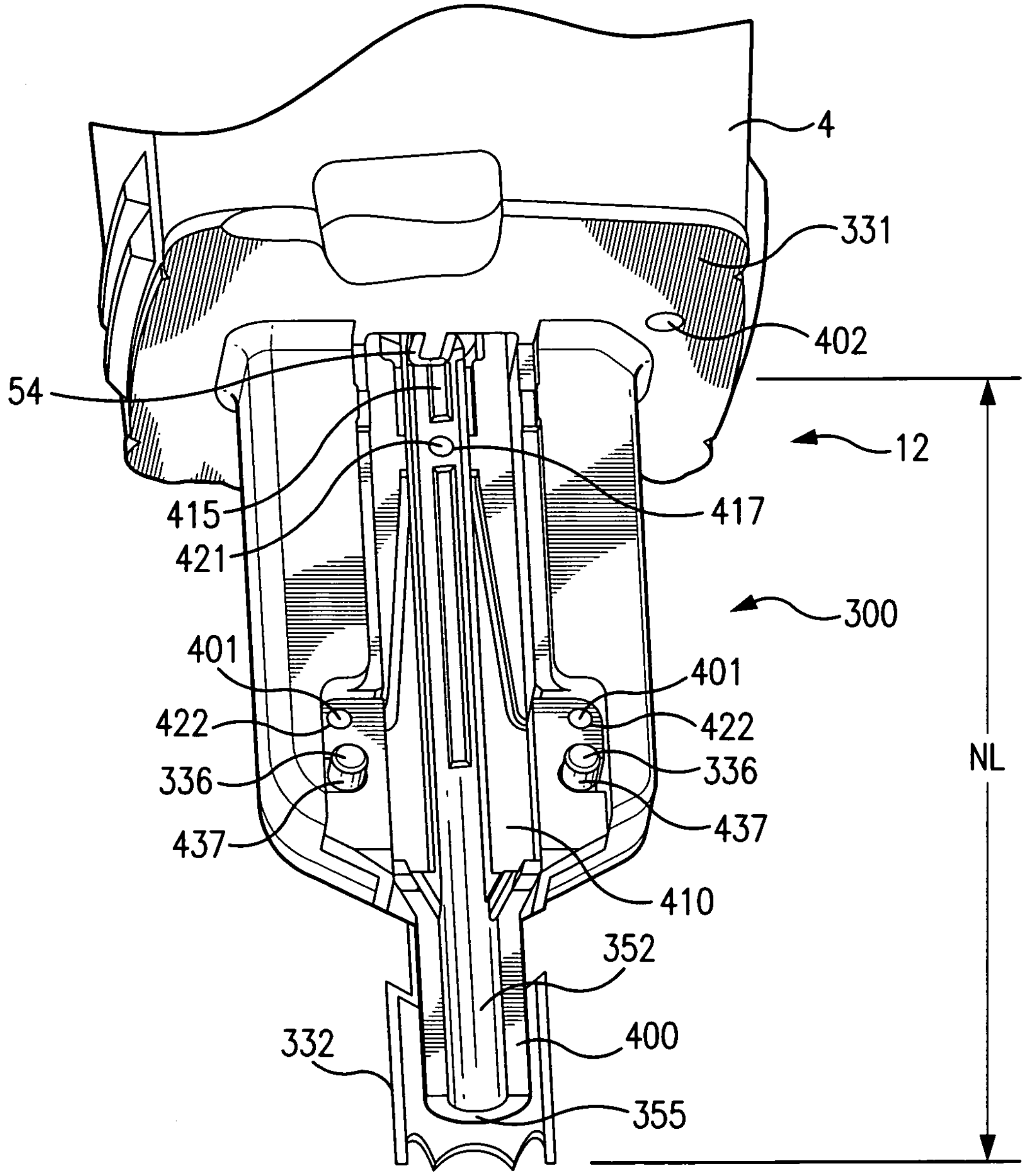
FIG. 2A is a detail view of an embodiment of a fixed nosepiece.

Additionally, the pusher design and operation can cause (or allow) an operator action of retracting or engaging the pusher and/or loading the magazine to occur in the same longitudinal direction as the movement of the pusher when it is in an engaged state and pushing fasteners, for example along longitudinal centerline 927 of a magazine 100 as shown in FIG. 2C2A, such that the motion of the pusher can be intuitive to an operator using the magazine. The magazine disclosed herein can be used with a broad variety of fastening tools, including but not limited to, nailers, drivers, riveters, screw guns and staplers. Fasteners which can be used with the magazine 100 can be in non-limiting example, roofing nails, finishing nails, duplex nails, brads, staples, tacks, masonry nails, screws and positive placement/metal connector nails, rivets and dowels.

In an embodiment in which the fastening tool is a nailer, an operator action of moving a pusher assembly can retract a nail pusher and latch it in place achieving and maintaining its retracted state which allows for nail loading. Additionally, an operator action of moving a pusher assembly (and/or pusher assembly knob and/or other latching component) can unlatch the pusher assembly to engage it for tool operation. Further, the direction of action for the movement of the nail pusher to retract or to engage can be along the same longitudinal axis as that of pushing nails in the magazine and/or loading nails in the magazine. The same benefits exist when using the magazine for fasteners other than nails.

The inventive magazine in its several embodiments and many aspects can be employed for use with fastening tools other than nailers and can be used with fasteners other than nails. Additional areas of applicability of the present invention can become apparent from the detailed description provided herein. The detailed description and specific examples herein are not intended to limit the scope of the invention. The claims of this application are to be broadly construed.

FIG. 1 is a side view of an exemplary nailer having a magazine viewed from the knob-side 90 (e.g., FIG. 1 and FIG. 3) and showing the pusher assembly knob 140.

With reference to FIG. 1, a magazine 100 which is constructed according to the principles of the present invention is shown in operative association with a nailer 1. In this FIG. 1 example, nailer 1 is a cordless nailer. However, the nailer can be of a different type and/or a different power source. The applicability and use of the magazine 100 is broad and can be used with many fastening tools. The applicability and use of the magazine 100 is not limited by the power supply used by a tool having the magazine 100.

Nailer 1 has a housing 4 and a motor (which can be covered by the housing 4) which drives a nail driving mechanism for driving nails which are fed from the magazine 100. The terms "driving" and "firing" are used synonymously herein regarding the action of driving or fastening a fastener (e.g. a nail) into a workpiece. A handle 6 extends from housing 4 to a base portion 8 having a battery pack 10. Battery pack 10 is configured to engage a base portion 8 of handle 6 and provides power to the motor such that nailer 1 can drive one or more nails which are fed from the magazine 100.

Nailer 1 has a nosepiece assembly 12 which is coupled to housing 4. The nosepiece can be of a variety of embodiments. In a non-limiting example, the nosepiece assembly 12 can be a fixed nosepiece assembly 300 (e.g. FIG. 1), or a latched nosepiece assembly 13 (e.g. FIG. 3) as disclosed herein.

The magazine 100 can optionally be coupled to housing 4 by coupling member 89. The magazine 100 has a nose portion 103 which can be proximate to the fixed nosepiece assembly 300. The magazine 100 engages the fixed nosepiece assembly 300 at a nose portion 103 of the magazine 100 which has a nose end 102. The magazine 100 can be coupled to a base portion 8 of a handle 6 at a base portion 104 of magazine 100 by base coupling member 88. The base portion 104 of magazine 100 is proximate to a base end 105 of the magazine 100.

The magazine can have a magazine body 106 with an upper magazine 107 and a lower magazine 109. An upper magazine edge 108 is proximate to and can be attached to housing 4. The lower magazine 109 has a lower magazine edge 101.

Figure 6:
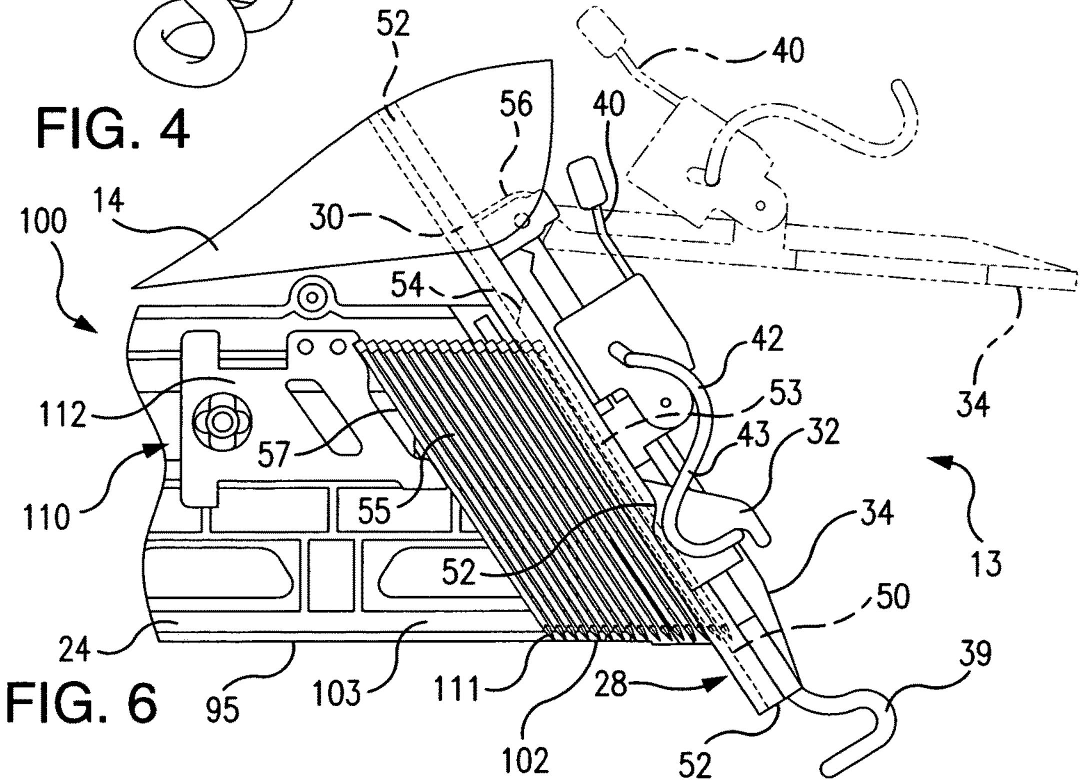
FIG. 6 is a side view of the latched nosepiece assembly having a driver blade.

The magazine includes a nail track 111 sized to accept a plurality of nails 55 therein (e.g. FIG. 6). The nails can be guided by a feature of the upper magazine 107 which guides at least one end of a nail. In an embodiment, the upper magazine 107 can guide a portion of a nail proximate to at least one end of the nail, or can guide a portion of the nail comprising an end. In an embodiment, upper magazine 107 guides on or proximate to a nail end which is or has a nail head. In another embodiment, lower magazine 109 guides another portion of the nail or at another end of the nail. In an embodiment, lower magazine 109 guides a nail proximate to or at its nail tip.

In an embodiment, the plurality of nails 55 can have nail tips which are supported by a lower liner 95. The plurality of nails 55 are loaded into the magazine 100 by inserting them into the nail track 111 through a nail feed slot 59 (e.g. FIG. 11 and FIG. 12) which can be located at or proximate to the base end 105. The magazine 100 can have a nail track 111 which is sized to accept a plurality of nails 55 therein. The plurality of nails 55 can be moved through the magazine 100 towards the fixed nosepiece assembly 300 (or generally, a nosepiece assembly 12) by a force imparted by contact from the pusher assembly 110.

FIG. 1 illustrates an example embodiment of the fixed nosepiece assembly 300 which has an upper contact trip 310 and a lower contact trip 320. The lower contact trip 320 can be guided and/or supported by a lower contact trip support 325. The fixed nosepiece assembly 300 also can have a nose 332 which can be designed to have a nose tip 333 which can facilitate temporary and reversible placement on a workpiece by having at least one of e.g.: a pointed portion, a serration, a tooth, a high friction or adhesive portion, or other feature which can facilitate a temporary and reversible placement of the nose 332 on a workpiece. When the nose 332 is pressed against a workpiece, the lower contact trip 320 and the upper contact trip 310 can be moved toward the housing 4 and a contact trip spring 330 is compressed.

In an embodiment, the upper contact trip 310 is connected to an activation rod 403 (e.g. FIGS. 15I, 15J and 17A) which is a linkage which can strike a contact trip actuator 700 (e.g. FIG. 17A) which then contacts and activates a tactile switch 800 (e.g. FIG. 17A) sending a signal to a microprocessor which runs a machine executable code that turns a motor and drives a nail with a driver blade 54 (e.g. FIG. 2A).

The fixed nosepiece assembly 300 is adjustable having a depth adjust allowing the user to adjust the firing characteristics of the fixed nosepiece assembly 300. In the embodiment of FIG. 1, a depth adjustment wheel 340 can be moved to affect the position of a depth adjustment rod 350. In an embodiment, the depth adjustment wheel 340 is a thumbwheel. The position of the depth adjustment rod also affects the distance between nose tip 333 and insert tip 355 (e.g. FIG. 2A).

Additionally, the depth adjustment wheel 340 (or other means of depth adjustment) allows an operator to determine how much of a nail's length can be driven into a workpiece and how much of the nail's length under its nail head can be located at a distance from a workpiece surface. In an embodiment, depth adjustment can be achieved by changing the relative distance between the upper contact trip 310 and the lower contact trip 320.

In an embodiment, rotating the depth adjustment wheel 340 can move a depth adjustment rod 350 by means of engagement to the depth adjustment rod 350 by machined flats of the depth adjustment wheel 340 into which the depth adjustment rod 350 mates. The lower contact trip 320 and the depth adjustment rod 350 can be connected by threads. In an embodiment, the lower contact trip 320 can not rotate with the depth adjustment rod 350 which forces the lower contact trip 320 to move axially with respect to the depth adjustment rod 350. In an embodiment, the range of adjustment can be a value in a range of from no adjustment (i.e. zero (0) mm) to 13.5 mm or greater. In an embodiment, the range of depth adjustment can be limited by a roll pin (not shown) assembled with relation to the lower contact trip 320 and the front face of the depth adjustment wheel 340. The roll pin can be set to prevent the unscrewing of the depth adjustment rod 350 from the lower contact trip 320.

Numeric values and ranges herein, unless otherwise stated, also are intended to have associated with them a tolerance and to account for variances of design and manufacturing. Thus, a number can include values "about" that number. For example, a value X is also intended to be understood as "about X". Likewise, a range of Y-Z, is also intended to be understood as within a range of from "about Y-about Z". Unless otherwise stated, significant digits disclosed for a number are not intended to make the number an exact limiting value. Variance and tolerance is inherent in mechanical design and the numbers disclosed herein are intended to be construed to allow for such factors (in non-limiting e.g., ±10 percent of a given value). Likewise, the claims are to be broadly construed in their recitations of numbers and ranges.

In an embodiment, the lower contact trip and upper contact trip can move in coordination with each other. In an embodiment, the lower contact trip 320 can move independently of the upper contact trip 310. In an embodiment, a contact trip spring 330 can be used.

In an embodiment, a detenting feeling can be provided to the operator moving the depth adjustment wheel 340 by using one or more indexing bolts which can slide on a contact face of the upper contact trip 310 and optionally using two cold formed pockets that change the length of the spring every 180 degrees.

In an embodiment, using the depth adjustment wheel 340 allows for the movement of the lower contact trip 320 independent of the location of the upper contact trip 310.

In an embodiment, the magazine 100 is adapted to hold a means for releasing (or decoupling, or disconnecting) the fixed nosepiece 300 from the magazine 100. In an embodiment, the means can be at least a magazine screw 337 which can be a captive screw. In an embodiment, the magazine screw 337 can be screwed to couple the fixed nosepiece assembly 300 to the magazine 100, or unscrewed to decouple the magazine 100 from the fixed nosepiece assembly 300.

In an embodiment, one or more of a magazine screw 337 can be used to fix the nosepiece assembly 300 to the magazine 100. In the embodiment illustrated in FIG. 1 the depth to which the depth adjustment rod can be moved is a value from 0 mm to 13.5 mm. In an embodiment, one or more of the magazine screw 337 can be used to reversibly mate the nose end 102 of the magazine 100 captive to the fixed nosepiece assembly 300. Optionally, the magazine screw 337 can have a variety of screw heads. Optionally, the magazine screw 337 can be a captive screw. In an embodiment, the magazine screw 337 can be different from a nosepiece insert screw 401 (e.g. FIG. 2A).

Means for releasing the fixed nosepiece 300 from the magazine 100 can be as non-limiting examples a wrench, a screwdriver, an Allen wrench 600 (FIG. 2), or another device capable of loosening a fastener. Types of fasteners for fixing nosepiece 300 to the magazine 100 can be as non-limiting examples: a screw, a nail, a nut, a bolt or a reversible fastener. The exemplary wrench, screwdriver, or Allen wrench 600 can be adapted to fit with, turn (screw and unscrew; tighten or loosen) magazine screw 337. In another embodiment, the magazine screw 337 can have a head adapted for an operator to turn manually by use of an operator's fingers. For example, a butterfly head screw or folding butterfly head screw can be used, as well as other heads which allow for turning by fingers. This disclosure is to be broadly construed regarding the means for fixing or releasing the fixed nosepiece 300 from the magazine 100.

In an embodiment, the fixed nosepiece assembly 300 can fit with the magazine 100 by a magazine interface 380. In an embodiment, the nosepiece has a sensor which indicates when the fixed nosepiece assembly 300 is not properly or completely screwed into or connected to the magazine 100. This feature can reduce misfiring or bending of nails upon driving. In yet another embodiment, the sensor for indicating when the fixed nosepiece assembly 300 is not properly or completely screwed into or connected to the magazine 100 is installed in the magazine 100 or the casing 4. The sensor can also have a number of pieces with at least one placed in a nosepiece 12 and optionally another placed elsewhere, such as in the magazine 100 and/or the casing 4.

In another embodiment, the magazine 100 can have a sensor which indicates the number of nails remaining to be fired. In another embodiment, the magazine 100 can have a sensor which indicates the number of nails in the magazine 100. In another embodiment, the magazine 100 can have a sensor which indicates when the magazine has less than a set number of nails, or that the magazine is empty.

In yet another embodiment, the magazine 100 can have a nail length sensor which indicates a length of one or more of a plurality of nails 55 loaded into the magazine 100 and which can provide an input to a microprocessor of nailer 1. The microprocessor can execute machine readable code which can adjust the driving energy expended to drive a nail of an indicated length. Such an energy control system can extend battery life by controlling the energy expended in driving nails of an indicated length. This can constitute (or be part of) a fastener tool energy control system (e.g. nailer energy control system).

The magazine 100 achieves a fast, reliable and effective use and reloading of the magazine 100, and of a fastening tool using it (in the FIG. 1 illustration the tool is nailer 1). The magazine 100 can have a pusher assembly 110 which retracts a pusher 112 (e.g., FIG. 14A) into a pusher recess 171 (e.g., FIG. 14A) which removes the pusher 112 from obstructing a nail track 111 for movement of loaded fasteners or for feeding new fasteners into the magazine 100. In the exemplary nailer of FIG. 1, after insertion of a plurality of nails 55 into the nail track 111, the pusher assembly 110 can be engaged to move to a position behind the newly inserted plurality of nails 55 and to push the plurality of nails 55 forward for driving by nailer 1.

The magazine 100 can hold a plurality of nails 55 (FIG. 6) therein. A broad variety of fasteners usable with nailers can be used with the magazine 100. In an embodiment, collated nails can be inserted into the magazine 100 for fastening.

The pusher assembly 110 can be in a retracted state (e.g. FIG. 10A-H, FIG. 11, FIG. 12, FIG. 13 and FIG. 14A-B) allowing for the loading of the plurality of nails 55, or in an engaged state (e.g. FIG. 6, FIG. 8, FIG. 9, FIG. 14D, FIG. 15 and FIG. 16) in which the pusher assembly 110 pushes the plurality of nails 55 as feed to the nosepiece assembly 12 for driving. The nails can be fed toward the nose end 102 along the nail track 111 into the nosepiece assembly 12 by the pusher assembly 110 which has the pusher assembly knob 140. The pusher 112 of the pusher assembly 110 can be guided in its movement within the magazine 100 and a spring (e.g. a spring 200; see e.g. FIG. 10A) can apply force to the pusher assembly 110 to feed one or more of the plurality of nails 55 which are guided along the nail track 111 to the nosepiece assembly 12 for fastening.

Figure 3:
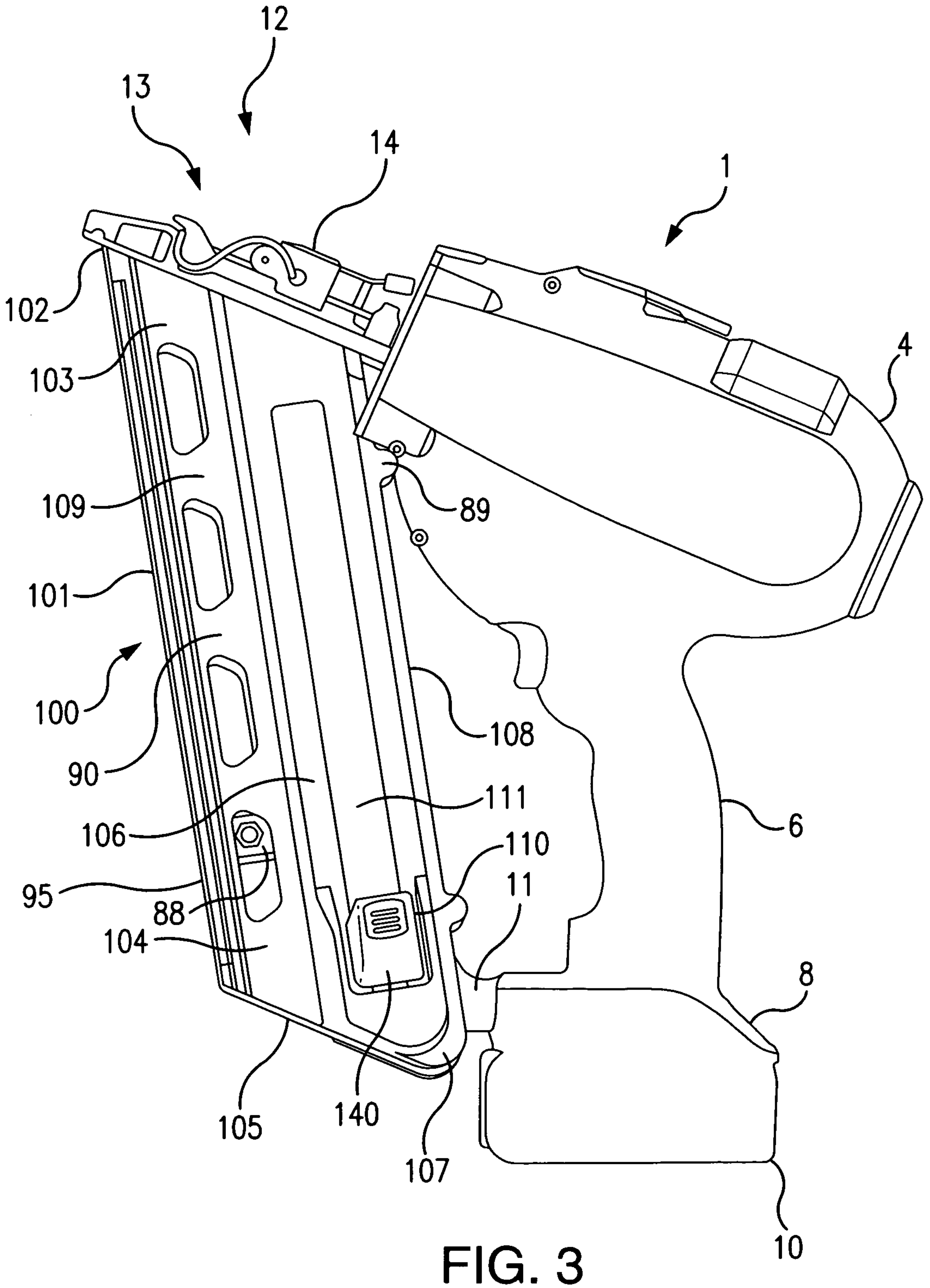
FIG. 3 is a knob-side view of an exemplary nailer having a magazine, a latched nosepiece and having a magazine coupled to the nailer's handle by a bracket.

FIG. 1 illustrates the nosepiece 12 of exemplary nailer 1 to be a fixed nosepiece assembly 300 (see also FIGS. 2A-2C). An example of the nosepiece 12 of an exemplary nailer 1 having a latched nosepiece assembly 13 is illustrated in FIG. 3 and detailed FIGS. 4-8.

As discussed herein in regard to e.g. FIGS. 10A-10H, 13 and 14A-D, a retracted state of the pusher assembly 110 for unloading, loading or reloading, can be achieved. In an embodiment, the pusher assembly 110 has a pusher assembly knob 140 which can be moved by the operator toward the base end 105 of the magazine where it can be reversibly fixed in place, or so as to have a limited range of motion but not fixed in place. The pusher assembly knob 140 is connected to the pusher 112. The movement of the pusher assembly knob 140 toward the base end 105 of the magazine where the pusher assembly knob 140 can be reversibly fixed moves the pusher 112 into the pusher recess 171. The movement of the pusher 112 into the pusher recess 171 results in a retracted stated of pusher assembly 110. The retracted state of the pusher assembly 110 can be maintained by reversibly fixing the pusher assembly knob 140 in place. Optionally, instead of fixing assembly knob 140 in place, a detent or mechanical means can be provided which prevents the pusher assembly knob 140 and/or the pusher 112 from movement out of the retracted state (e.g. FIGS. 10A-12) until the operator activates engagement of the pusher assembly 110 to push the plurality of nails 55 toward the nose end 102.

Figure 9:
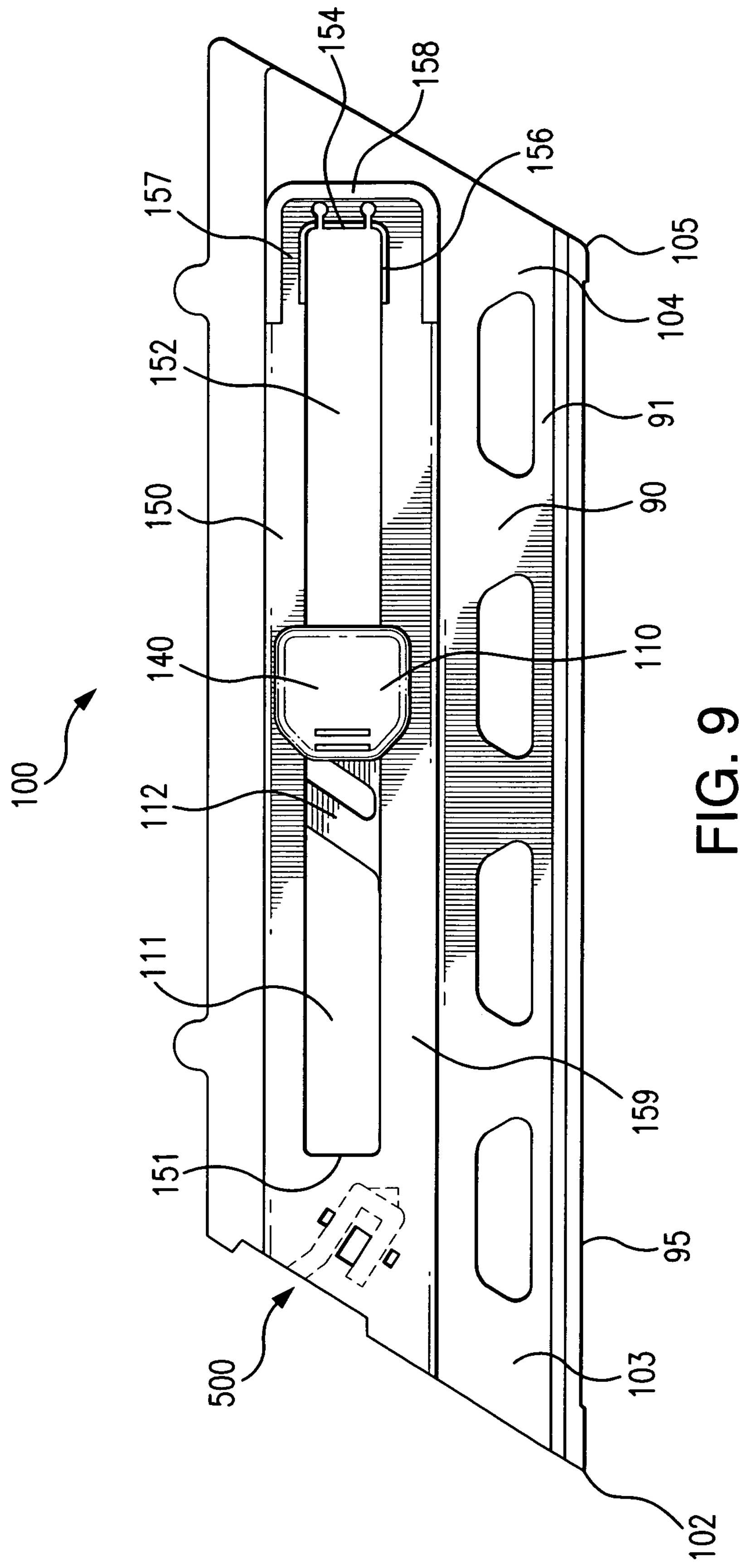
FIG. 9 is a knob-side view of a magazine illustrating a pusher assembly in an engaged state.
Figure 10B:
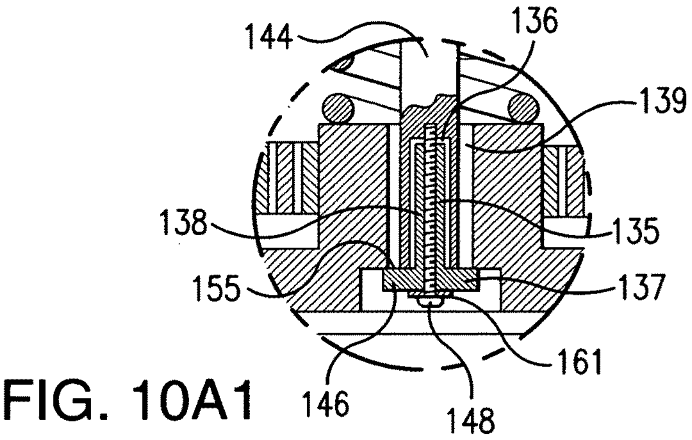
FIG. 10B is a sectional view of a pusher assembly having a pusher assembly knob reversibly fixed by a detent.
Figure 10B:
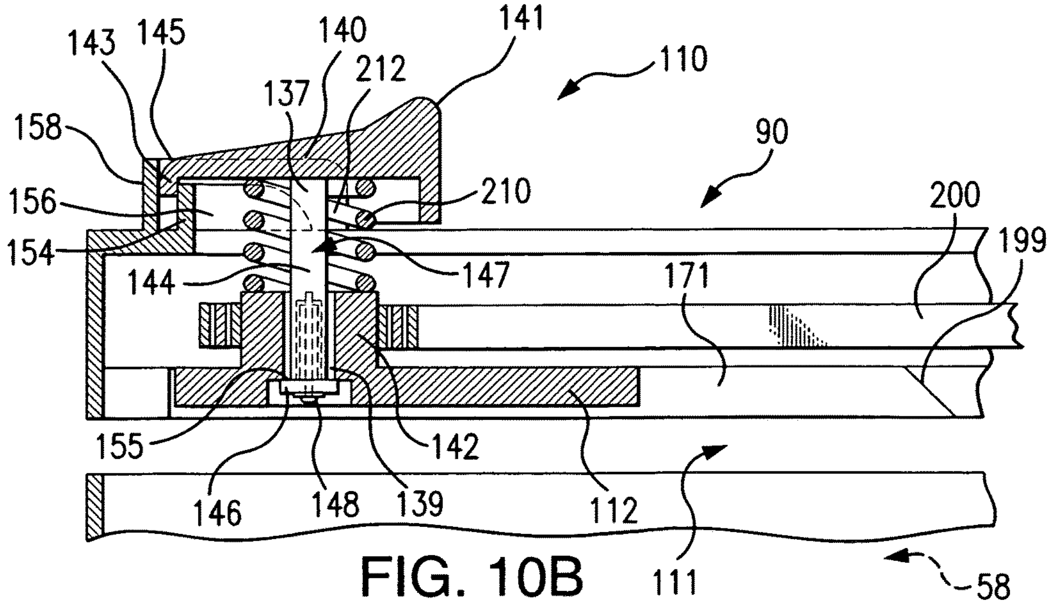
Figure 11:
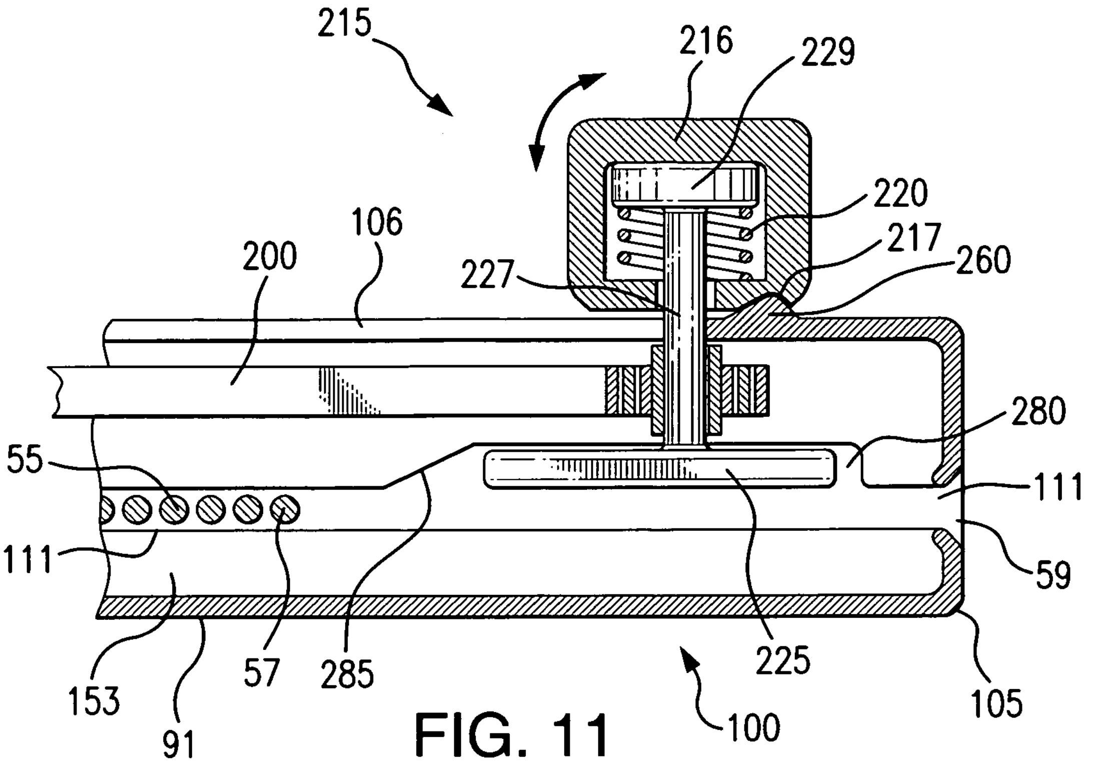
FIG. 11 is a sectional view of a pusher assembly having a pusher assembly knob having an indentation which is reversibly fixed by a detent which is reversibly mated with the indentation.
Figure 12:
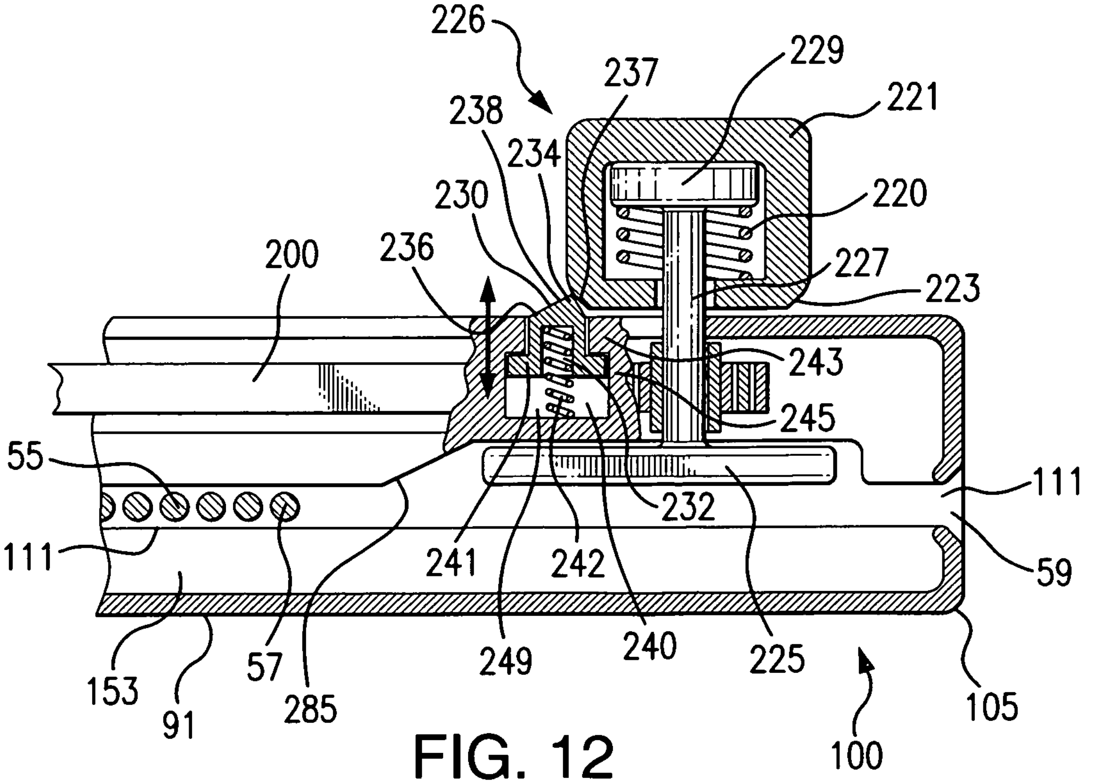
FIG. 12 is a sectional view of a pusher assembly having a pusher assembly knob reversibly fixed by a spring loaded detent.

In an embodiment, the pusher assembly 110 can be placed in an engaged state by the movement of the pusher 112 into the nail track 111 and in the direction of loading of fasteners (e.g. nails) to push the plurality of nails 55 toward the nose end 102. The pusher assembly knob 140 can be reversibly fixed in place or secured against movement out of a retracted state by a variety of means. In a non-limiting example, FIG. 11 shows the pusher assembly knob 140 reversibly fixed in place by a detent 260; FIG. 12 shows the pusher assembly knob 140 reversibly fixed in place by a spring loaded detent 230; FIG. 9 shows a detent 156 which is a U-shaped detent and FIG. 10B shows the pusher assembly knob 140 reversibly fixed in place by the detent 156. In an embodiment, the operator can accomplish reloading by using one hand to pull back the pusher assembly 110, reversibly retracting it, and reloading the magazine 100 with fasteners, and then engaging the pusher assembly 110 for fastening operation.

In another embodiment, the magazine can use a push button mechanism (or other detent or latching mechanism) instead of the pusher assembly knob 140 in pusher assembly 110.

Figure 1A:
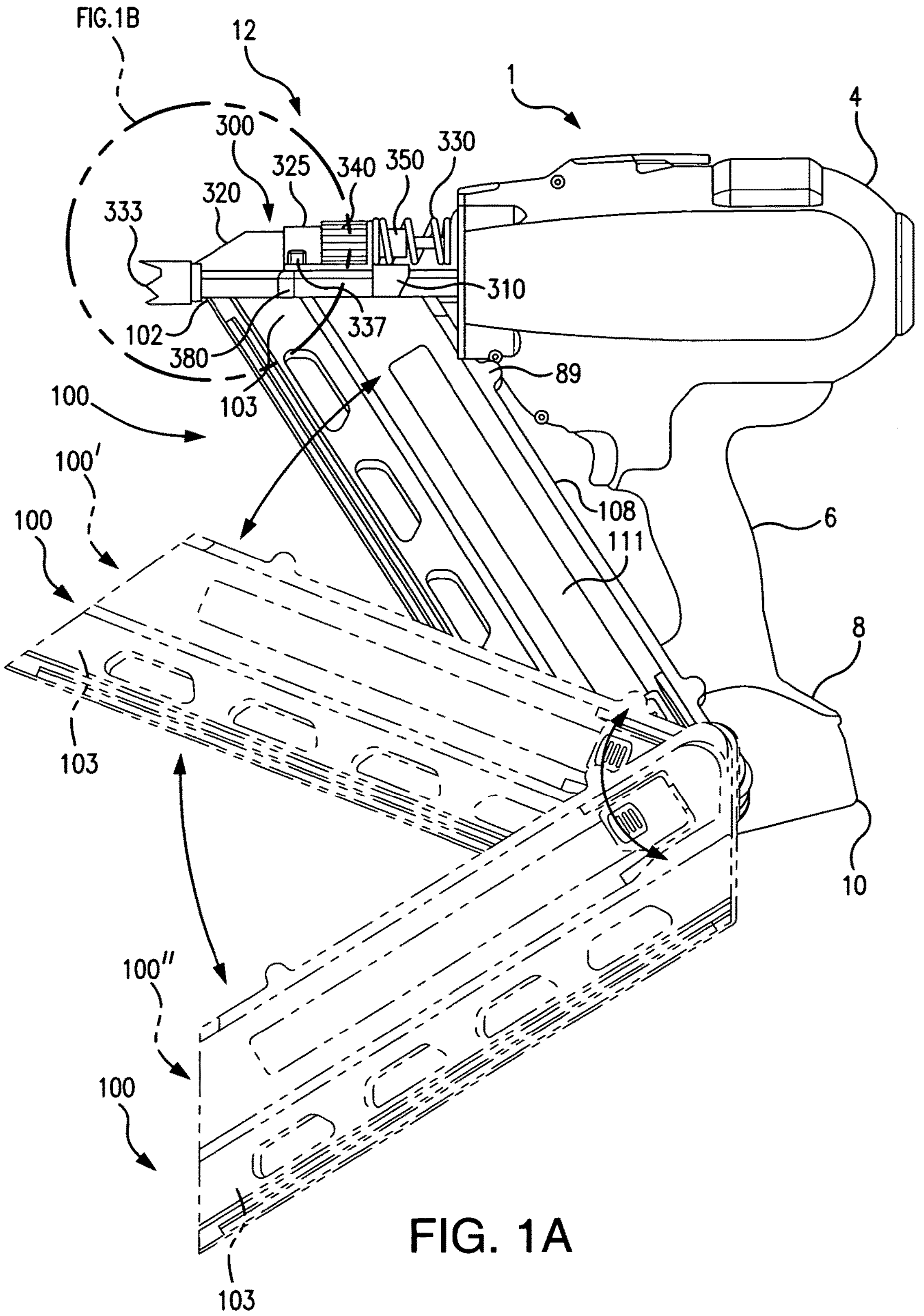
FIG. 1A is a knob-side view of an exemplary nailer illustrating an embodiment in which the magazine can reversibly pivot away from a fixed nosepiece assembly.

FIG. 1A is a knob-side view of an exemplary nailer illustrating an embodiment in which the magazine can pivot away from the fixed nosepiece assembly.

In the embodiment of FIG. 1A, the magazine 100 is pivotably attached to the power tool, for example by coupling member 88 (FIG. 2), or to handle 6, or to base 8. This disclosure is not limiting as to where on the fastening tool the magazine is attached. The means of attachment adapts the tool so that the nose portion 103 can be moved away from a nosepiece assembly 12. FIG. 1A illustrates an example embodiment in which the nosepiece assembly 12 is a fixed nosepiece assembly 300. In an embodiment, the movement away from the nose portion 103 is by a rotational motion. This feature allows for easy removal of misfired nails from the nosepiece assembly 12, ready maintenance and ease of operation.

In an embodiment, from a state where the magazine 100 is reversibly attached to the fixed nosepiece assembly 300 (e.g. FIG. 1), unscrewing one or more of a magazine screw 337 can release the magazine 100 from attachment to the fixed nosepiece assembly 300 such that the nose portion 103 can be rotationally moved away from the fixed nosepiece assembly 300 as shown in FIG. 1A by moving the magazine 100 to for example positions 100' and 100".

A range of motions are possible to move the magazine 100. Positions 100' and 100" are non-limiting examples of possible locations of the movement of the magazine 100. Additionally, the magazine 100 can be attached to nailer 1 to allow for a movement of the magazine 100 which is other than radial motion. Like reference numbers in FIG. 1 identify like elements in FIG. 1A.

Figure 1B:
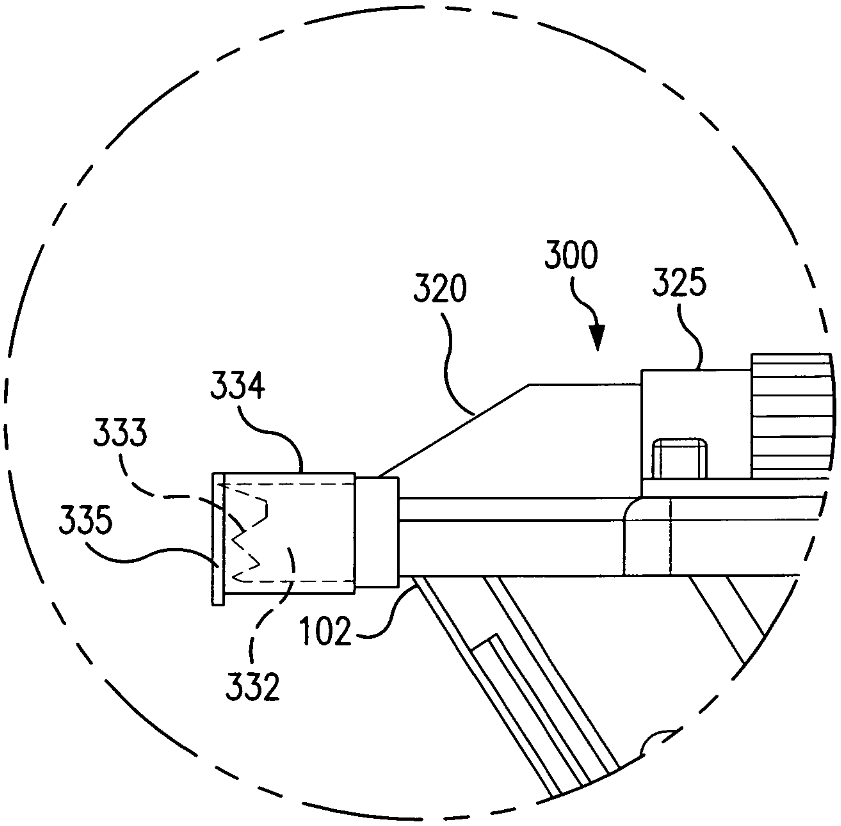
FIG. 1B is a knob-side view of a detail of a nosepiece assembly having a nose cover.

FIG. 1B is a knob-side view of an exemplary nailer illustrating a detail of a nosepiece assembly 12 having a nose cover 334. FIG. 1B illustrates an embodiment in which nose 332 can be covered by a nose cover 334 which has a no-mar pad 335. In an embodiment, the no-mar pad 335 covers the nose tip 333. Like reference numbers in FIG. 1 identify like elements in FIG. 1B.

FIG. 2 is a side view of exemplary nailer 1 having a magazine 100 and viewed from a nail-side 58. Allen wrench 600 is illustrated as reversibly secured to the magazine 100. Like reference numbers in FIG. 1 identify like elements in FIG. 2.

FIG. 2A is a detail view of the fixed nosepiece assembly 300. In an embodiment, nosepiece insert 410 having nose 400 with insert tip 355 is inserted into the fixed nosepiece assembly 300. In an embodiment, nosepiece insert 410 is configured such that a driver blade 54 overlaps at least a portion of a blade guide 415 which optionally can extend under a nose plate 331. The overlap of blade guide 415 by driver blade 54 is optional. Blade guide 415 is an optional element of the nosepiece insert 410. In an embodiment, blade guide 415 is not required in the nosepiece insert 410 and can be absent from the nosepiece insert 410. Nose 332 is also illustrated.

Nosepiece insert 410 can be secured to the fixed nosepiece assembly 300 by one or more of a nosepiece insert screw 401 through a respective insert screw hole 422. In an embodiment, the nosepiece insert 410 can be investment cast. In an embodiment, nosepiece insert 410 can be made of a light weight material such as aluminum. In another embodiment, the nosepiece insert 410 can be investment cast steel. In an embodiment, the insert can be made at least in part from 8620 carbonized steel, which can optionally be investment cast 8620 carbonized steel.

In an embodiment, the nosepiece insert 410 is joined to the fixed nosepiece assembly 300 by a nail guide insert screw 421 through a rear mount screw hole 417. Optionally, one or more prongs 437 respectively having a screw hole 336 for the magazine screw 337 can be used. In an embodiment, the nosepiece insert 410 accommodates at least one or more prongs 437.

FIG. 2A also illustrates a nose plate 331 having a switch activation rod hole 402 through which an activation rod 403 (e.g. FIG. 15I) passes. Housing 4 is shown in conjunction with the nose plate 331.

FIG. 2B is a detailed view of a nosepiece insert 410 viewed from the channel side 412.

FIG. 2B illustrates nosepiece insert 410 which has a channel side 412 with a nose 400 and insert tip 355. The channel side 412 has a blade guide 415 and a nail stop 420. In an embodiment, the nail stop 420 can be in line with said plurality of nails (FIG. 2C1). In an embodiment angle G can be 14 degrees. In an embodiment, the nail stop 420 having nail stop centerline 427 (FIG. 2B) is offset from the insert centerline 423 which achieves the receipt of nails to the nail stop 420 in a configuration in which the longitudinal axis 1127 of the plurality of nails 55 (FIG. 2C2A) is collinear (or parallel in alignment) with the longitudinal centerline 1027 of the nail track 111. The nosepiece insert 410 can also have a rear mount screw hole 417 and one or more of an interface seat 425. FIG. 2B also illustrates the insert screw hole 422 which can secure nosepiece insert 410 into the fixed nosepiece assembly 300.

In an embodiment, nail stop 420 can have a dimension such that a nail will not have contact with the nail stop 420 after 10 percent of the length of the nail has been driven. For example a 90 mm nail would not be in contact with nail stop 420 after 9 mm of the nail has been driven. The nail stop 420 length can be set to 10 percent of the length of the loaded nail 53 (e.g. FIG. 2E) to be driven. In another embodiment, the nail stop 420 length is 25 percent the length of the nail. In yet another embodiment the nail stop 420 is a value in a range of from 10 percent to 90 percent of the length of the nail, for example 15 percent or 33 percent, or 50 percent.

The nail stop 420 length can broadly vary in design. An embodiment has a nail stop which is shorter in length than the length of a loaded nail (e.g. loaded nail 53; or a nail of the plurality of nails 55) to be driven. In an embodiment, the magazine can be used with nails having different lengths and the nail stop 420 can be shorter then the length of the shortest nail used with the magazine of such embodiment.

In an embodiment, the magazine 100 and the nosepiece assembly 12 can adapted for a collation angle of a plurality of nails 55 which is greater than the angle of the magazine.

Figure 2D:
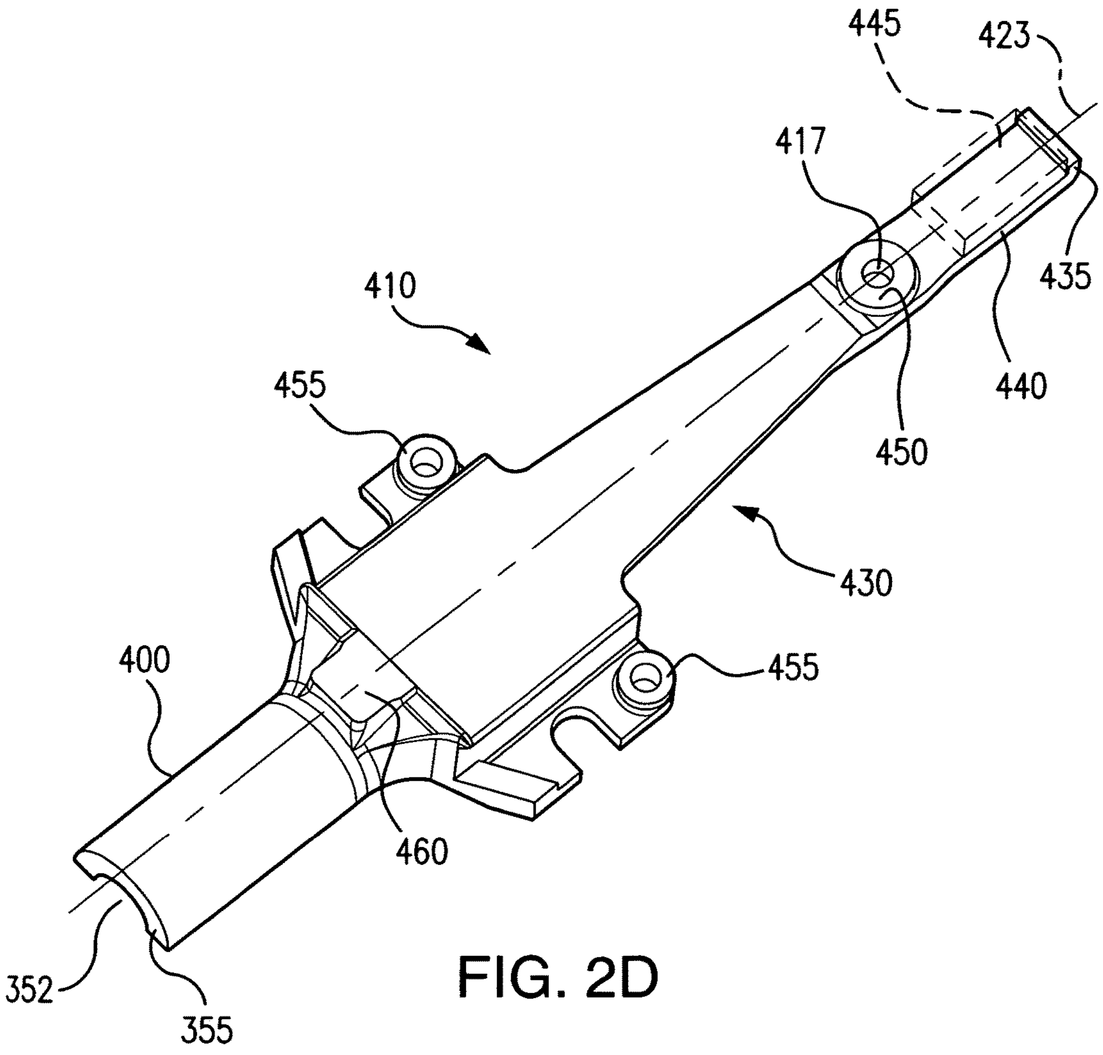
FIG. 2D is a detailed view of a nosepiece insert viewed from the fitting side.

In an embodiment, a nail channel 352 is formed when the nosepiece insert 410 is mated with the nose end 102 of the magazine 100 (e.g. FIG. 2B and FIG. 2D). The formation of the nail channel 352 provides a generally cylindrical path for a nail which is being driven. When the nosepiece insert 410 is mated with the nose end 102 of the magazine 100, the nail channel has an inner circumference.

In an embodiment, about 50 percent of the inner circumference can be provided by the nosepiece insert 410 and about 50 percent of the inner circumference is provided by the nose end 102. Broad variance can be used regarding which pieces provide which percentages of the inner circumference of the nail channel 352. This disclosure should be broadly construed in this regard.

In an embodiment, nosepiece insert 410 can constitute 50 percent of the inner circumference of nail channel 352. In another embodiment nosepiece insert 410 can constitute less than 50 percent of the inner circumference of nail channel 352. In another embodiment nosepiece insert 410 can constitute greater than 50 percent of the inner circumference of nail channel 352. FIG. 2B also illustrates insert centerline 423 and nailer 1 channel centerline 429 (FIG. 2C2A) perpendicular thereto. As illustrated in FIG. 1A the fixed nosepiece 300 mates with the nose end 102 of the magazine 100. When nosepiece 300 and the nose end 102 are coupled, channel centerline 429 can be collinear or parallel with nailer 1 centerline 1029.

FIG. 2C1 is a detailed view of a nosepiece insert section 2C1 of FIG. 2B. FIG. 2C1 illustrates a cross-sectional detail of the nail stop 420 which is offset from the insert centerline 423 (FIG. 2). The location of the nail stop 420 can be set such that a portion of a nail can contact the nail stop 420. The location of the nail stop 420 to achieve this orientation can be dependent upon the orientation of the magazine 100. Nail stop centerline 427 can be offset in FIG. 2C 1 at an angle G measured from nailer 1 channel centerline 429 (FIG. 2C2A).

FIG. 2C2 is a detailed view of a nosepiece insert having nail stop 420 offset at an angle G measured from the channel centerline 429 (e.g. FIG. 2B). In an embodiment, angle G aligns the longitudinal centerline 1027 of the nail track 111 with the centerline 1127 of the plurality of nails 55 and also nail stop centerline 427.

FIG. 2C2A is a perspective view illustrating the alignment of an embodiment of a nailer 1, a magazine 100, a plurality of nails 55 and a nail stop 420. FIG. 2C2A illustrates the nail stop 420, the nail stop centerline 427, a longitudinal centerline 927 of the magazine 100, a longitudinal centerline 1027 of the nail track 111, a longitudinal centerline 1127 of the plurality of nails 55 and a longitudinal centerline 1227 of the nailer 1. FIG. 2C2A illustrates that in an embodiment having fixed nosepiece 300 having nosepiece insert 410 is mated with the nose end 102 channel centerline 429 can be collinear with nail 1 centerline 1029. Like reference numbers in FIG. 1 identify like elements in FIG. 2C2A.

In an embodiment, the magazine 100 can have its longitudinal centerline 927 offset from a longitudinal centerline 1227 of nailer 1 by an angle G. Angle G can be 14 degrees. In an embodiment, nail stop centerline 427 can be collinear with a longitudinal centerline 927 of the magazine 100. Additionally, in an embodiment, longitudinal centerline 927 of the magazine 100 can be collinear with a longitudinal centerline 1027 of the nail track 111, as well as collinear with a nail stop centerline 427. Longitudinal centerline 1127 of the plurality of nails 55 can be collinear with nail stop centerline 427. A wide range of angles and orientations for the nail stop 420 can be used.

FIG. 2D is a detailed view of the nosepiece insert 410 viewed from the fitting side 430. Optionally, the fitting side 430 can have a magnet stop 435 and a magnet seat 440 which are adapted for the mounting of a magnet 445.

Magnet 445 can be mounted on the fitting side 430 by a variety of means including frictional fit (e.g. in which the magnet is fit between the magnet stop 435 and the magnet seat 440), by magnetic attraction of magnet 445 to the insert 410, structural fit, by adhesive, fastener, or other mounting and/or fastening means. In another embodiment, at least a portion of insert 410 can have magnetic properties. A magnetic portion of insert 410 can be used to guide driver blade 54. Like reference numbers in FIG. 2B identify like elements in FIG. 2D.

The fitting side 430 can have a rear mount 450 and a rear mount screw hole 417 to receive a screw to secure nosepiece insert 410 to the fixed nosepiece assembly 300. The fitting side 430 can also have a mount 455 to receive a screw to secure nosepiece insert 410 to the fixed nosepiece assembly 300. The fitting side 430 can have lower trip seat 460 which fits into a portion of nosepiece assembly 300. Like reference numbers in FIG. 2B identify like elements in FIG. 2D.

Figure 2E:
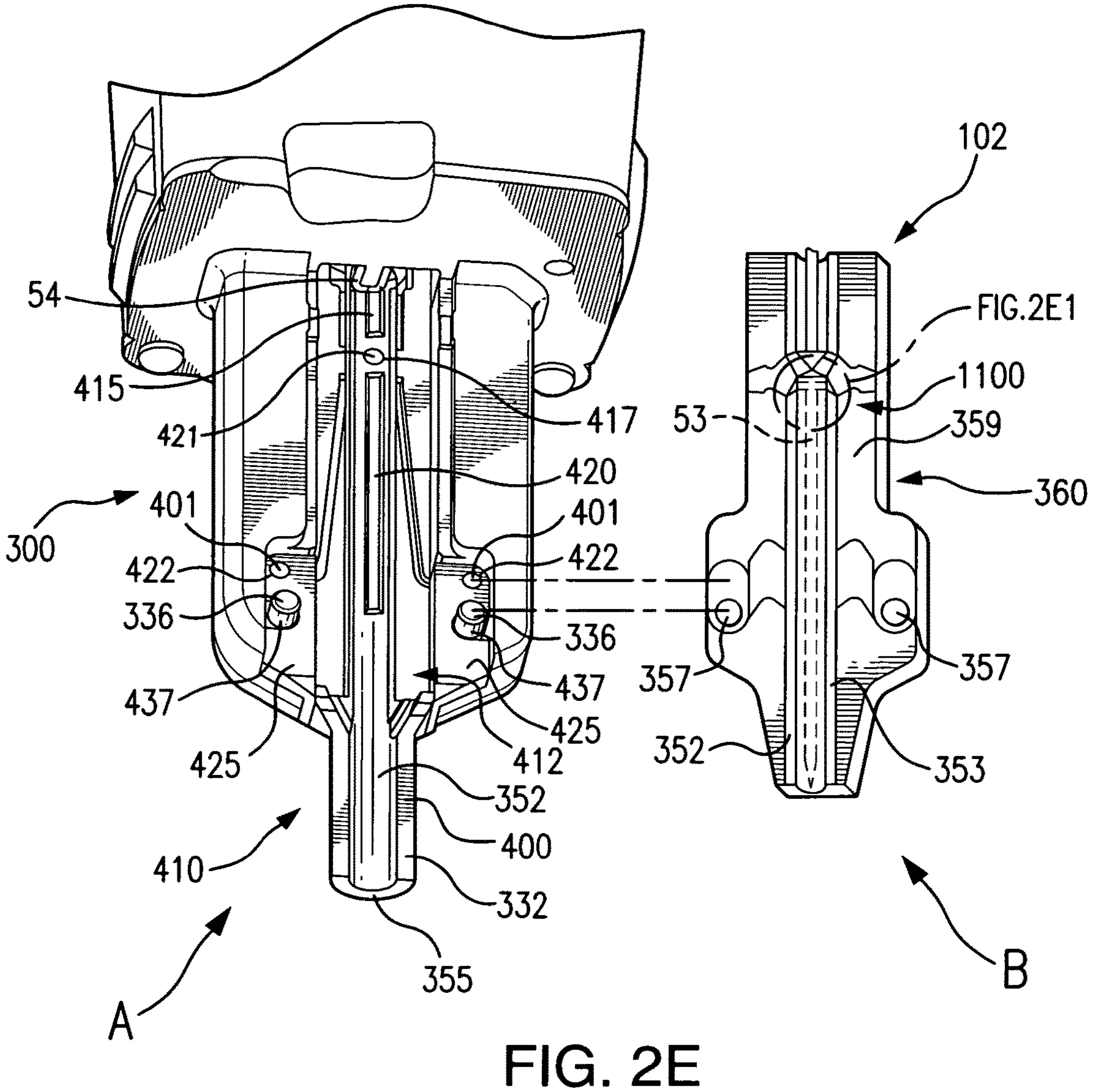
FIG. 2E is a detailed view of a fixed nosepiece with a nosepiece insert and a mating nose end of a magazine (which can mate as illustrated in FIG. 1A)

As illustrated in FIG. 2E, the nosepiece insert 410 and the nose end 102 of the magazine 100 can be reversibly fit together by a fastening means. In an embodiment, at least a magazine screw 337 can be turned to reversibly fit nosepiece insert 410 and the nose end 102 together. The nail channel 352 can be formed by fitting nosepiece insert 410 and the nose end 102 together. Like reference numbers in FIG. 2A identify like elements in FIG. 2E.

FIG. 2E is a detailed view of a fixed nosepiece with a nosepiece insert and a mating nose end of a magazine (which can mate as illustrated in FIG. 1A). FIG. 2E is a detailed view of the nosepiece assembly 300 from the channel side 412 which mates with the nose end 102 of the magazine 100. See FIG. 1A for an example of a motion of the magazine 100 which can achieve mating of the nose end 102 and the magazine 100.

FIG. 2E detail A illustrates a detail of the nosepiece insert 410 from the channel side 412. As illustrated, the nosepiece insert 410 has the rear mount screw hole 417 for the nail guide insert screw 421. The nail guide insert screw 421 can be a rear mounted or front mounted screw. Nosepiece insert 410 can also have a blade guide 415 and nail stop 420. Nosepiece insert 410 can be fit to nosepiece assembly 300 and can have an interface seat 425. Nosepiece insert 410 can also have a nosepiece insert screw hole 422 and a magazine screw hole 336. Optionally, insert screw 401 for mounting the nosepiece insert 410 to the fixed nosepiece assembly 300 can be a rear mounted screw or a front mounted screw. Like reference numbers in FIG. 2A identify like elements in FIG. 2E.

FIG. 2E detail B is a front detail of the face of the nose end 102 having nose end front side 360. The nose end 102 can have a nose end front face 359 which fits with channel side 412. The nose end 102 can have a nail track exit 353. For example, a loaded nail 53 is illustrated exiting nail track exit 353. FIG. 2E detail B also illustrates screw hole 357 for magazine screw 337.

FIG. 2E1 is a detailed view of a nail feed funnel 1100. In an embodiment, nail feed funnel 1100 can have an opening from which the loaded nail 53 emerges from nail track exit 353 of the magazine 100 and is fed into nail channel 352. Nail feed funnel 1100 can have one or more feed surfaces (e.g. 1103 and 1104) along which a nail head 1130 can slide. In an embodiment, a feed plane 1199 can be coplanar with one or more feed surfaces. In the embodiment illustrated in FIG. 2E1 a first feed surface 1103 and a second feed surface 1104 are coplanar. In this example, a feed plane 1199 is illustrated as also coplanar with 1103 and 1104.

The nail feed funnel 1100 can have a first feed surface 1103 and a second feed surface 1104 and can be at least a part of a transition portion from which a nail 53 emerges from nail track exit 353 and enters into nail channel 352. FIG. 2E1 illustrates the nail feed funnel 1100 having first feed guide 1101 and second feed guide 1102.

First feed guide 1101 can have inner edge 1111 and end edge 1110, as well as track edge 1112 and top edge 1113. Track edge 1112 and top edge 1113 can be connected by funnel edge 1114 which can extend between inner funnel point 1150 and outer funnel point 1155.

Second feed guide 1102 can have inner edge 1116 and end edge 1115, as well as track edge 1117 and top edge 1118. Track edge 1117 and top edge 1118 can be connected by funnel edge 1119 which can extend between inner funnel point 1160 and outer funnel point 1165.

A nail feed funnel 1100 can be constructed of a wide range of geometries and contain a broad variety of elements. The shape of a nail feed funnel 1100 can vary broadly. The nail feed funnel 1100 can have one or more of a curved surface, a flat surface, a notched surface, an angled surface, a textured surface, a coated surface, a non-stick surface or other surface type. Nail feed funnel 1100 can have two or more of the same type of surface, or a combination of surface types. In an example, as illustrated in FIG. 2E1 first feed surface 1103 and a second feed surface 1104 each have a generally flat surface and are generally planar with one another. In another embodiment first feed surface 1103 and second feed surface 1104 can be ridged or notched to fit with an outer diameter of a nail head.

A first head guide surface 1105 and second head guide surface 1106 are illustrated in FIG. 2E1. Each of first head guide surface 1105 and second head guide surface 1106 can be a surface along which at least a portion of a nail head can slide or be guided as a nail is driven. First head guide surface 1105 and second head guide surface 1106 can be each generally flat in shape. In another embodiment first head guide surface 1105 and second head guide surface 1106 can be ridged, or notched, or otherwise shaped, to fit with an outer circumference of a nail head. First head guide surface 1105 and second head guide surface 1106 can have similar or different shapes and surfaces.

As illustrated in FIG. 2E1, the funnel can have an angle R1. Angle R1 can be the angle between end edge 1110 and top edge 1113. This angle can have a wide range of values. Angle R1 for example can be a value in a range of from less than 90° to 175°. In an embodiment, Angle R1 can be 90°. In another embodiment angle R1 can be 130°. In another embodiment angle R1 can be 145°. FIG. 2E1 illustrates angle R1 can be 165°. Angle R3 can be the angle between end edge 1115 and top edge 1118. Similarly, angle R3 can also have a values disclosed herein for angle R1 (e.g. a value in a range of from less than 90° to 175°, 130°, 145°, or 165°). FIG. 2E1 illustrates angle R3 can be 165°.

As illustrated in FIG. 2E1, the funnel can have an angle R2. Angle R2 can be the angle between funnel edge 1114 and top edge 1113. This angle can have a wide range of values. Angle R2 for example can be a value in a range of from less than 90° to greater than 150°. In an embodiment, Angle R2 can be 90°. In another embodiment R2 can be 60°. In another embodiment R2 can be 30°. FIG. 2E1 illustrates angle R2 can be 35°. Angle R4 can be the angle between funnel edge 1119 and top edge 1118. Similarly, angle R4 can have the values disclosed herein for angle R2 (e.g. a value in a range of from less than 90° to greater than 150°, 90°, 60°, 35° or 30°). FIG. 2E1 illustrates angle R4 can be 35°.

When an angle R1 and/or an angle R3 has a value greater than 90°, the nail feed funnel 1100 can be referred to as a ramped nail feed funnel. FIG. 2E1 illustrates a nail feed funnel 1100 which is a ramped nail feed funnel in which R1 can have a value of 165° and R3 can have a value of 165°.

In an embodiment, the a ramped feed funnel having an angle R1 and/or an angle R3 has funnel surfaces and features which can be inspected by automated inspection equipment, e.g. optical, or mechanical inspection.

In an embodiment, the exit of a nail to be driven from nail track exit 353 via nail feed funnel 1100 can position the nail head in relation to driver blade 54 to reduce skipping, buckling and bending of loaded nail 53 when it is driven. In an embodiment, the nail head is located less than 30 mm (e.g. 20 mm or 15 mm), from the closest portion of driver blade 54. In another embodiment, the nail head is located 10 mm or less, or 5 mm or less, from the closest portion of driver blade 54.

In an embodiment, the nail feed funnel 1100 can be cast of a metal. In non-limiting example the nail feed funnel 1100 can be cast of a light weight material such as aluminum, or the nail feed funnel 1100 can be investment cast steel. In an embodiment, the nail feed funnel 1100 can be 8620 carbonized steel.

The disclosure herein also encompasses a means for guiding a nail for and during driving in nailer 1, which in an example uses a fixed nosepiece 300 having a nosepiece insert 410 in a nosepiece 12. Such means also can include a broad variety of nail stops, channel designs having geometries providing equivalent control to nail movement as the nosepiece insert 410, variations on the nosepiece 12 which have one piece nail channels and which incorporate aspects of the nose end 102 of magazine 100. Additionally, means for guiding a nails for and during driving in nailer 1 can include a broad variety of funnel designs and mechanisms for providing a nail 57 in an orientation for proper driving by a driver blade 54. Such mean can include a funnel which is contained within the nosepiece or which is part of a nosepiece insert.

This disclosure also encompasses the methods for feeding a nail 57 to a driver blade 54 using the elements, equivalents and means disclosed herein.

FIG. 3 is a side view of another embodiment of exemplary nailer 1 viewed from the knob-side 90 and having a magazine 100 showing the pusher assembly 110 having a pusher assembly knob 140. In this embodiment, the nosepiece assembly 12 is a latched nosepiece assembly 13. Also in this embodiment, the magazine 100 is coupled to the housing 4 and coupled to the base 8 of the handle 6 by bracket 11. Like reference numbers in FIG. 1 identify like elements in FIG. 3.

Figure 4:
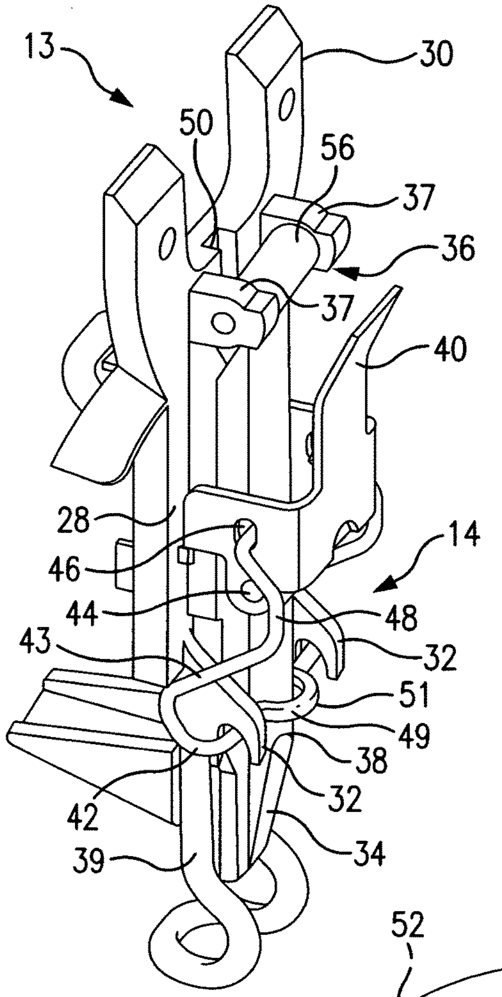
FIG. 4 is a perspective view of a latched nosepiece assembly of the nailer having a latch mechanism used with a magazine.

FIG. 4 is a perspective view of latched nosepiece assembly 13 of nailer 1 having a latch mechanism 14 and which can be used with the magazine 100.

Latched nosepiece assembly 13 has a nosepiece 28 which is mounted to a backbone structure of housing 4 (FIG. 1). Nosepiece 28 has a pair of hooks 32 that extend therefrom in a direction away from the magazine 100. In an embodiment, a nose cover 34 can be pivotally mounted to the nosepiece 28 near an end 30 by a pin connection 36 extending between a pair of lugs 37. Nosepiece 28 further has a groove 50 and the nose cover 34 has a cam portion 56.

The nose cover 34 can extend along the length of the nosepiece 28 between the hooks 32. The nose cover 34 has a rib 38 that extends along its length. Rib 38 can be used to provide strength to the nose cover 34 and a line-of-sight for the operator of the nailer 1 to align the nails. The nosepiece 28 and nose cover 34 define a channel 52 (e.g. FIG. 6) which is a passage through which a nail can pass. FIG. 4 also illustrates an embodiment having a tip portion 39 which can contact a workpiece.

The latch mechanism 14 is mounted to the nose cover 34 and has a latch tab 40 and a latch wire 42. The latch mechanism 14 can be used to lock and unlock the nose cover 34 to and from nosepiece 28. The latch tab 40 is pivotally connected to the nose cover 34 at pin 44. Latch wire 42 is pivotally coupled to latch tab 40 at slots 46. In an embodiment, the latch wire 42 can be formed such that a center portion 49 of latch wire 42 has a hump portion 51 sized to fit over the rib 38 (FIG. 2). The latch wire 42 has a pair of parallel arms 48 which can be perpendicular to a center portion 49 of latch wire 42. Various shapes of the arms 48 can be employed. The latch wire can have at least an arm 43 which can have a sinusoidal, or "S" shape as illustrated in e.g. FIGS. 4 and 6.

Figure 5:
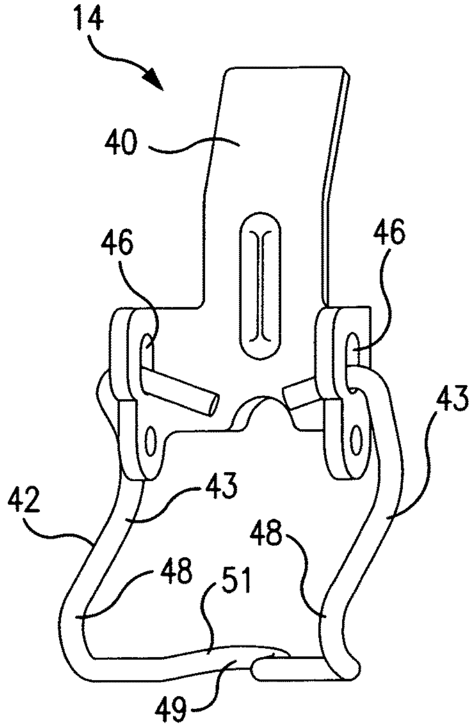
FIG. 5 is a perspective view of a latch wire and latch tab used with a latch mechanism.

FIG. 5 is a rear perspective view of a latch wire and latch tab used with the latch mechanism 14. The latch wire 42 is pivotally coupled to the latch tab 40 at slots 46. Slots 46 can be sized to allow for securing and release of the latch wire 42 by the operation of latch tab 40. Like reference numbers in FIG. 4 identify like elements in FIG. 5.

With reference to FIGS. 4 and 5, when the nose cover 34 is in its locked position over the nosepiece 28, the latch wire 42 is locked firmly within the hooks 32 of the nosepiece 28. The center portion 49 in turn presses firmly down upon the nose cover 34 on each side of the rib 38. This ensures that nose cover 34 is tightly engaged to nosepiece 28. To unlock nose cover 34, the latch tab 40 can be urged away from nose cover 34. This in turn disengages the latch wire 42 from the hooks 32, thus allowing the nose cover 34 to pivot about pin connection 36 away from the nosepiece 28. In the unlocked position, an operator can then clear any nail jams within the nosepiece assembly 12.

FIG. 6 is a side view of the latched nosepiece assembly 13 and the nose portion 103 of the magazine 100 having the nose end 102. FIG. 6 illustrates a driver blade 54 and the pusher assembly 110 having the pusher 112 used with the magazine 100 of nailer 1 and pushing on a nail 57 of the plurality of nails 55. The nosepiece 28 has a groove 50 formed therein that cooperates with the nose cover 34 to form a channel 52 (channel is generally cylindrical when the nose cover 34 is in its locked position) (e.g., FIG. 7 and FIG. 8). The channel 52 is sized to receive a loaded nail 53 pushed into it from the magazine 100. The driver blade 54 extends from the housing 4 into channel 52. The driver blade 54 is driven by the motor and nail driver mechanism (not shown) and engages the head of the loaded nail 53 to drive the loaded nail 53 through the nosepiece 28 and out of the nailer 1. In an embodiment, the driver blade is a crescent shaped driver blade.

When the nose cover 34 is in its unlocked position (shown in dashed lines in FIG. 6), to prevent escape of driver blade 54 from the nosepiece 28, nose cover 34 has a cam portion 56. As the nose cover 34 is moved to its unlocked position, the cam portion 56 engages the driver blade 54, thereby constraining the driver blade 54 to the groove 50 and preventing the driver blade 54 from escaping. Like reference numbers in FIG. 4 and FIG. 5 identify like elements in FIG. 6.

Figure 7:
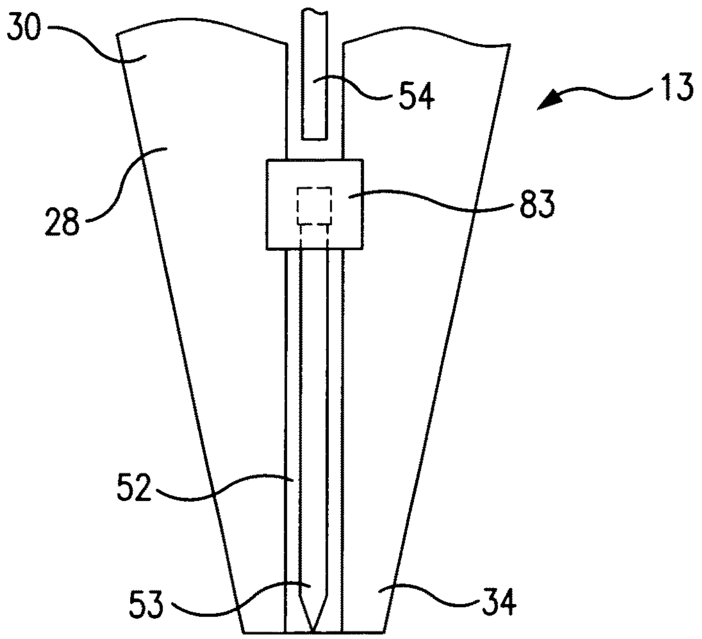
FIG. 7 is a view of the nosepiece of the latched nosepiece assembly having a nail stop bridge.

FIG. 7, illustrates a cross section of channel 52 of latched nosepiece assembly 13 (and a nose-on view of nosepiece 28) having a loaded nail 53 in place for driving by driver blade 54.

FIG. 7 further illustrates end 30 and nose cover 34 of nosepiece 28. In this embodiment, the nosepiece 28 also includes a nail stop bridge 83 which bridges the channel 52. The nail stop bridge 83, or a nail stop, can stop each nail of the plurality of nails 55 as they are pushed by the pusher 112 into channel 52. This assures that the head of the loaded nail 53 within the channel 52 is aligned with the driver blade 54. The nail stop bridge 83 also prevents buckling of a loaded nail 53, which can occur as the driver blade 54 strikes the loaded nail 53. In an embodiment, the nail stop bridge 83 is formed as part of the nosepiece 28 and optionally can be of a single unitary structure.

Figure 8:
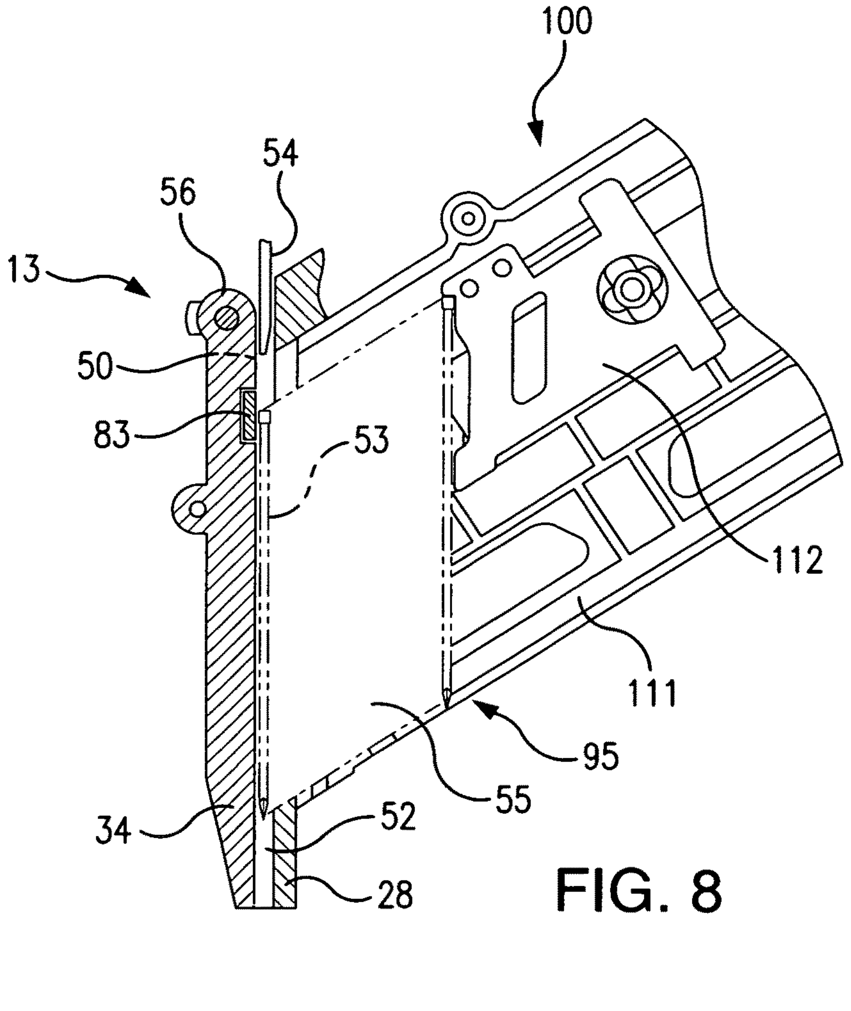
FIG. 8 is a side sectional view of the latched nosepiece assembly having a nail stop bridge.

FIG. 8 is a side sectional view of the latched nosepiece assembly 13 illustrating a nail stop bridge 83 used. In an example embodiment, channel 52 can be formed from two or more pieces, e.g. nose cover 34 and at least one of groove 50 and nosepiece 28 (and/or nail stop bridge 83).

Nosepiece 28 has a groove 50 (FIG. 4) formed therein which cooperates with the nose cover 34 (when the nose cover 34 is in its locked position). The locking of nose cover 34 against groove 50 can form an upper portion of channel 52. The driver blade 54 can extend from housing 4 into channel 52. The driver blade 54 can engage the head of the loaded nail 53 to drive loaded nail 53. Cam 56 prevents escape of driver blade 54 from the nosepiece 28.

Nosepiece 28 further has a nail stop bridge 83 that bridges the channel 52. The nail stop bridge 83 engages each nail of the plurality of nails 55 as they are pushed by the pusher 112 along the nail track 111 of the magazine 100 and into channel 52. The tips of the plurality of nails 55 can be supported by the lower liner 95, or a lower support. In an embodiment, the lower liner 95 forms part of the magazine 100.

FIG. 9 is a side view of the magazine 100 viewed from the knob-side 90 showing the pusher assembly 110 in an engaged state. FIG. 9 illustrates the pusher assembly knob 140 and a partial view of the pusher 112 as seen through the guide path opening 152 of the pusher assembly guide path 150. A spring 200 (e.g. FIG. 10A) biases the pusher 112 in a direction from the base end 105 to the nose end 102 of the magazine 100. In an embodiment, the spring 200 is a constant force spring. However, this disclosure is not limited regarding the means of biasing the pusher 112. This disclosure is also not limited as to a spring type (or motive force) for biasing the pusher 112. In an embodiment, the pusher assembly 110 can receive a motive force from a mechanism other than a spring and no spring 200 is used. The means to apply motive force on the pusher 112 can vary broadly and this disclosure is to be broadly construed in this regard.

The pusher assembly guide path 150 has a pusher track nose end 151 which is proximate to the nose portion 103 of the magazine 100 and a pusher track base end 157 which is proximate to base portion 104 of the magazine 100.

In an embodiment, the pusher assembly knob 140 can be moved such that the pusher assembly 110 is in a retracted state. When the pusher assembly 110 is in a retracted state, the pusher assembly knob 140 can interact with and can be held in place proximate to the pusher track base end 157 by a detent 156 with a detent base end 154. The detent base end 154 can have a stop 158 that stops the pusher assembly knob 140 being moved in a manner which can impart unacceptable stress on the pusher assembly 110 when being placed in a retracted stated. As such, the stop 158 can prevent mechanical damage to the pusher assembly 110 when an operator moves the pusher assembly knob 140 such that it is engaged with the detent. In an embodiment, a detent can be an integral portion of a magazine 100 (e.g. FIGS. 9-10H). In another embodiment, the detent can be a separate member interacting with both the magazine 100 and pusher assembly 110.

In a further embodiment, the detent base end 154 can be a spring member or a spring biased member that can be deflected when the pusher assembly 110 is being placed in, or moved into, a retracted state. In an embodiment, the spring member or spring biased member can be deflected in a direction away from the pusher assembly knob 140, or the knob base end 143. In another embodiment, the detent base end 154 can be moved toward or into the guide frame inside portion 153, e.g. downwardly away from a portion of the pusher assembly knob 140, to allow a portion of assembly knob 140, e.g. the knob base end 143 to move past and optionally latch to the detent base end 154.

The pusher assembly knob 140 of the pusher assembly 110 is located adjacent to a knob-side of pusher guide frame 159. The pusher assembly 110 has a connecting mechanism (e.g. FIG. 10A) which is attached to the pusher assembly knob 140 and which is connected to the pusher 112.

The pusher guide frame 159 has a guide frame inside portion 153 (e.g. FIG. 13) and a guide frame outside portion 91 (e.g. FIG. 9 and FIGS. 11-12). The nail track 111 is located in the guide frame inside portion 153. The nail track 111 extends from the nail feed slot 59 (e.g. FIGS. 11-12) located at the base end 105 to the nose end 102 of magazine 100 and extends through the guide frame inside portion 153. The pusher assembly 110 is configured such that the pusher 112 in both its retracted state and its engaged state is located within the guide frame inside portion 153.

When the pusher assembly 110 is in a retracted state, a plurality of nails 55 can be inserted into the magazine via the nail track 111. In an embodiment, the plurality of nails 55 can have tips which are supported by the lower liner 95. If the plurality of nails 55 are inserted in the magazine 100 to a location past the pusher 112 in the direction of the nose end 102 the pusher assembly 110 can be released to move and/or can be moved from a retracted state to an engaged state. The pusher assembly 110 in the engaged state can push against one of the plurality of nails 55. The spring 200, which is biased toward the nose end 102, can impart a force pushing the nails toward the nose end 102 and allowing the nails to move along the nail track 111 toward and for feeding into the nosepiece assembly 12. The pusher assembly 110 can move along the upper pusher guide 162 and lower pusher guide 170 (e.g. FIG. 13) and move the plurality of nails 55 along the nail track 111 in a direction away from the magazine base end toward the magazine nose end and push one or more of the plurality of nails 55 into the nosepiece assembly 12 for nailing.

Figure 13:
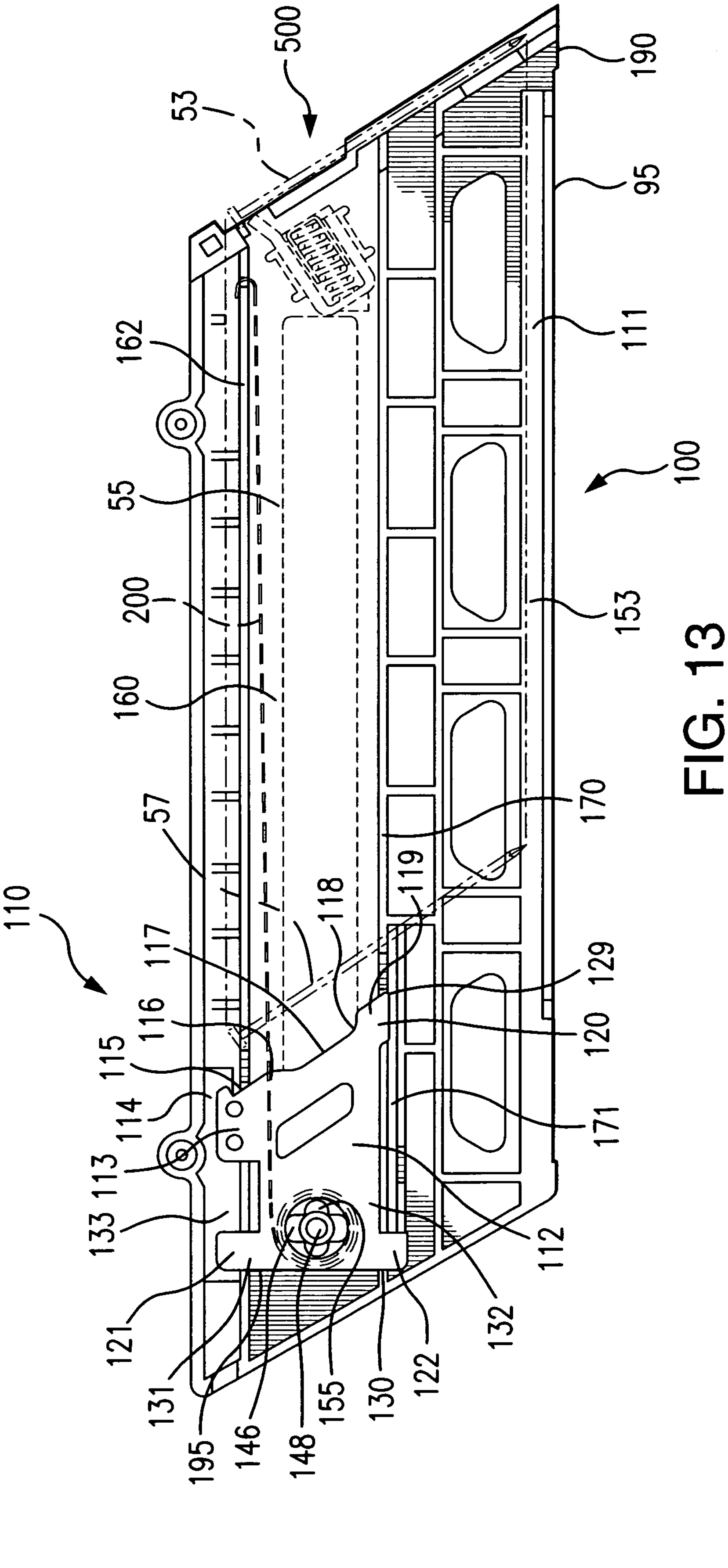
FIG. 13 is a nail-side sectional view of the magazine illustrating the pusher in a retracted state and the magazine loaded with nails.
Figure 14A:
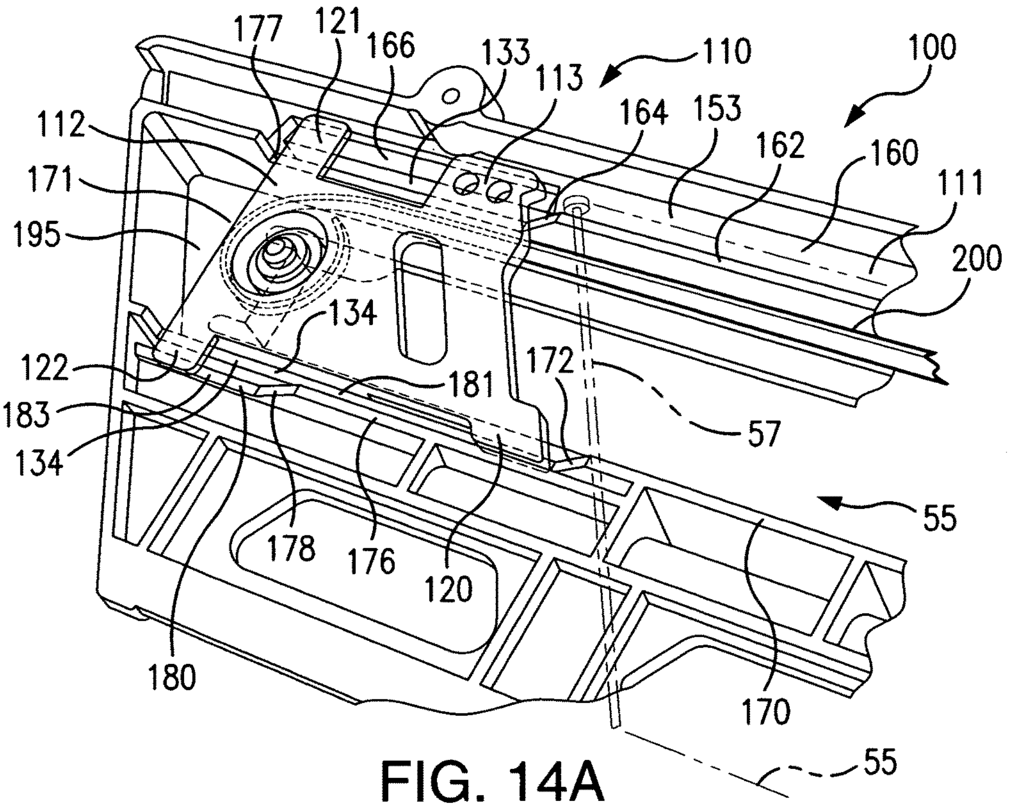
FIG. 14A is a nail-side sectional view of the magazine illustrating the pusher in a retracted state.
Figure 14B:
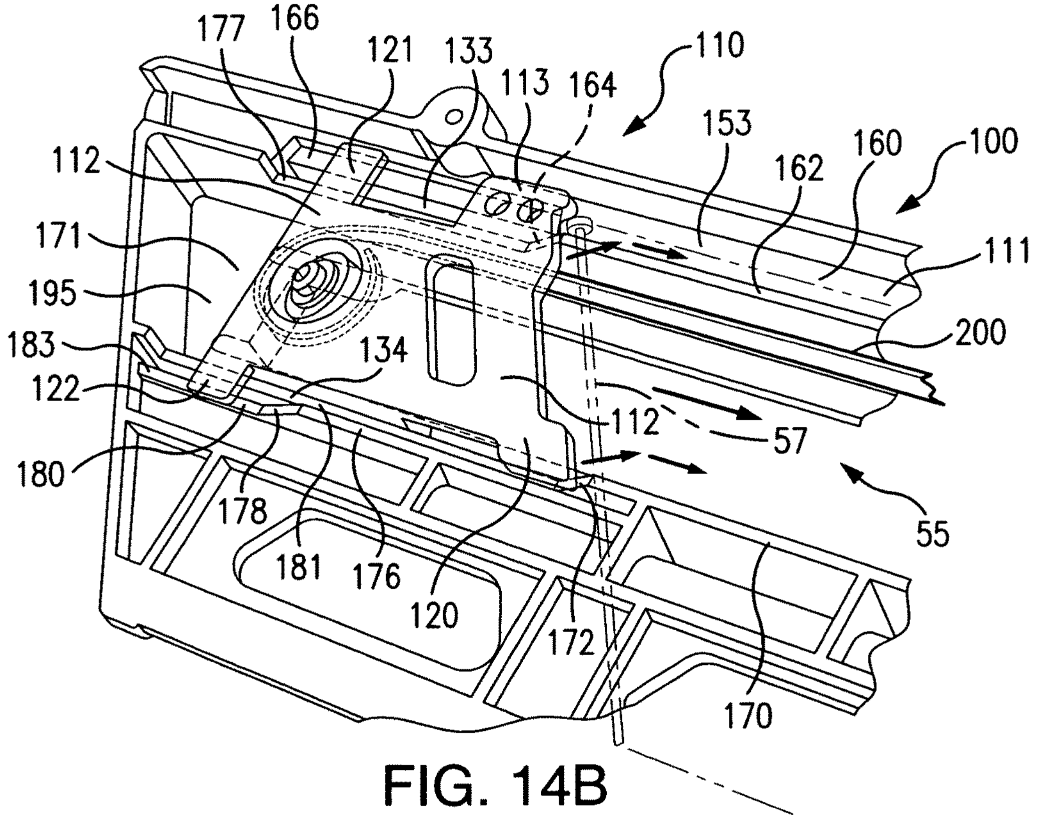
FIG. 14B is a nail-side sectional view of the magazine illustrating the pusher transitioning from a retracted state to an engaged state when the upper nose prong is guided by an upper nose prong ramp and the lower nose prong is guided by a lower nose prong ramp.
Figure 14C:
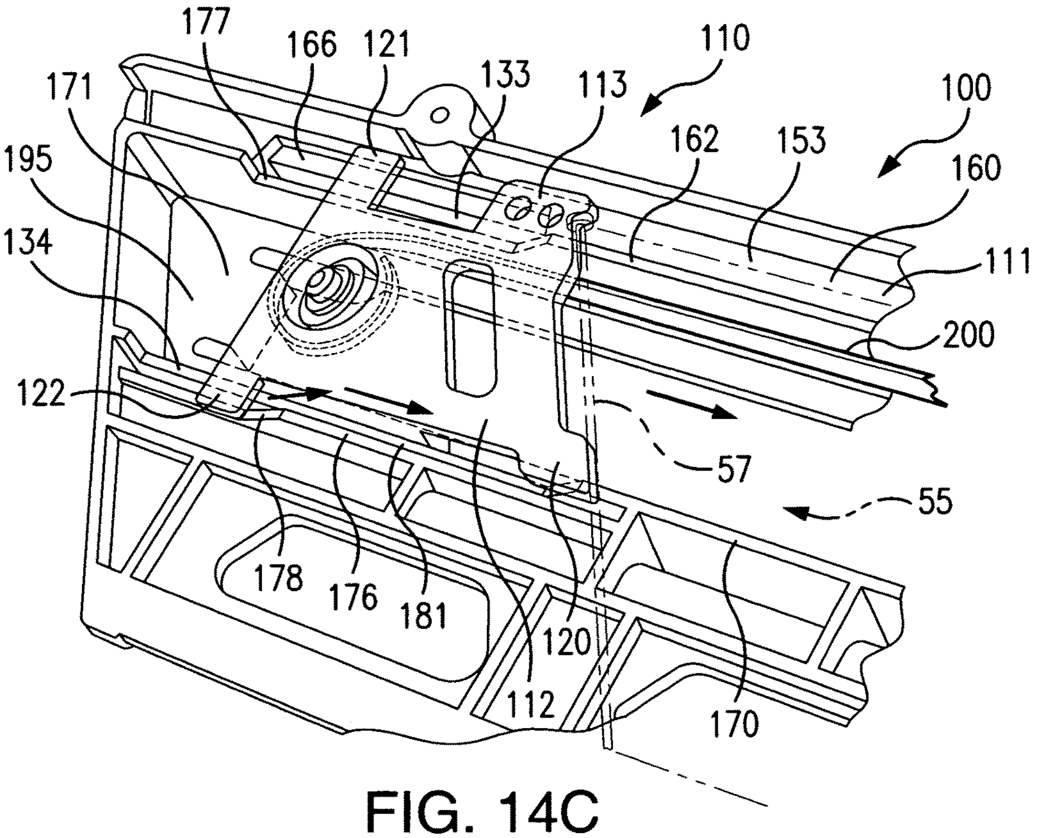
FIG. 14C is a nail-side sectional view of the magazine illustrating the pusher transitioning from a retracted state to an engaged state as the upper nose prong is guided by an upper pusher guide, the lower nose prong is guided by a lower pusher guide and lower base prong is guided by a lower base prong ramp.
Figure 14D:
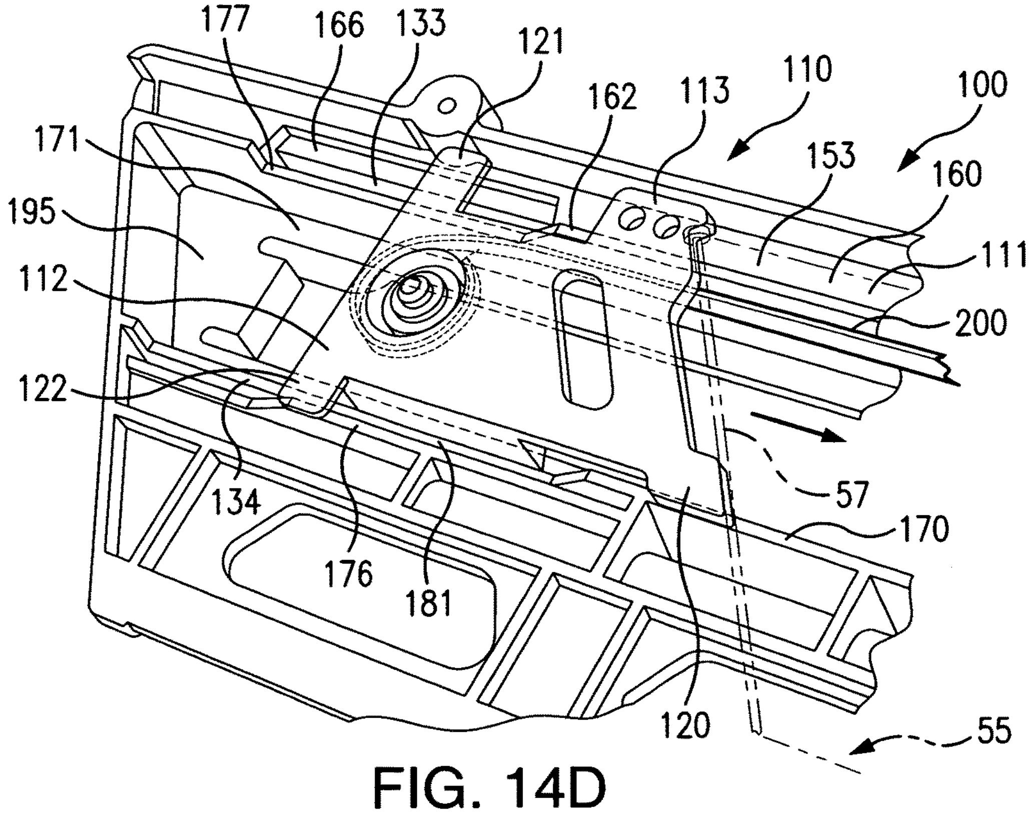
FIG. 14D is a nail-side sectional view of the magazine illustrating the pusher in an engaged state as the upper nose prong is guided by an upper pusher guide, the lower nose prong is guided by a lower pusher guide and lower base prong is guided by a lower base prong guide.
Figure 15:
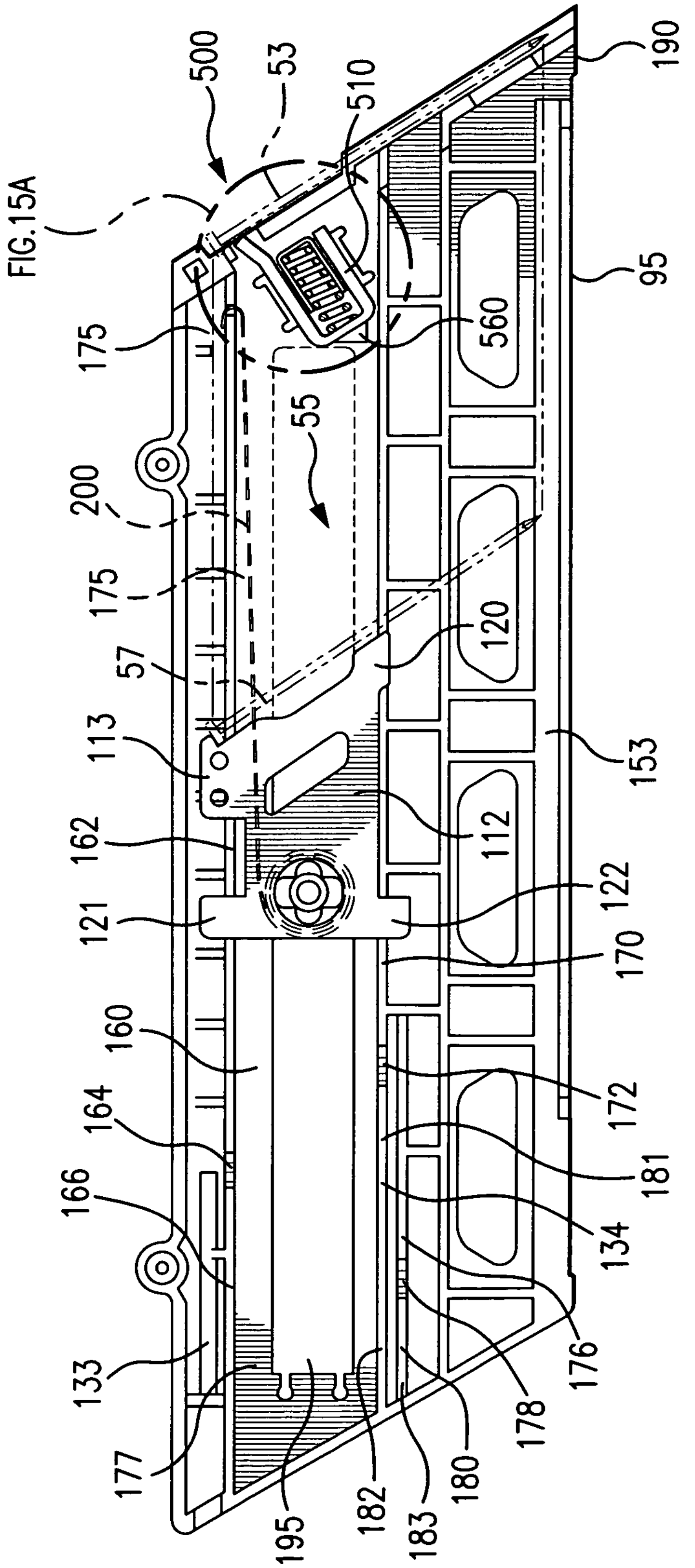
FIG. 15 is a nail-side sectional view of the magazine illustrating the pusher in an engaged state and illustrating a lockout mechanism.
Figure 15L:
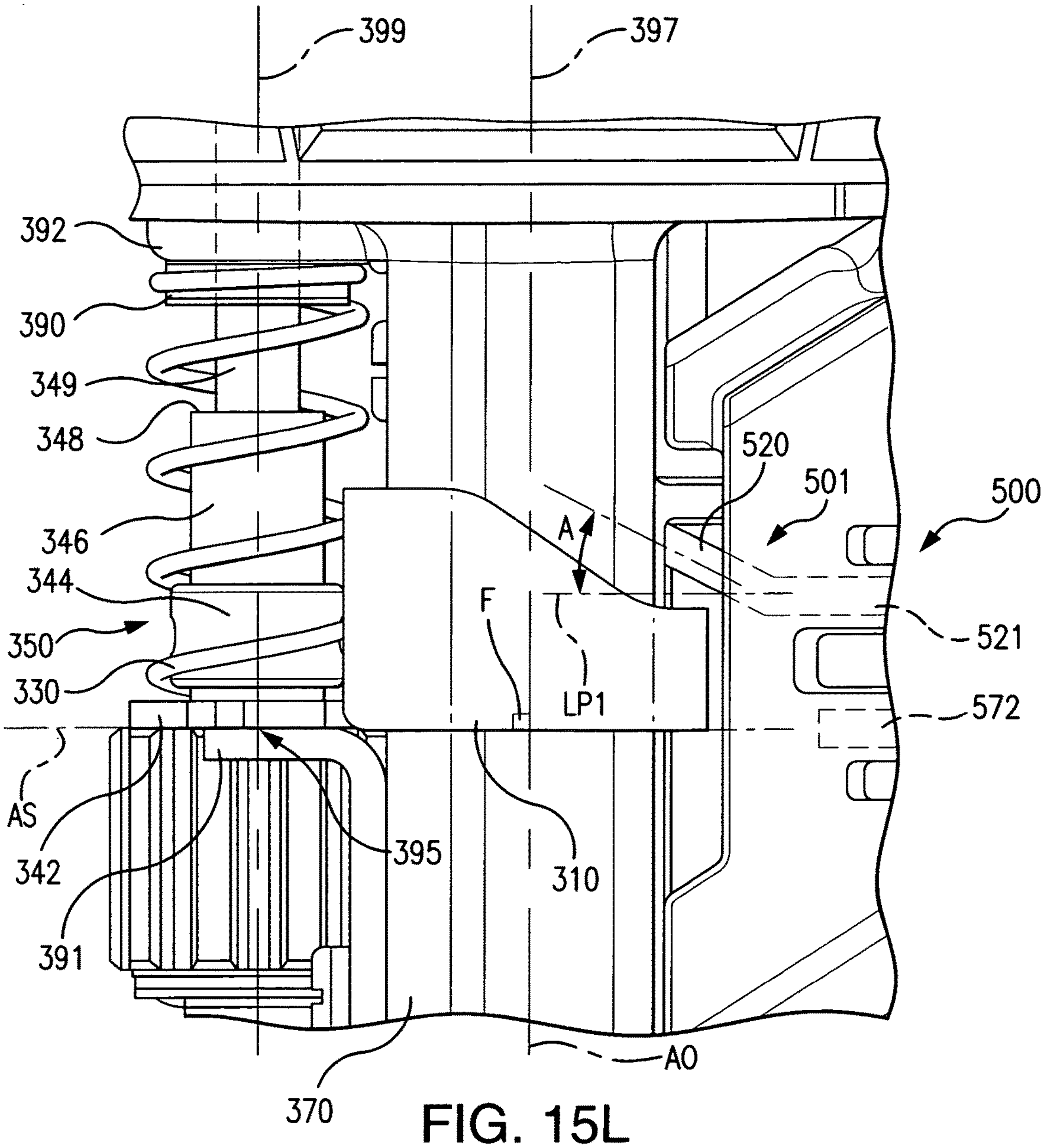
FIG. 15L is knob-side view of pusher in a down-stopped position.
Figure 16:
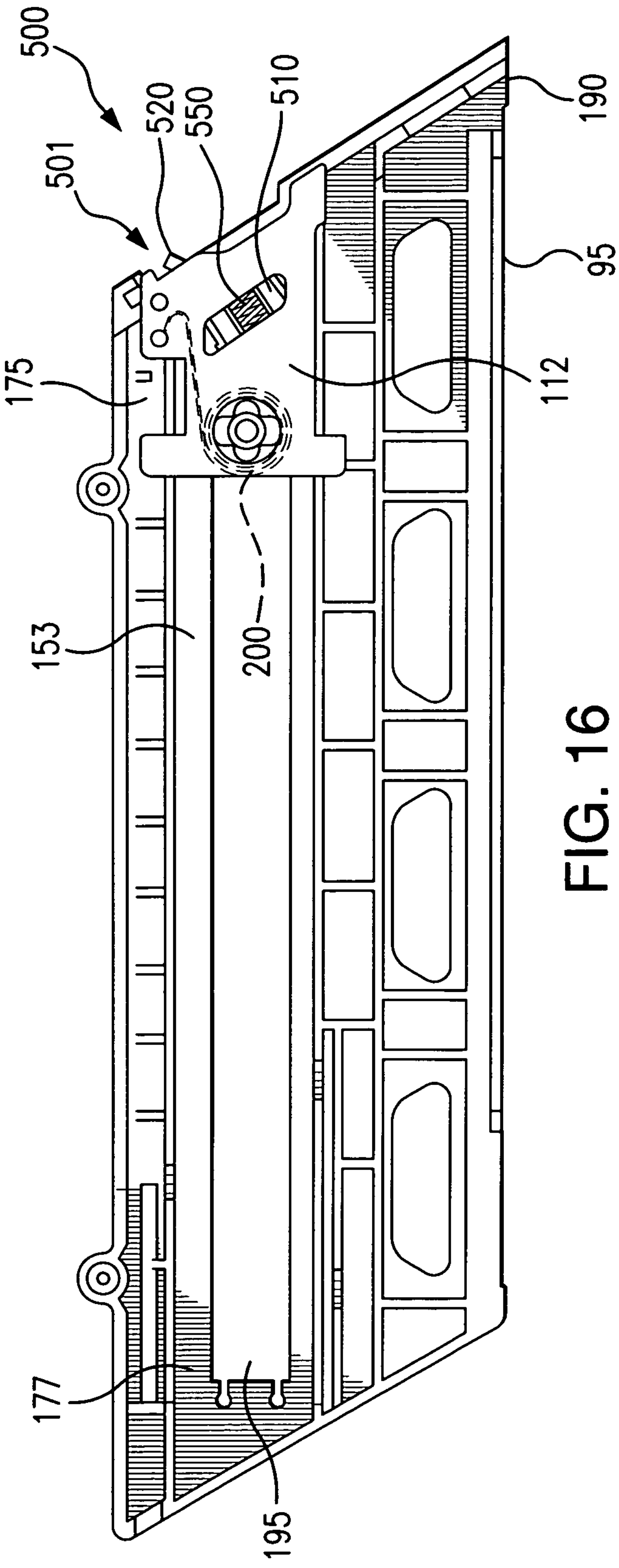
FIG. 16 is a nail-side sectional view of the magazine illustrating the pusher having caused a locked out state of the lockout mechanism.

The pusher assembly 110 is configured such that the pusher 112 can be in a retracted state wherein the pusher 112 is retracted into the pusher recess 171 (e.g. FIGS. 10B-C, FIG. 13 and FIGS. 14A) or the pusher 112 can be in an engaged state such that it is located at a position in the nail track 111 (e.g. FIGS. 15-16 and FIG. 14D). In an embodiment, in an engaged state the pusher 112 has moved out from the pusher recess 171 and in part or in whole into the nail track 111. FIG. 9 also illustrates a lockout 500 for prevent or inhibiting actuation a contact trip actuator 700 of nailer 1 when a predetermined number of nails or zero (0) nails are present in the magazine (e.g. FIGS. 15-15L).

Figure 10A:
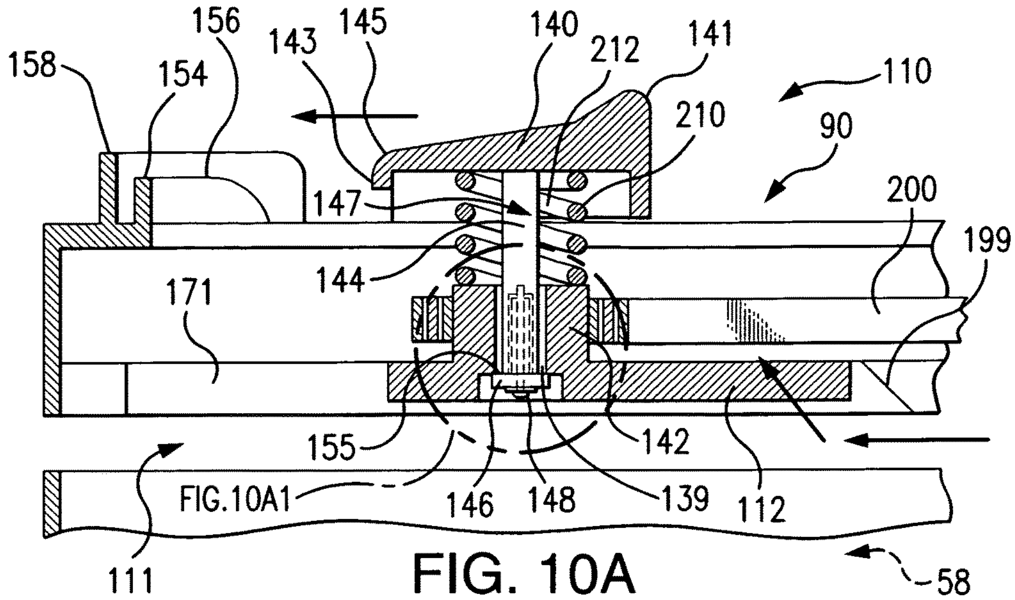
FIG. 10A is a sectional view of a pusher assembly having a pusher assembly knob moving toward a detent.

FIG. 10A is a sectional view of the pusher assembly 110 having the pusher assembly knob 140 moving toward a detent 156.

A latch pin 147 connects the pusher assembly knob 140 to the pusher 112 and passes through the guide path opening 152 (e.g. FIG. 9). The pusher assembly knob 140 has a knob stem 144. The knob stem 144 has a cylindrical cavity 136 (e.g. FIG. 10A1) configured to receive a plug stem portion 138 of a plug 137 which has a plug head 146 (e.g. FIG. 10A1). The plug 137 has a screw passage 135 (e.g. FIG. 10A1) through which screw 148 passes to secure the knob stem 144 and the plug 137 together.

The pusher 112 has a pusher assembly spool 142 which has a cylindrical passage 139 through which a portion of the assembly the knob stem 144 can be inserted. The spring 200 is illustrated spooled around the pusher assembly spool 142. The pusher 112 has a knob connector opening 155 in communication with a cylindrical passage 139. The knob connector opening 155 has radial dimensions smaller than the radial dimensions of a plug head 146 of the plug 137.

The pusher assembly 110 can be assembled by inserting at least in part the knob stem 144 within the pusher assembly spool 142 which has the cylindrical passage 139 through which the knob stem 144 is inserted.

Plug stem portion 138 of the plug 137 can be inserted through the knob connector opening 155 and at least in part into the cylindrical cavity 136. The screw 148 can be screwed through the screw passage 135 at least in part into assembly the knob stem 144 securing the pusher assembly knob 140 and the plug 137 together. In an embodiment, a washer 161 is placed under a screw head of the screw 148 to reduce undesired screw movement.

The plug head 146 can have a radial dimension which is larger than a redial dimension of the knob connector opening 155 such that the plug head 146 can not pass through the knob connector opening 155 of the pusher 112.

In an embodiment, the pusher assembly spool 142 has a knob connector opening 155 which has an oval shape, while the cylindrical passage 139 is cylindrical. In this embodiment, the oval shape of the knob connector opening 155 does not allow the plug head 146 to pass therethrough preventing the plug head 146 from entering into the cylindrical passage 139. This disclosure is not limited as to how the plug head 146 is prevented from passing through the knob connector opening 155 and should be broadly construed in this regard.

An inner diameter of cylindrical passage 139 can be larger than an outer diameter of the knob stem 144 such that the knob stem 144 can be tilted toward the nose end 102 and away from the base end 105 (e.g. FIG. 10C and FIG. 10D) such that the pusher assembly knob 140 can engage and disengage from the detent 156.

The pusher assembly knob 140 having an assembly knob nose end 141 can optionally be mounted upon a spring 210 which is placed between the pusher assembly spool 142 and the pusher assembly knob 140. The spring 210 can be a compressive spring. The assembly knob stem 144 can be inserted at least in part through a spring passage 212. Optionally, the spring 210 having the spring passage 212 can be used.

The pusher assembly knob 140 can be moved toward the detent 156 such that the pusher assembly knob base portion 145 passes over the detent 156 and reversibly engages the pusher assembly knob 140 with the detent 156. While reversibly engaged, the pusher assembly knob 140 can be latched by the knob base end 143 to a detent base end 154. FIG. 10A also illustrates the stop 158.

When the pusher assembly knob 140 is fixed in position by the detent 156, the pusher 112 is in a retracted position and the pusher assembly 110 is in a retracted state.

In an embodiment, the pusher 112 can be guided by at least one guide ramp into a recess (e.g. the pusher recess 171) while simultaneously the pusher assembly knob 140 is in contact with a detent, e.g. the detent 156. In an embodiment, a movement of the assembly knob 140 to engage detent 156 can simultaneously cause the pusher 112 to be guided into the pusher recess 171 by a guide ramp (e.g., an upper nose prong ramp 164 (FIG. 14A), or a ramp 285 (FIGS. 11 and 12)). In an embodiment, the reverse process can also be executed; the pusher 112 can be guided out of a recess (e.g. the pusher recess 171) by at least one ramp when simultaneously the pusher assembly knob 140 is moved while released from a detent.

FIG. 10B is a sectional view of the pusher assembly 110 having a pusher assembly knob 140 reversibly fixed by the detent 156. FIG. 10B illustrates the pusher assembly knob 140 reversibly latched onto the detent 156 by the latching of the knob base end 143 over the detent base end 154. Like reference numbers in FIG. 10A identify like elements in FIG. 10B.

Figure 10C:
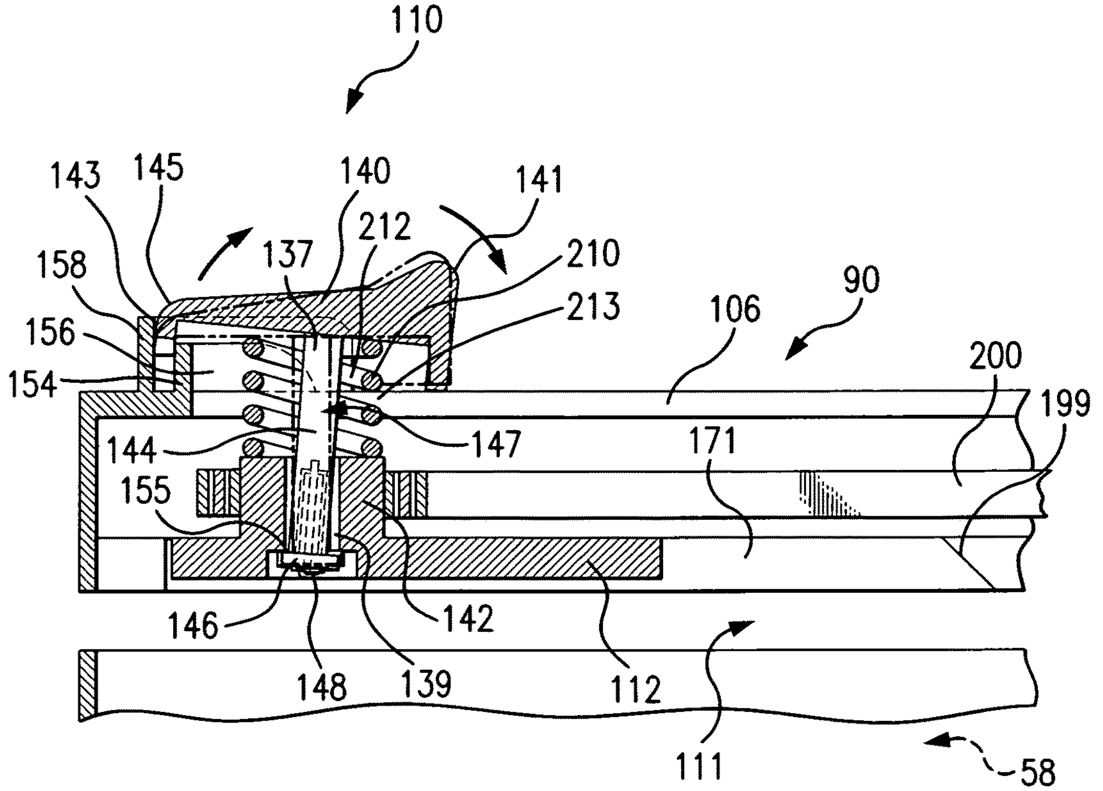
FIG. 10C is a sectional view of a pusher assembly having a pusher assembly knob which is being pushed to release it from a detent.

FIG. 10C is a sectional view of the pusher assembly 110 having the pusher assembly knob 140 experiencing or being pushed by both a lateral force toward the nose end 102 and a downward force toward the magazine body 106, thereby imparting a radial force on the nose side 213 of the spring 210. This compression of the nose side 213 of the spring 210 tilts a portion of the knob stem 144 toward the nose end 102. This tilting raises the knob base end 143 to allow it to move over the detent base end 154 toward the nose end 102. Like reference numbers in FIG. 10A identify like elements in FIG. 10C.

Figure 10D:
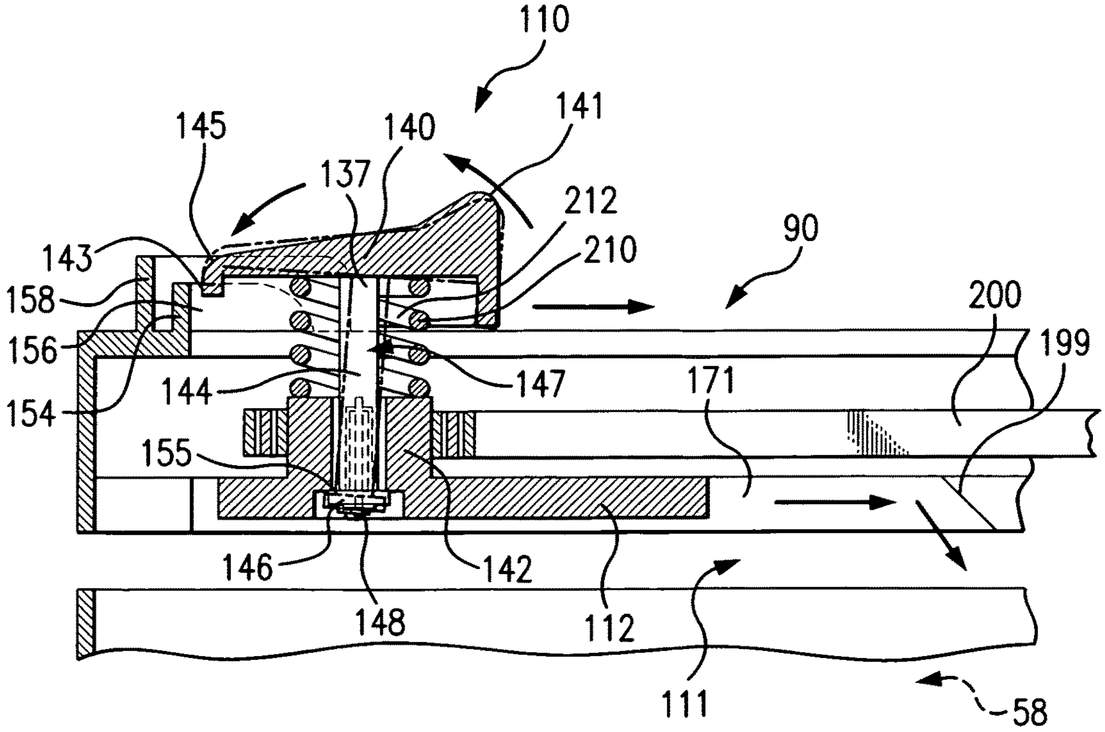
FIG. 10D is a sectional view of a pusher assembly having a pusher assembly knob released from a detent and moving away from the detent.

FIG. 10D is a sectional view of the pusher assembly 110 having a pusher assembly knob 140 which has been released from the detent 156 and which is moving away from the detent 156 toward the nose end 102 and into the nail track 111. When the knob base end 143 to moves past the detent base end 154 toward the nose end 102 the pusher assembly 110 also moves toward the nose end 102 and the pusher assembly 110 is disengaged from the detent 156. The pusher assembly knob 140 can return to its not tilted configuration as shown in FIG. 10A. Like reference numbers in FIG. 10A identify like elements in FIG. 10D.

Figure 10E:
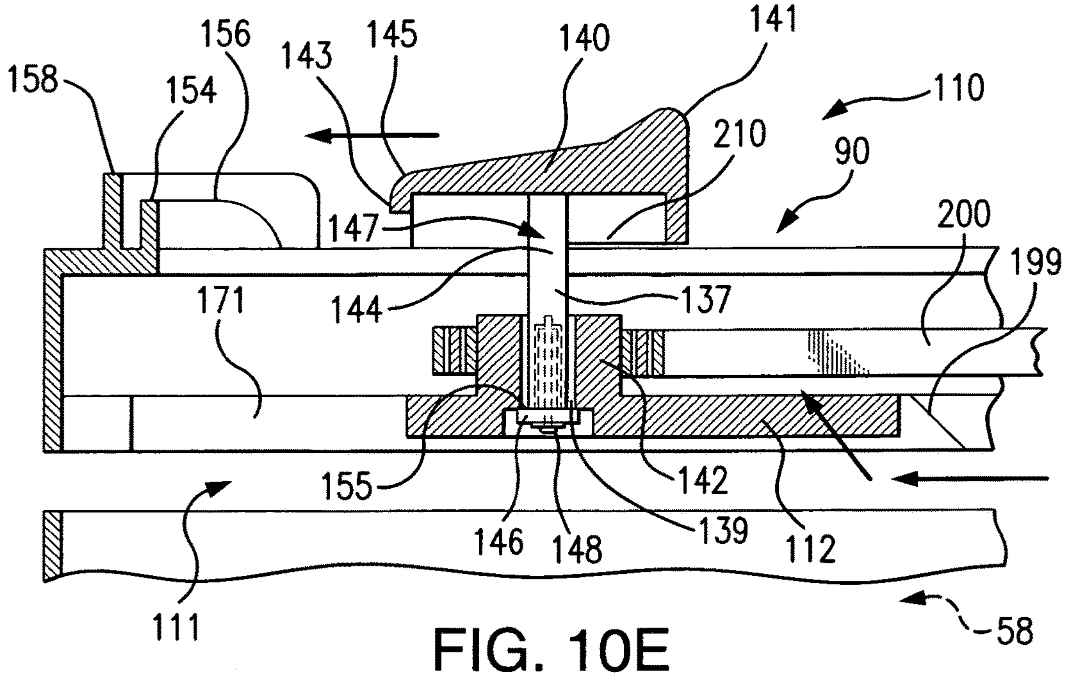
FIG. 10E is a sectional view of a pusher assembly having a spring-free pusher assembly moving toward a detent.

FIG. 10E is a sectional view of the pusher assembly 110 having the pusher assembly knob 140 moving toward the detent 156. In the embodiment of FIGS. 10E-10H, the embodiment of the pusher assembly 110 is a spring-free pusher assembly. In this embodiment "spring-free" means that a spring is not used at a location between the pusher assembly spool 142 and the pusher assembly knob 140. In this embodiment, a spring analogous to the spring 210 of FIG. 10A is not used.

FIG. 10E illustrates an embodiment in which a latch pin 147 connects the pusher assembly knob 140 to the pusher 112 and passes through the guide path opening 152 (e.g. FIG. 9). In this embodiment, the forces provided by the spring 200 and the reversible fitting of the knob base end 143 with the detent base end 154 achieves the reversible retraction of the pusher assembly 110. Like reference numbers in FIG. 10A identify like elements in FIG. 10E.

In an embodiment, movement of the pusher assembly knob 140 toward the detent 156 allows the pusher 112 to be guided by a ramp 199 into the pusher recess 171 out of the nail track 111. In the reverse process, the movement of the pusher assembly knob 140 away from the detent 156 allows the pusher 112 to be guided by the ramp 199 out of the pusher recess 171 into the nail track 111.

Figure 10F:
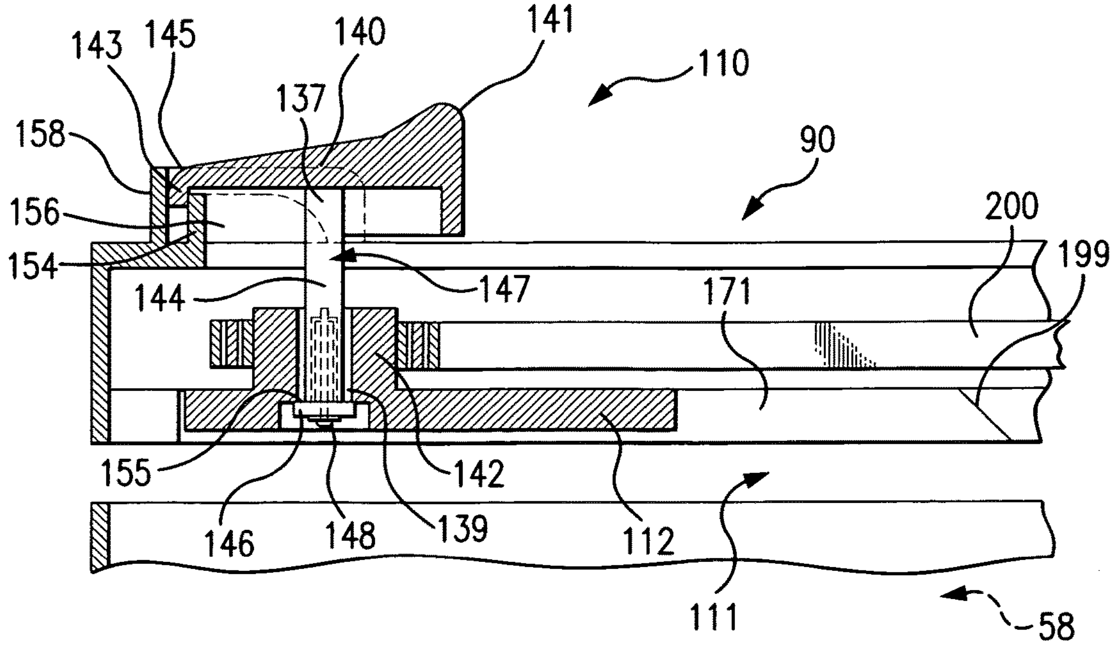
FIG. 10F is a sectional view of a pusher assembly having a spring-free pusher assembly reversibly fixed by a detent.

FIG. 10F is a sectional view of with a spring-free pusher assembly reversibly fixed by a detent. Like reference numbers in FIG. 10E identify like elements in FIG. 10F.

Figure 10G:
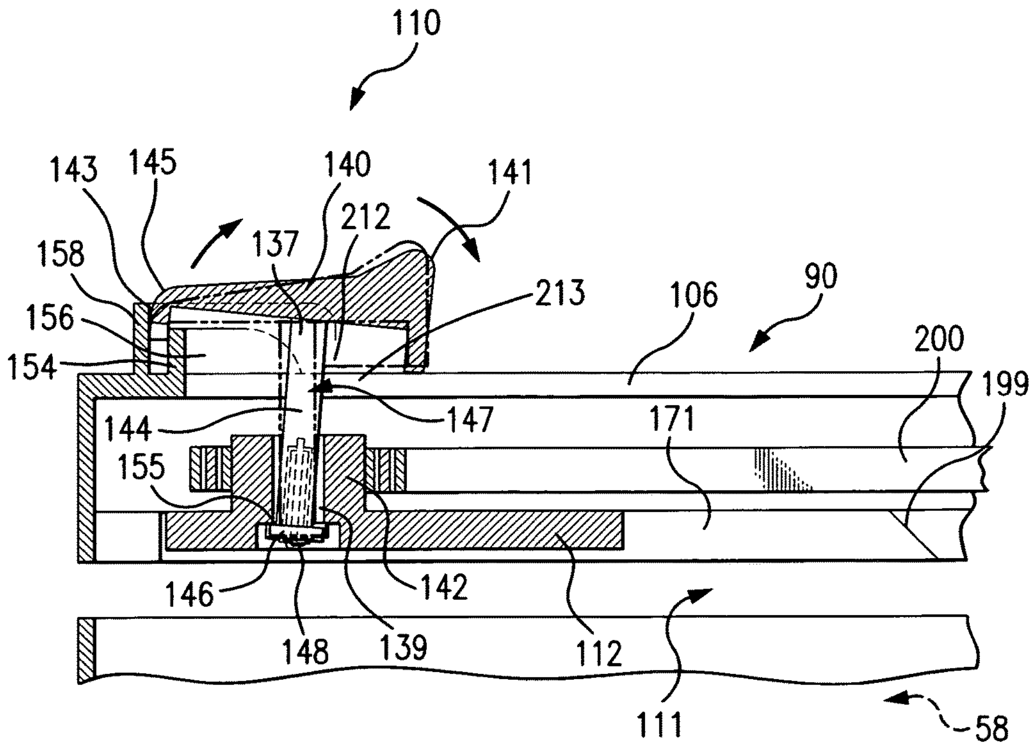
FIG. 10G is a sectional view of a pusher assembly having a spring-free pusher assembly which is being pushed to release it from a detent.

FIG. 10G is a sectional view of a pusher assembly having a spring-free pusher assembly which is being pushed to release it from a detent. In an embodiment, movement of the pusher assembly knob 140, which is spring-free, in a manner to engage the detent 156 can achieve retraction of the pusher 112. Like reference numbers in FIG. 10E identify like elements in FIG. 10G.

Figure 10H:
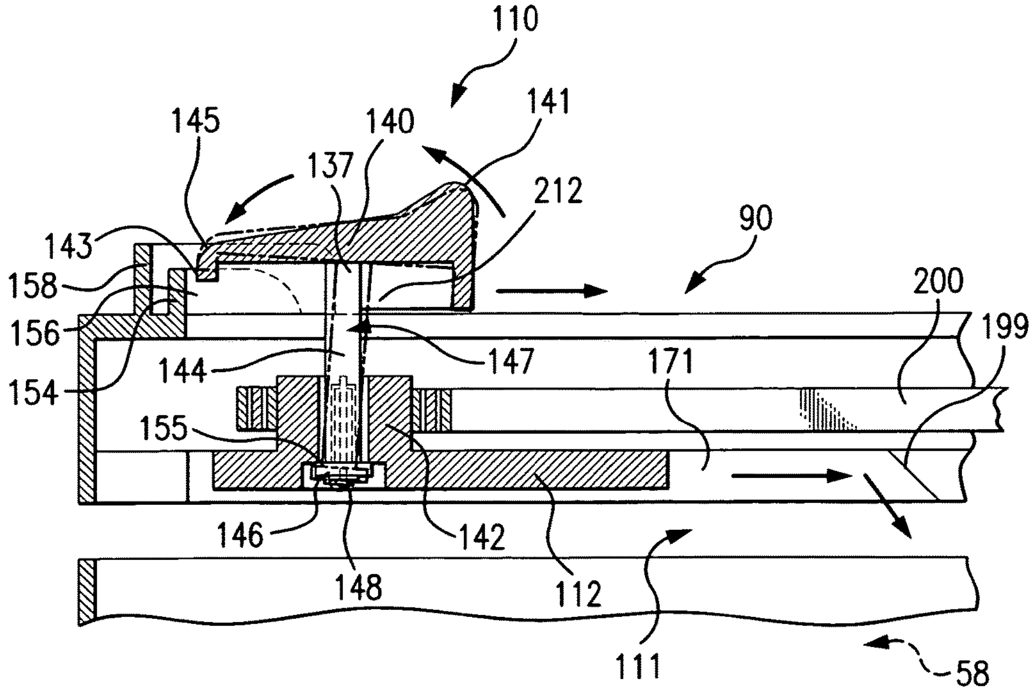
FIG. 10H is a sectional view of a pusher assembly having a spring-free pusher assembly released from a detent and moving away from the detent.

FIG. 10H is a sectional view of a pusher assembly having a spring-free pusher assembly released from a detent and moving away from the detent, then into the nail track 111. Like reference numbers in FIG. 10E identify like elements in FIG. 10H.

Figure 10I:
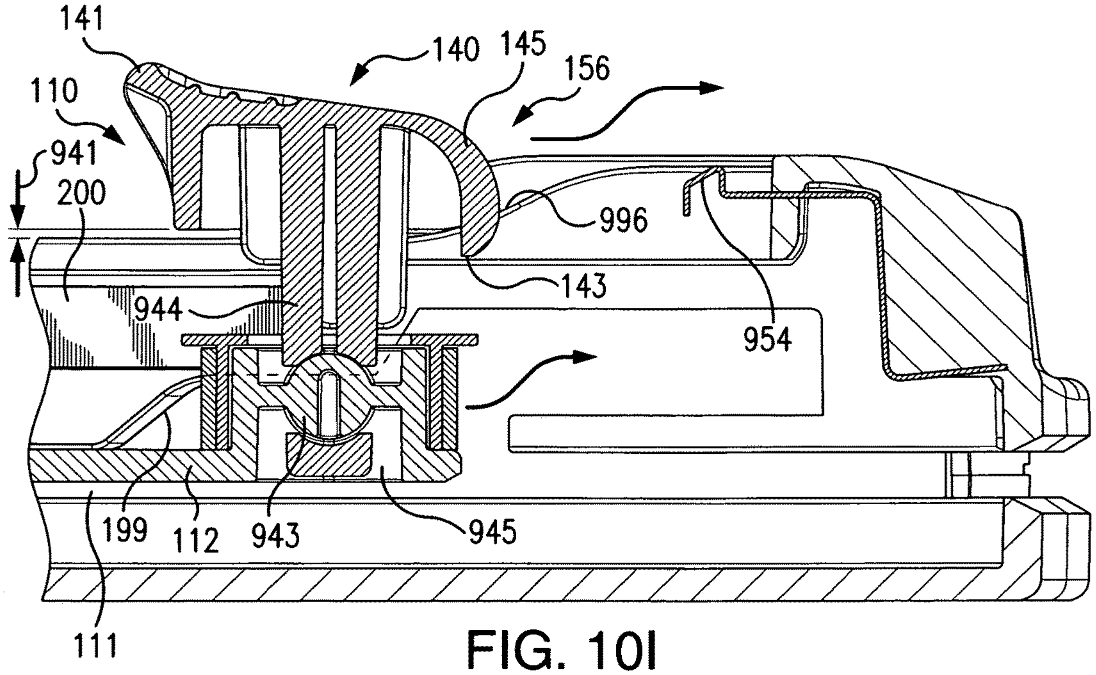
FIG. 10I is a sectional view of the pusher assembly having the pusher assembly knob which has the pivot stem and which is moving toward the detent.

FIG. 10I is a sectional view of an embodiment of the pusher assembly in which the pusher assembly knob 140 has a pivot stem 944 and which is moving toward the detent 156. In the embodiment of FIG. 10I, the pivot stem 944 is pivotably attached to a pivot 943. The pivot 943 can be located in a pivot chamber 945 of the pusher assembly 110. The pusher assembly knob 140 can have the pusher assembly knob base portion 145 which has the knob base end 143. FIG. 10I also shows a spring latch 954 of the detent 156.

As shown in FIG. 10I, in an embodiment the movement of the pusher assembly 110 toward the spring latch 954 reversibly moves the pusher assembly 110 into its retracted position. The latching of the pusher assembly knob 140 to the spring latch 954 achieves the reversible retraction of the pusher assembly 110. In an embodiment, the pusher assembly knob 140 can have the pusher assembly knob base portion 145 which has the knob base end 143 that can be reversibly latched to the spring latch 954. Like reference numbers in FIG. 10A identify like elements in FIG. 10I.

Figure 10J:
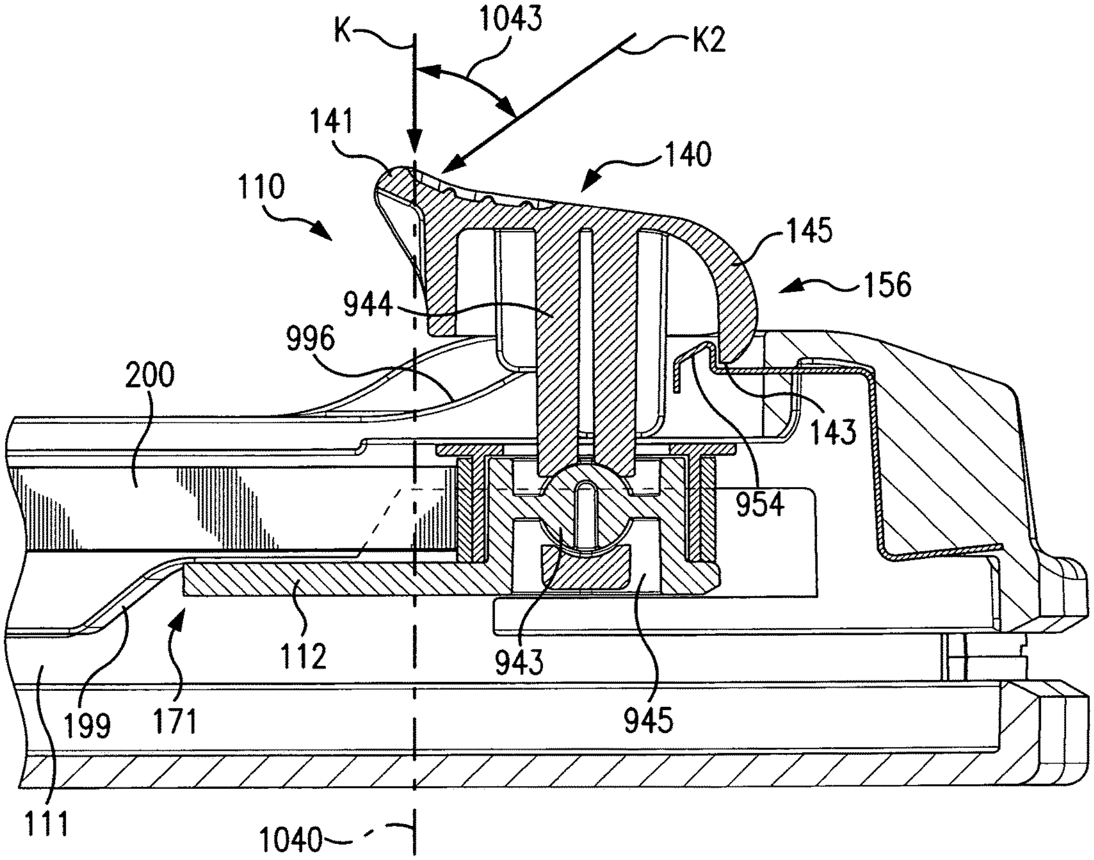
FIG. 10J is a sectional view of the pusher assembly having the pusher assembly knob which has the pivot stem and which is reversibly fixed by the detent.

In an embodiment, movement of the pusher assembly knob 140 toward the detent 156 allows the pusher 112 to be guided by the ramp 199 at least in part, or wholly, into the pusher recess 171 out of the nail track 111. In the reverse process, the movement of the pusher assembly knob 140 away from the detent 156 allows the pusher 112 to be guided by the ramp 199 out of the pusher recess 171 and into the nail track 111 (FIG. 10J). Optionally, a knob ramp 996 can be used to guide the pusher assembly knob 140 toward the spring latch 954 to facilitate latching.

In an embodiment, when the pusher assembly 110 is not retracted and the pusher 112 is engaged in the nail track 111, the pusher assembly knob 140 can be set to have a knob clearance 941 which reduces and/or eliminates friction between the assembly knob 140 and the magazine body 106. The knob clearance 941 can have a distance in a range such as 0.001 mm or greater, for example: 0.05 mm, 0.075 mm, 1.0 mm, 1.25 mm, 1.5 mm, 2.0 mm, 2.5 mm, 3.0 mm, 5 mm, 10 mm, or greater.

FIG. 10J shows the pusher 112 in its retracted state and the pusher assembly knob 140 reversibly latched to the spring latch 954. In an embodiment, the spring latch 954 can be made at least in part of formed sheet metal. The spring latch 954 can be made in part or in whole from a broad variety of materials such as metals, formed metals, plastics, polymers, cured resins or any other material with flexibility and durability properties to be able to function as the spring latch 954 for the pusher assembly knob 140. Like reference numbers in FIG. 10I identify like elements in FIG. 10J.

The spring latch 954 can be formed to have a spring action when experiencing force from the pusher assembly knob 140, or other source. Force sufficient to cause a spring action of the spring latch 954 can be imparted by the pusher assembly knob 140 when the pusher assembly knob 140 is being latched to the spring latch 954, or when the pusher assembly knob 140 is pivoted to unlatch the pusher assembly knob 140 from the spring latch 954. In an embodiment, when the pusher assembly knob 140 is being latched, the force against the detent from at least a portion of the pusher assembly knob such as the knob base portion 145 and/or the knob base end 143 can cause a spring action of spring latch 954 to occur.

EXAMPLE 1

In the embodiment of FIG. 10J, the pusher assembly knob 140 can be unlatched by a release force of 3 lbf or less which is applied in the direction of arrow K to at least a portion of the pusher assembly knob 140, such as the assembly knob nose end 141. FIG. 10J shows the direction of arrow K can be along a push axis 1040 which can be perpendicular to the longitudinal centerline 1027. Additionally, the pusher assembly knob 140 can be unlatched by a release force applied in the direction of arrow K2 (FIG. 10J) of 2.25 lbf or less. The release force of 2.25 lbf or less can be applied to the assembly knob nose end 141 at an angle 1043 in a range of from 15° to 90°, for example: 80°, or 66°, or 45° or 33°, or 25°.

In Example 1, the reversible latching of the pusher assembly knob 140 to a portion of detent 156 allows for a release and/or unlatching by a force of 3 lbf or less applied at any of a wide range of angles to various portions of the pusher assembly knob 140. The reversible latching of the pusher assembly knob 140 to the spring latch 954 allows for a release and/or unlatching by a force of 3 lbf or less applied at any of a wide range of angles to various portions of the pusher assembly knob 140.

Figure 10K:
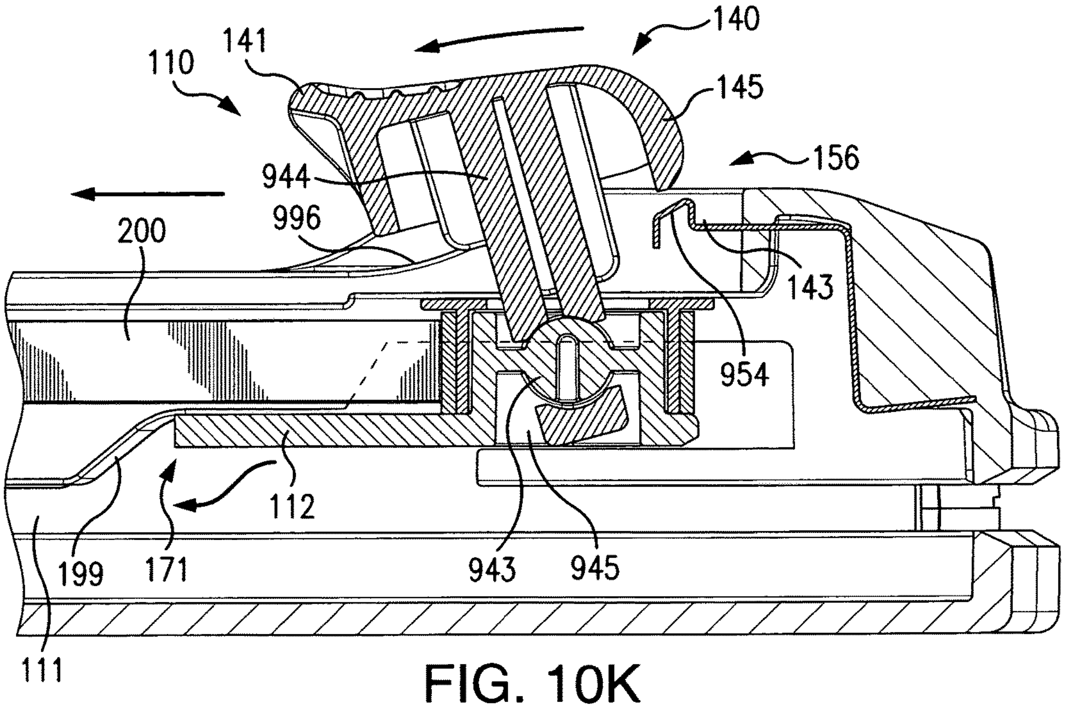
FIG. 10K is a sectional view of the pusher assembly having the pusher assembly knob which has the pivot stem and which is being pushed to achieve release from the detent.

FIG. 10K shows an embodiment in which the pusher assembly knob 140 can be unlatched from the spring latch 954 by applying a release force to the pusher assembly knob 140, for example at the assembly knob nose end 141. Applying a release force to the pusher assembly knob 140 can pivot the pusher assembly knob 140 and the pivot stem 944 about the pivot 943 which can disengage the knob base end 143 of the pusher assembly knob base portion 145 from the spring latch 954. Like reference numbers in FIG. 10I identify like elements in FIG. 10K.

In an embodiment, the pusher assembly knob 140 can have a pivoting stem member, such as pivot stem 944 or knob stem 144, which in conjunction with detent 156 can achieve a quick release mechanism which allows an operator to unlatch a latched pusher assembly knob by applying a force of 15 lbf or less, for example: 10 lbf, or 6 lbf, or 5 lbf, or 3 lbf, or 2.75 lbf, or 2.5 lbf, or 2.25 lbf, or 2.0 lbf, or 1.75 lbf, or 1.5 lbf, or 1.25 lbf, or 1.0 lbf, or 0.75 lbf, or 0.5 lbf, or 0.25 lbf. Optionally, the detent base end 154 or the spring latch 954 can be used in the quick release mechanism. In an embodiment, the spring 200 can also be a member of the quick release mechanism and can impart a bias upon the pusher assembly which can move the pusher assembly 110 into an engaged state automatically once the pusher assembly knob 140 is unlatched. In yet another embodiment, the spring 200 imparts a bias upon the pusher assembly which contributes to the unlatching of the pusher assembly knob 140 when an operator initiates an unlatching movement of the pusher assembly knob 140. In an embodiment, the bias of spring 200 imparted upon the pusher assembly can be in a direction generally toward the nose end 102 of the magazine 100.

In an embodiment, a retracted pusher assembly can move the pusher 112 automatically under a bias imparted by spring 200 out of the pusher recess 171 and into the nail track 111 to achieve an engaged state of the pusher assembly 110 when the pusher assembly knob 140 is unlatched. In an embodiment, unlatching the pusher assembly knob 140 and/or movement of the pusher 112 out of the pusher recess 171 and into the nail track 111 to achieve an engaged state can be manually achieved by an operator. In an embodiment, the transition of the pusher assembly 110 form a retracted and latched state to an engaged state in which the pusher 112 moves from the pusher recess 171 into nail track 111 can be a spring assisted manual action in which both a force provided by an operator and a bias imparted by spring 200 act together achieve the engaged state of the pusher assembly 110.

FIG. 11 is a sectional view of another embodiment of a pusher assembly which can be used with the magazine 100 and which can be fixed by engagement with another embodiment of a detent. FIG. 11 illustrates, a pusher assembly 215 having a knob 216 having a notch 217 in a fixed position by its engagement with the detent 260.

The notch 217 can be configured to mate with the detent 260. As illustrated, the knob 216 is in a fixed position and reversibly mated with the detent 260. In this configuration, a pusher 225 is retracted into a recess 280. The pusher 225 is maintained in the recess 280 when the pusher assembly 215 is in a retracted state. The retraction of the pusher 225 is achieved by the bias of a spring 220 pushing a retracting member 229 away from the nail track 111. The retracting member 229 is connected to the pusher 225 by the pusher connecting member 227. The pusher 225 can be maintained in a retracted state by the bias of the spring 220 against the retracting member 229.

As shown in FIG. 11, while the pusher assembly 215 is in a retracted state, a plurality of nails 55 can be loaded into the magazine 100 through a nail feed slot 59.

The pusher assembly 215 can be transitioned from a retracted state to an engaged state by an operator pressing the knob 216 in a fashion that imparts force upon the knob 216 in a direction laterally toward the nose end 102 and also in a direction toward the magazine body 106. This type of pressing motion can impart a radial movement tilting the knob 216 which can raise the notch 217 and disengage the notch 217 from the detent 260. When the knob 216 is disengaged and no longer fixed by the detent 260, the pusher assembly 215 can move away from the base end 105 and toward the nose end 102 of the magazine. A ramp 285 can connect the recess 280 with the nail track 111. Movement of the pusher assembly 215 away from the base end 105, moves the pusher 225 along the ramp 285 which can compress the spring 220 such that the pusher 225 can move out of the recess 280 and can be brought into alignment behind a nail 57 in the nail tract 111. The detent (e.g., 260) can be a raised feature of the magazine housing.

The spring 200 biases the pusher 225 in a direction from the base end 105 to the nose end 102. The bias of the spring 200 moves the pusher 225 toward the nose end 102 and pushing the pusher 225 against a nail 57. The contact of the pusher 225 against the nail 57 of the plurality of nails 55 imparts a force to the plurality of nails 55 such that they are fed to the nosepiece 12 to be driven into a workpiece.

In other embodiments which can be similar to the embodiments disclosed in FIGS. 11-12, the spring 220 is not used. In another embodiment, a single spring member, can be used impart bias against a detent and to retract a pusher.

In yet another embodiment, a recess 280 can be provided near the base end 105 of the magazine 100 for a pusher 225 to retract into by means of a spring bias when the pusher assembly 215 is pulled longitudinally back toward the base end 105. A detent is located near the base end 105 position to engage the pusher assembly 215 and provide resistance to overcome a negator spring force until the operator is finished with a loading/unloading of nails and is ready for tool operation at which point operator moves the pusher assembly 215 in the opposite direction thus overcoming the detent and allowing negator to pull the pusher assembly 110 towards the nose end 102.

FIG. 12 is a sectional view of an embodiment of a pusher assembly which can be maintained in a retracted state by utilization of yet another embodiment of a detent. In the embodiment illustrated in FIG. 12, a pusher assembly 226 is maintained, or reversibly fixed, in a retracted state by a spring loaded detent 230. The spring loaded detent 230 has a detent body 231 having an upper face 238 with an upper ramp portion 234 and a lower ramp portion 236. When a force is applied to the detent body 231, the spring loaded detent 230 can move at least in part away from a knob 221 into a cavity 240 of the magazine 100.

A spring 242 is biased toward a retracting member 229 and the spring loaded detent 230 is pushed in a direction toward the retracting member 229 by the bias of the spring 242 which extends from a base 249 in the cavity 240 into a detent cavity 232 and biasing the spring loaded detent 230 toward the knob 221. The spring loaded detent 230 is engaged with the cavity 240 and prevented from disengaging from the cavity 240 and the spring 242 by a stop 243 of a cavity wall 245 of the detent cavity 232. In an embodiment, the cavity wall 245 can guide the detent rim 241.

FIG. 12 illustrates the pusher assembly 226 in a reversibly retracted state. The retracted state of the pusher assembly 226 shown in FIG. 12 can be achieved by moving the knob 221 in a direction toward the base end 105. This pulling can move the pusher assembly such that a knob base portion 223 contacts the spring loaded detent 230 in blocking position at lower detent ramp portion 236. A blocking position can be a position of a spring loaded detent 230 which blocks at least a portion of the knob 221 from a motion in a direction. Then, the knob 221 can move against the upper face 238 of the spring loaded detent 230 and across the upper detent ramp portion 234 by compressing the spring 242 and pushing the spring loaded detent 230 at least partially into the cavity 240, such that the knob 221 can move over and past the spring loaded detent 230 toward the base end 105.

The spring loaded detent 230 can return to its blocking position after movement of the knob 221 over and past the spring loaded detent 230 toward the base end 105. The spring loaded detent 230 can return to its blocking position as a result of the bias of the spring 242 acting on the spring loaded detent 230 and moving the spring loaded detent 230 into a blocking position. In the blocking position, the spring loaded detent 230 can prevent or block the knob 221 from moving past the spring loaded detent 230 and away from the base end 105. This blocking can occur for example when the pusher assembly 226 is in its retraced state by a contact between the upper ramp portion 234 and a knob nose portion 237 such that the spring loaded detent 230 prevents the knob nose portion 237 from moving away from the base end 105 and can reversibly secure and reversibly maintains the pusher assembly 226 in a retracted state. Like reference numbers in FIG. 11 identify like elements in FIG. 12.

The pusher assembly 226 can be moved into an engaged state by moving the knob 221 in a direction away from the base end 105 and toward the nose end 102, such that the knob nose portion 237 is pushed against the spring loaded detent 230 thereby compressing the spring 242. Compressing the spring 242 can move the spring loaded detent 230 at least in part into the cavity 240 such that the knob 221 can pass over the spring loaded detent 230 when the spring loaded detent 230 is experiencing compression.

In an embodiment, when the knob 221 passes over the spring loaded detent 230 in a direction away from the base end 105 and toward the nose end 102, the engaged state can be achieved when the spring 200 is biased away from the base end 105 and toward the nose end 102 such that the spring 200 forces the pusher 225 to move along the ramp 285 and into the nail track 111 behind the nail 57 pushing the plurality of nails 55 toward the nosepiece assembly 12 to be driven. Like reference numbers in FIG. 11 identify like elements in FIG. 12.

This disclosure is not limited regarding means for depressing the spring loaded detent 230 and should be broadly construed in this regard. In another embodiment, the spring loaded detent 230 can be moved into the cavity 240 to an extent which allows the knob 221 to pass over the spring loaded detent 230 in a direction away from the base end 105 and toward the nose end 102 thus placing the pusher assembly 226 into an engaged state.

FIG. 13 is a sectional view from the nail-side 58 of the magazine 100 illustrating the pusher assembly 110 in a retracted state and the magazine 100 loaded with a plurality of nails 55. FIG. 9 also illustrates a lockout 500 (e.g. FIGS. 15-15L).

The pusher assembly 110 has a pusher 112 which is configured to push a nail 57 of a plurality of nails 55 which have been loaded into the magazine 100. The pusher 112 has a pusher nose end 129 and a pusher base end 130, as well as an upper pusher portion 131 and a lower pusher portion 132. In the embodiment illustrated in FIG. 13, the pusher 112 has a lower pusher face 119 and an upper pusher face 115. The lower pusher face 119 and the upper pusher face 115 can be configured such that they each can be brought into reversible contact with a nail 57 of the plurality of nails 55 located in the nail track 111 of the magazine 100. The lower pusher face 119 and the upper pusher face 115 can each optionally have an indentation into which a nail can be partially seated. In an embodiment, the pusher 112 can have a nose end notch 117 which is positioned at a location between an upper pusher face 115 and a lower pusher face 119. The pusher 112 and the nail track 111 can be sized to accommodate a collation wrapping (e.g., paper, plastic, band or other material wrapping) of the plurality of nails 55. In an embodiment, a nose end notch 117 can be sized to accommodate a collation wrapping of the plurality of nails 55. Optionally, the pusher nose end 129 can have an upper pusher nose ramp 116 connecting the upper pusher face 115 with the nose end notch 117. The pusher nose end 129 can also optionally have a lower pusher nose ramp 118 connecting the nose end notch 117 to the lower pusher face 119.

The magazine 100 can have one guide or a plurality of guides which can guide the pusher 112. A guide can guide the pusher 112 to a nail 57 of the plurality of nails 55 when the pusher 112 is in an engaged state.

The guide can also guide the pusher 112 into a pusher recess 171 to achieve a retracted position of the pusher 112. In an embodiment, an upper pusher recess 133 can have an upper pusher nail head notch 114. The guide can optionally have at least one pusher ramp along which the pusher 112 travels when it is guided in its movement from an engaged state in which the pusher 112 is not in the pusher recess 171 to a retracted state in which the pusher 112 is retracted into the pusher recess 171, as well as during transition from the retracted state to the engaged state.

FIG. 13 illustrates an embodiment of the pusher assembly 112 having a plug head 146 securing in-part the plug 137 by a screw 148 to a pusher assembly 110, as well as illustrating a knob connector opening 155 which can have an oval or other shape which can prevent the plug 137 from passing through the knob connector opening 155 and into the cylindrical passage 139's (FIG. 10A1) entrance. Like reference numbers in FIG. 14A identify like elements in FIG. 13.

FIG. 14A is a sectional view from a nail-side 58 angle of the magazine 100 illustrating the pusher 112 in a retracted state.

In an embodiment, illustrated in FIG. 14A, a pusher recess 171 into which the pusher 112 can be recessed can be formed by an upper pusher recess 133, a lower nose prong recess 181 and a lower base prong recess 183. In FIG. 14A, the pusher 112 is illustrated as positioned in a pusher recess 171.

Such position is a retracted position and the pusher assembly 110 is illustrated in an example of a retracted state.

In this embodiment the pusher recess 171 has an upper pusher recess guide 166 and a lower pusher recess guide 134. The magazine has a pusher guide track 160 which can guide the pusher 112. The pusher guide track 160 can have an upper pusher guide 162 and a lower pusher guide 170. The pusher guide track 160 has a guide track nose end 175 (FIG. 15 and FIG. 16) and a guide track base end 177 which can be proximate to the pusher track base end 195. The pusher recess 171 can be located proximate to the pusher guide track base end 177. The pusher 112 can have an upper nose prong 113 and an upper base prong 121 which can be guided by the upper pusher guide 162. The pusher 112 can also have a lower nose prong 120 and a lower base prong 122 which can be guided by the lower pusher guide 170. In an embodiment, the pusher guide track 160 has an upper nose prong ramp 164 which transitions the upper pusher guide 162 to the upper pusher recess 133. The upper nose prong 113 and upper base prong 121 of the pusher assembly 110 can be guided by the pusher guide track 160 into the upper pusher recess 133. The upper pusher recess can have an upper pusher recess 133 into which the upper base prong 121 and the upper nose prong 113 are retracted. The pusher guide track 160 can also have a lower pusher guide 170 which can guide lower nose prong 120 and a lower base prong guide 176. The lower pusher guide 170 can be connected to a lower nose prong recess 181 by a lower nose prong ramp 172. The lower base prong guide 176 can be positioned adjacent to and lower in the magazine than lower pusher guide 170. The lower base prong guide 176 can be connected to a lower base prong recess guide 180 by the lower base prong ramp 178.

A nail 57 is shown in hidden lines in FIG. 14A to illustrate that when the pusher assembly 110 is in a retracted state, a plurality of nails 55 having the nail 57 can be loaded into the magazine 100 the nail track 111. FIG. 14A also illustrates the spring 200 and identifies the guide frame inside portion 153.

In an embodiment, to achieve retraction of the pusher 112 into the upper pusher recess 133, the pusher 112 can be moved away from the pusher track nose end 190 (e.g. FIG. 13) in the direction of the pusher track base end 195 to a point where the lower base prong 122 is positioned adjacent to the lower base prong ramp 178 and the lower nose prong 120 is positioned adjacent to the lower nose prong ramp 172 and the upper nose prong 113 is positioned adjacent to the upper nose prong ramp 164. Then, the pusher 112 can be guided down each of these respective ramps into the pusher recess 171. This movement of the pusher 112 into the pusher recess 171 can be reversed thereby moving the pusher 112 from the pusher recess 171 and into an engaged state.

FIG. 14B is a sectional view from a nail-side 58 angle of the magazine which illustrates the pusher 112 transitioning from a retracted state to an engaged state as the upper nose prong 113 is guided by an upper nose prong ramp 164 and the lower nose prong 120 is guided by a lower nose prong ramp 172. This disclosure is not limited as to the number of guides and ramps employed to allow transition of the pusher assembly between and engaged state and retracted state and vice versa. The pusher 112 can have a broad variety of designs and embodiments. This application is not limited to the presence, absence or number of nose prongs. Broadly, in an embodiment, a portion of the pusher 112 pushes a nail 57.

The pusher assembly 110 can be transitioned from a retracted state to an engaged state simultaneously with the pusher 112 moving out of the pusher recess 171 and into an engaged state. Like reference numbers in FIG. 14A identify like elements in FIG. 14B.

FIG. 14C is a sectional view from a nail-side 58 angle of the magazine 100 illustrating the pusher assembly 110 transitioning from a retracted state to an engaged state as the upper nose prong 113 is guided by an upper pusher guide 162 into the nail track 111 where the pusher 112 engages the nail 57, the lower nose prong 120 is guided by a lower pusher guide 170 and the lower base prong 122 is guided by a lower base prong ramp 178 into the nail track 111. Thus, the pusher 112 can be guided into an engaged state from a retracted state. In the reverse of this method, the pusher 112 can be guided into a retracted state from an engaged state. Like reference numbers in FIG. 14A identify like elements in FIG. 14C.

FIG. 14D is a sectional view from a nail-side 58 angle of the magazine illustrating the pusher in an engaged state as the upper nose prong 113 is guided by an upper pusher guide 162 in the nail track 111, the lower nose prong 120 is guided by a lower pusher guide 170 and the lower base prong 122 is guided by a lower base prong guide 176. Like reference numbers in FIG. 14A identify like elements in FIG. 14D.

FIG. 15 is a nail-side 58 sectional view of the magazine 100 illustrating the pusher 112 in an engaged state. The upper nose prong 113 is guided by an upper pusher guide 162, the lower nose prong 120 is guided by a lower pusher guide 170 and the lower base prong 122 is also guided by the lower pusher guide 170. The spring 200 is biased toward the pusher track nose end 190 and pushes the pusher 112 against the plurality of nails 55 to be fed to the nosepiece assembly 12 for driving. Like reference numbers in FIG. 14A identify like elements in FIG. 15. The nail 53 is a nail of the plurality of nails 55. The pusher 112 can be stopped by a mechanical stop or a lockout 500 from forward motion at the pusher track nose end 190.

The lockout 500 is an optional feature of a magazine 100. The lockout 500 can cause a locked out state (also herein as "locked out") of the nailer 1 when no nails, or a predetermined number of nails, are present in the magazine.

In an embodiment, the lockout 500 can inhibit the movement of the upper contact trip 310 when a predetermined number of nails (or zero (0) nails) are present in the magazine. This inhibition of movement of the upper contact trip 310 when the lockout 500 is in a locked out state (also as "lockout" state) can make an operator aware that a nail is not going to be driven and that it is appropriate to reload nails or to add more nails into the magazine 100. This feature can be used in all modes of operation of a fastening tool, e.g. nailer, including but not limited to sequential and bump modes.

For example in bump mode, an operator can drive a series of nails until a predetermined number of nails (or zero (0) nails) are present in the magazine at which condition the lockout 500 engages and inhibits the movement of the upper contact trip 310 preventing and/or inhibiting a nail 53 from being driven. This circumstance can indicate to the operator that it is appropriate to add one or more nails to the magazine.

A lockout state can prevent firing when a predetermined number of nails, or no nails, remain in the magazine 100. If a nailer were to fire with no nail present in the nosepiece, then the energy expended in the attempt to drive a missing nail would be absorbed by the fastening tool and would subject the fastening tool to an unwanted physical shock. Additionally, without the lockout 500, an operator could use the fastening tool under a false assumption that fasteners were being driven, when they were not actually being driven.

A predetermined number of nails can be chosen so as to maintain a bias from the spring 200 on the pusher 112. This maintaining of the bias on the pusher 112 can be achieved by providing a number of nails which the pusher 112 can push on which keeps an amount of tension on the spring 200. In an embodiment, a lockout state can occur when a number of nails in a range of from 0 to 20 nails are present in the nail track 111. In an embodiment, a lockout state occurs when 3 or fewer nails are present in the nail track 111. In an embodiment, a lockout state occurs when 5 or fewer nails are present in the nail track 111. In an embodiment, a lockout state occurs when 8 or fewer nails are present in the nail track 111.

This disclosure encompasses means for pushing a fastener for driving by a fastening tool. A broad variety means for pushing a fastener (e.g. a nail) in a magazine are intended to be within the scope of this application. For example, a pusher 112 can have a variety of designs and can employ various shapes, prongs and surfaces to push one or more of the plurality of nails 55. This disclosure is not limited regarding means for guiding the pusher 112 or the plurality of nails 55. Additionally, this disclosure is also to be broadly construed regarding disclosed means for achieving a recess of pusher 112.

Further, this disclosure encompasses methods for pushing and moving fasteners, e.g. nails, as disclosed herein. Additionally, this disclosure encompasses methods for achieving a recessed state of the pusher assembly 110, or a recessed state of pusher 112, as disclosed herein.

Figure 15A:
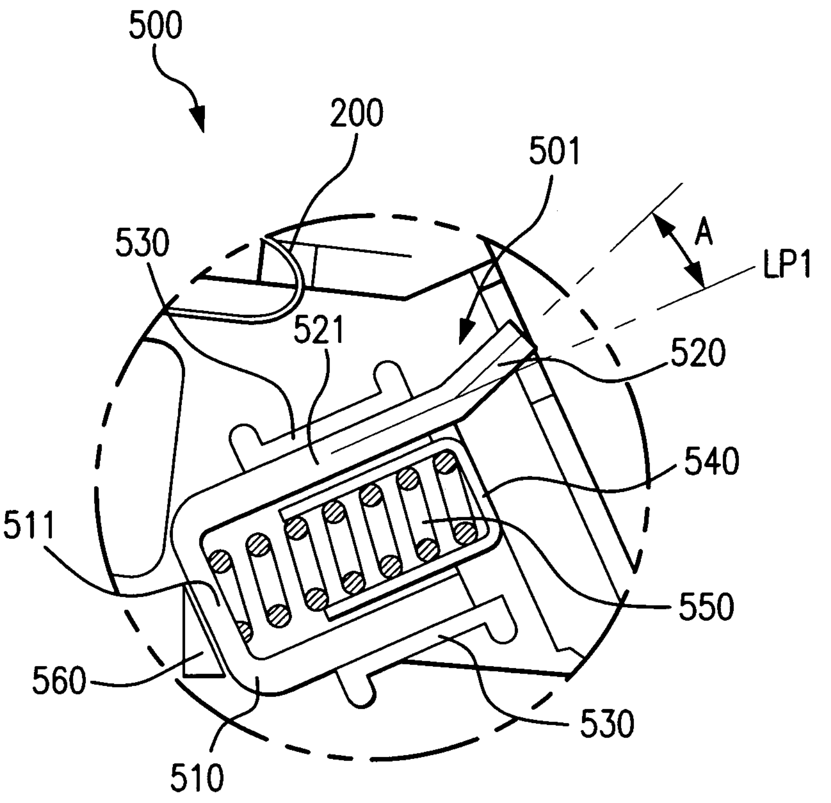
FIG. 15A is a nail-side detail view of the lockout mechanism.

FIG. 15A is a nail-side detail view of an embodiment of a lockout 500 which is an "angled lockout". An angled lockout has a locking leg 520 which does not meet a contact trip at a perpendicular angle to the direction of motion of the contact trip (e.g. FIGS. 15G-15L). The lockout 500 has a lock 510 with a lock base end 511. In the illustrated embodiment of FIG. 15A, the lockout 500 is an angled lockout 501 having the locking leg 520 with an angle A. In an embodiment, the angle A is 27° from a plane LP1 of an upper lock portion 521.

A lock guide 530 can guide the movement of the lock 510 to a predetermined direction when it is pushed by a lockout pusher 570 of the pusher 112. The lockout 500 uses a lockout spring 550 which can sit in a lock spring seat 540 to bias the lock 510 toward a lock stop 560. In an embodiment, the lock spring seat 540 can be an extruded rib feature of the magazine 100.

In an embodiment, the lockout 500 uses a retaining clip, or lockout mechanism cover, to maintain the lock 510 positioned in coordination with the lock guide 530. In another embodiment, the lock 510 is positioned in coordination with the lock guide 530 by fit within the magazine 100. In an embodiment, the spring 200 is fixed to the magazine 100 at a location which can be a value of distance to the lockout 500 in a range of from 1 mm to 30 mm, for example e.g. 15 mm or less.

Figure 15B:
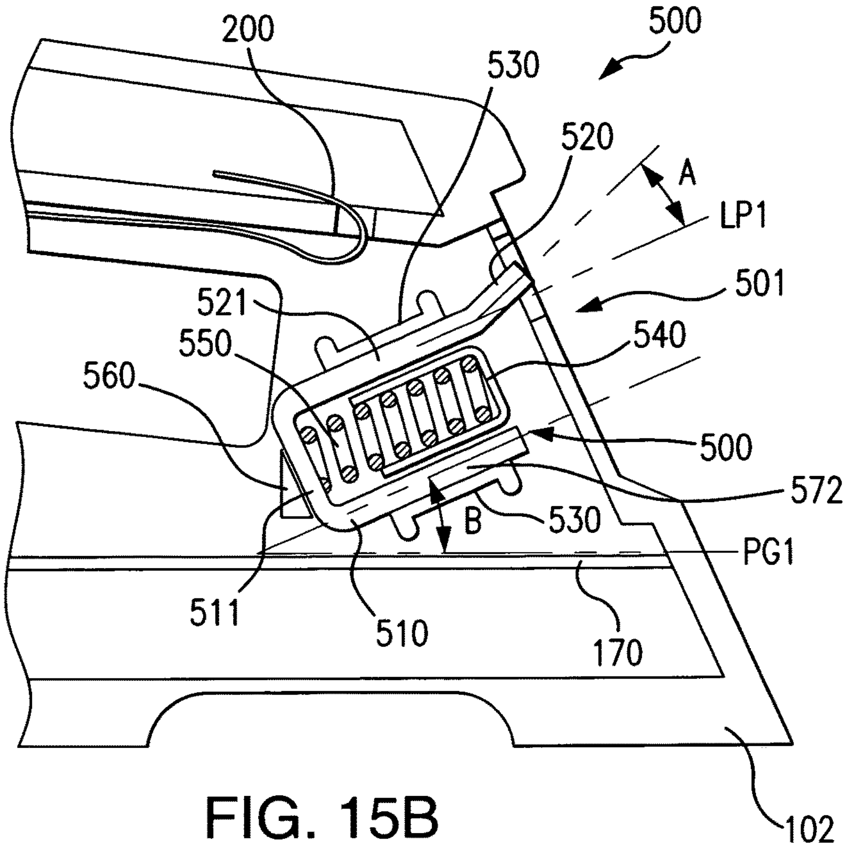
FIG. 15B is a nail-side detail view of the lockout mechanism in a retracted state.

FIG. 15B is a detail view of the lockout 500 in a retracted state. FIG. 15B illustrates an embodiment of the angled lockout 501 which uses a lock 510 having a locking leg 520 which has an angle A of 27° as measured from the plane LP1. In other angled lockout embodiments, the angle A can have another value. The angled lockout 501 of FIG. 15A can be set at an orientation in which lower lock portion 572 has an angle B of 31.5° from a plane PG1 of the lower pusher guide 170. Like reference numbers in FIG. 15B indicate like elements of FIG. 15A.

Figure 15C:
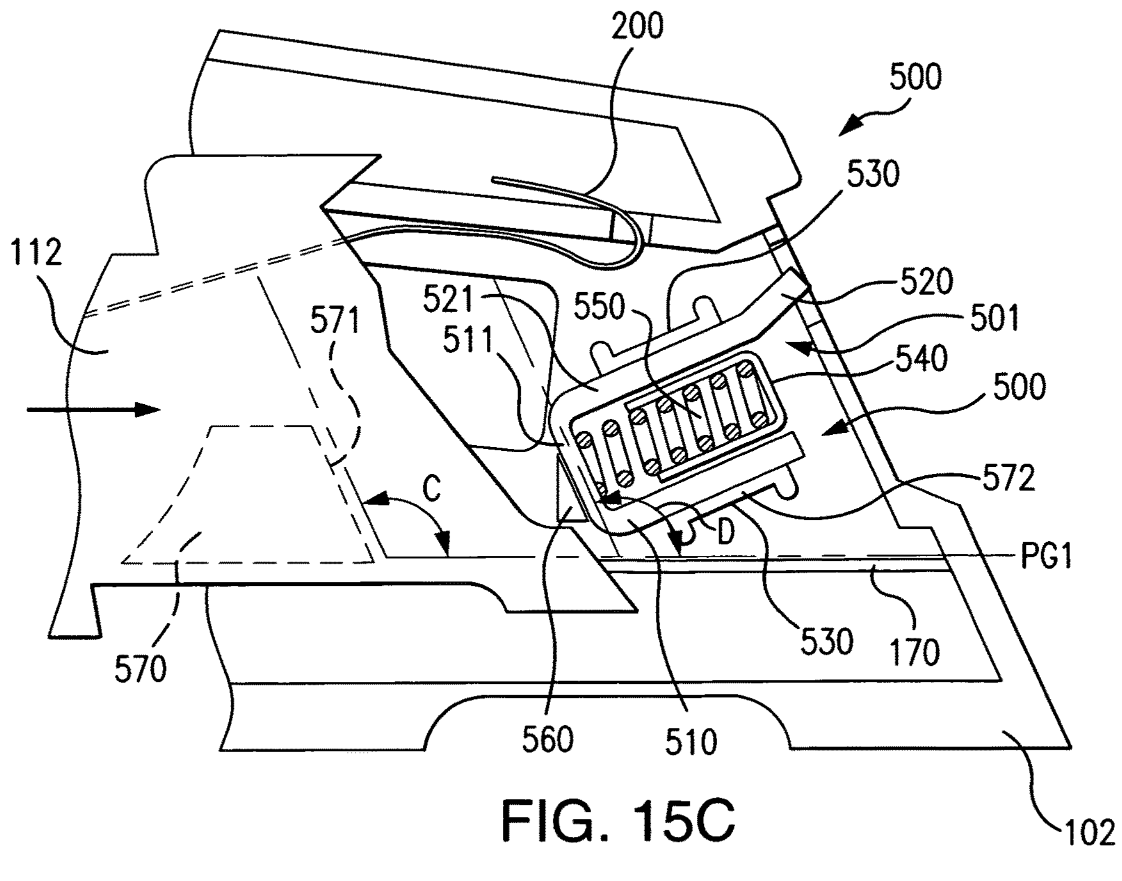
FIG. 15C is a nail-side detail view of the lockout mechanism in a retracted state as a pusher moves toward it.

FIG. 15C is a nail-side detail view of the lockout 500 in a retracted state as the pusher 112 moves toward it. FIG. 15C illustrates the pusher 112 having a lockout pusher 570 which has a lockout pusher face 571. The pusher 112 is illustrated moving forward toward the lockout 500. In this embodiment, the lock 510 has a lockout base end 511 which has an angle D of 121.5° from the plane PG1 of the lower pusher guide 170. The lockout pusher 570 has a lockout pusher face 571 which also has an angle C of 121.5° from the plane PG1 of the lower pusher guide 170. The lockout pusher face 571 can move behind the lockout base end 511, push up against it so that the lockout pusher face 571 fits against the lockout base end 511 and can push the lock 510 toward the nose end 102 and against the bias of the lockout spring 550. Like reference numbers in FIG. 15C indicate like elements of FIG. 15A.

Figure 15D:
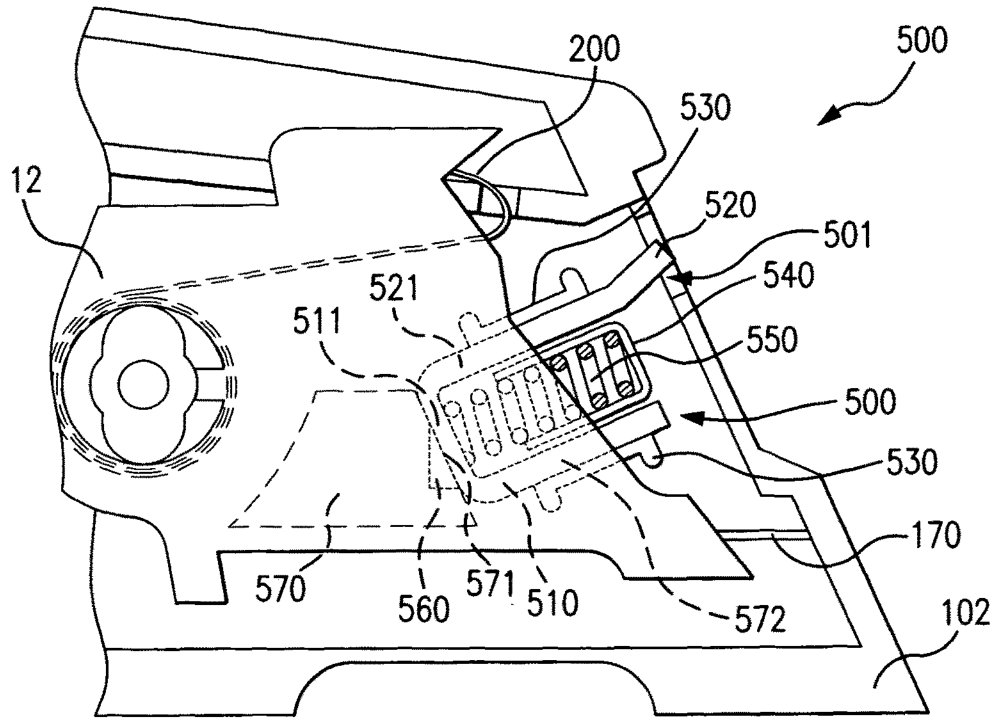
FIG. 15D is a nail-side detail view of the lockout mechanism in a retracted state as the pusher contacts a lock base end of the lockout mechanism.

FIG. 15D is a perspective view of the lockout 500 in a retracted state as the pusher 112 contacts a lock base end 511 of the lockout 500. FIG. 15D illustrates that the lockout pusher 570 having the lockout pusher face 571 has cleared over the lock stop 560 and illustrates the lockout pusher face 571 pressing against the lockout base end 511. Like reference numbers in FIG. 15D indicate like elements of FIG. 15A.

Figure 15E:
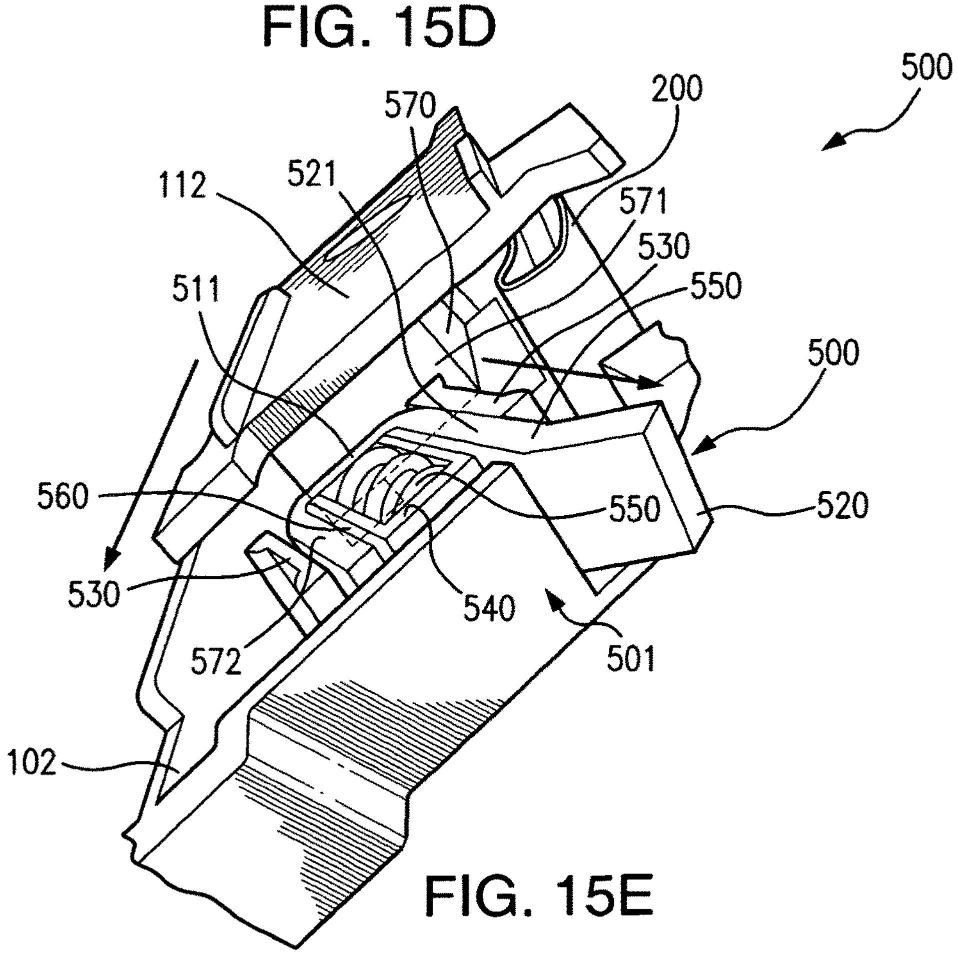
FIG. 15E is a perspective view of the lockout mechanism as it is pushed into an engaged state.

FIG. 15E is a nail-side detail view of a lockout mechanism 500 as it is transitioned into an engaged state. FIG. 15E is a perspective view illustrating the movement of the lock 510 which occurs when the lockout pusher 570 clears over the lock stop 560 and the lockout pusher face 571 presses against the lockout base end 511. By this action, the lockout pusher 570 pushes the lockout 500 toward the nose end 102 of the magazine 100. When the lockout 500 moves toward the nose end 102 of the magazine 100, the locking leg 520 moves (e.g. FIG. 15E) to protrude out of the nose end 102 of the magazine 100 into a position to block the motion of the upper contact trip 310. Like reference numbers in FIG. 15A indicate like elements of FIG. 15E.

Figure 15F:
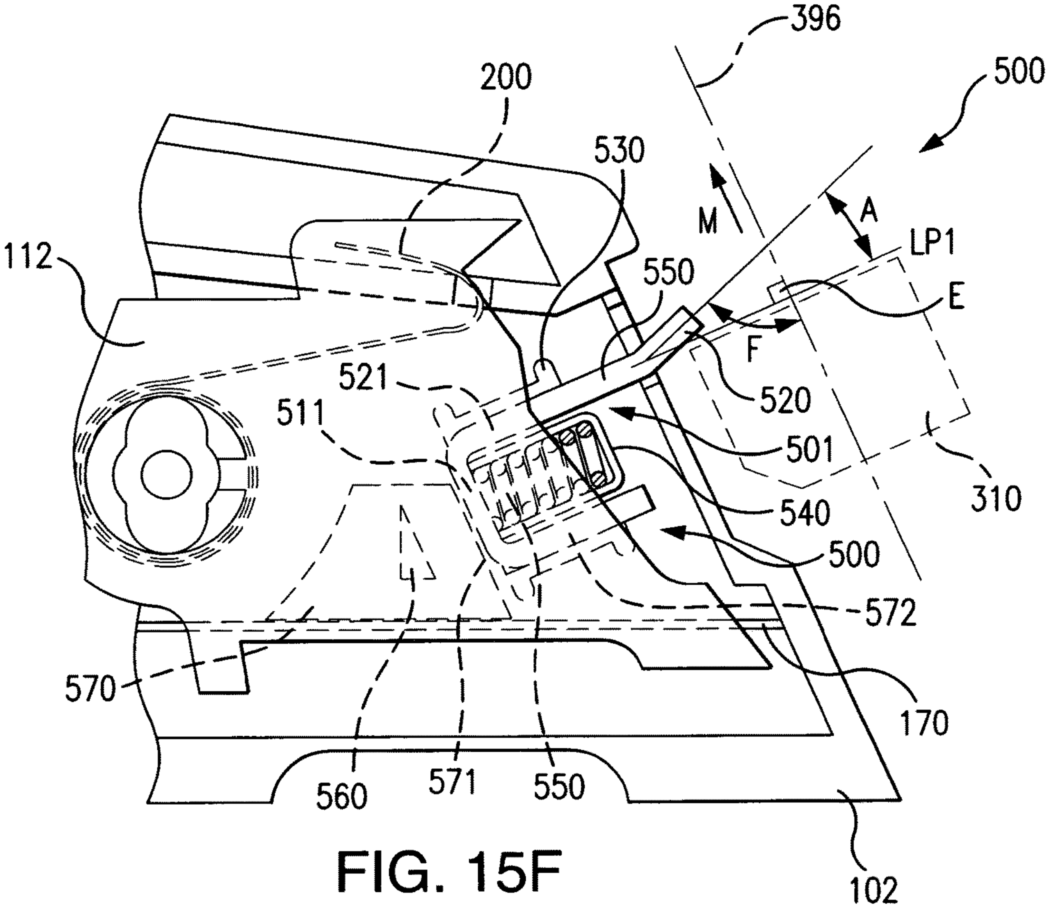
FIG. 15F is a nail-side detail view of the lockout mechanism in a locked out state.

FIG. 15F is a nail-side detail view of the lockout mechanism 500 in a locked out state. FIG. 15F illustrates the locked out configuration of the lockout 500. FIG. 15F illustrates a state of the fastening device that is locked out. In a locked out state, the locking leg 520 inhibits the upper contact trip 310 from moving to activate the driving of a nail. The inhibition of the movement of the upper contact trip 310 also can indicate to an operator that a reloading of nails can be appropriate. The amount of inhibition to the movement of the upper contact trip 310 by the locking leg 520 can be different in different embodiments. For example, in an embodiment, the locking leg 520 can prevent the movement of the upper contact trip 310 toward the nose plate 331 (e.g. FIG. 15G). In other embodiments, the lockout can be set such that when the locking leg 520 experiences an amount of force from the upper contact trip 310, the locking leg 520 can be pushed in a direction away from the nose end 102 and can move away from the direction of the nose end 102. This allows the upper contact trip 310 to move the locking leg 520 allowing the upper contact trip 310 to continue to move toward the nose plate 331. In an embodiment, a portion of the upper contact trip 310 can move past the locking leg 520 toward the nose plate 331 when the locking leg 520 is moved away from the direction of the nose end 102 allowing the portion of the upper contact trip 310 to pass.

In the example embodiment illustrated in FIG. 15F, the lockout 500 is an angled lockout 501 having a locking leg

520 with the angle A which is 27° from the plane LP1 of the upper lock portion 521. FIG. 15F also illustrates an upper contact trip 310 having a direction of motion M and an angle F of 63° from the direction of motion M when the plane LP1 of the upper lock portion 521 is perpendicular to the direction of motion M such that an angle E has a value of 90°. Other values of the angle E may be used, for example the angle E can have a value in a range of 45° to 165°, e.g. 75° or 135°. When other values of the angle E are used, the angle F and the angle A can also have other values.

In an embodiment, the lockout 500 can be set to provide a resistance of 50 lbf against the motion of the upper contact trip 310. When the upper contact trip 310 imparts a force against a portion of the locking leg 520 greater than the 50 lbf of resistance provided by lockout 500, then the upper lock portion 521 can be pushed away from the upper contact trip 310. In an embodiment, a force applied to a lower trip 320 can also provide force to the upper contact trip 310 large enough to overcome the friction and spring forces on the upper lock portion 521 and can move the locking leg 520 and allow a portion of the upper contact trip 310 to pass by the locking leg 520. In an embodiment, a 27° value of the angle A (e.g. FIG. 15A-15B) is sufficient to provide a resistance of 50 lbf against the motion of an upper contact trip 310 and allow a lockout. The resistance force against the motion of the upper contact trip 310 can be selected from a wide range of values and can be a small or large number. For non-limiting example, the resistance force can be 25 lbf, 75 lbf, 100 lbf, 200 lbf, 250 lbf or 300 lbf, or even greater. The resistance force can be a value in a range of from e.g. 15 lbf to 400 lbf.

In an embodiment, the center of gravity of the tool can be positioned collinearly with axis 396 such that when dropped, the tool can land in a manner causing the lower contact trip to impact the surface onto which the too is dropped and lockout 500 can mitigate the force of the impact on the nosepiece assembly 12.

The movement of the locking leg 520 to allow a portion of the upper contact trip 310 to move by the locking leg 520 is referred to herein as a "lockout override". A lockout override is a feature or action which can limit the bending stress upon the nosepiece assembly 12 resulting from a drop, or other application of force. For example, it can protect the individual components constituting the fixed nosepiece assembly 300 from such an application of force. A lockout override can occur when an override force is reached. An override force is a force able to move the locking leg 520 such that a lockout override can occur. For example, if a force is experienced by lockout leg 520 which can override the 50 lbf of resistance provided by lockout 500 then a lockout override can occur. Such a force would be a lockout override force. A wide range of values for the lockout 500 resistive force can be used. Likewise, a wide range of values for an override force can be used. An override force can be set by considering criteria such as but not limited to the strength of the nosepiece elements of the tool, the sensitivity of the triggering elements, the desired feel and use of the equipment as well as other factors. If an override force is reached, a rod stop 348 of the depth adjustment rod 350 can be moved to meet an upper stop 390 (e.g. FIGS. 15G-15L). In an embodiment, the lockout 500 is an angled lockout 501 having a locking leg 520 with an angle A set such that a force greater than the 50 lbf of resistance provided by lockout 500 is applied upon locking leg 520.

In an embodiment an override force is applied to locking leg 520 in a direction which perpendicular to a direction of motion M (FIG. 15F) and also normal to the axis of operation AO (e.g. FIG. 15G). A force from an upper contact trip upon 310 upon a locking leg 520 can be applied at a wide variety of angles consistent with achieving a desired override force and/or resistance for lockout 500.

In other embodiments, the lockout 500 can be designed having a contact face or contacting portion which can be angled or which otherwise interacts with a contact trip element to allow a lockout override to occur when an override force is applied to the contact trip element. An override force can have a value selected from a wide range, such as for non-limiting example a value in a range of from, for example 25 lbf to 300 lbf, e.g. 50 lbf or 51 lbf.

FIG. 15G is a nail-side detailed view of an embodiment of the lockout 500 in a locked out state and the upper contact trip 310 in a position not in contact with the lockout mechanism. FIG. 15G illustrates the locked out configuration of the angled lockout 501. FIG. 15G illustrates the upper contact trip 310 positioned on the nose tip 333 side of the locking leg 520.

FIG. 15G is a detail of a lockout 500 of an embodiment of the nailer 1 as illustrated in e.g. FIGS. 1A, 1A and 2. In this example embodiment, FIGS. 15G-15L illustrate a nosepiece assembly 12 which is a fixed nosepiece assembly 300. The fixed nosepiece assembly 300 has a nosepiece shaft 370 which extends from the nose plate 331 to overlap at least a portion of the interface seat 425 (e.g. FIG. 2A) to at least allow for connection of a nosepiece insert screw 401 and cover at least a portion of the interface seat 425 (e.g. FIG. 2A). In another embodiment the nosepiece shaft 370 can extend to insert tip 355.

FIG. 15G illustrates an upper contact trip 310 slidably mounted on the nosepiece shaft 370. In an embodiment, the activation rod 403 (e.g. FIG. 15I) is connected to the upper contact trip 310 to allow the activation rod 403 to move in coordination with the movement of the upper contact trip 310. The example of FIG. 15G illustrates the upper contact trip 310 also connected to a pin plate 342. When the pin plate 342 moves toward the nose plate 331, the upper contact trip 310 also moves toward the nose plate 331. The depth adjustment wheel 340 is illustrated as coaxial and covering a portion of the depth adjustment rod 350.

The example of the depth adjustment rod 350 illustrated in FIG. 15G has three segments of different diameters. The first is a spring base portion 344 of the depth adjustment rod 350. The second is a rod stop portion 346 having a rod stop 348. The third is an upper pin 349. The upper pin 349 passes through an opening in the upper stop 390 against which the rod stop 348 can reversibly contact. The upper pin 349 can pass through an opening in an insert boss 392 which in an embodiment, extends through the upper stop 390. Thus, the upper pin 349 has a length which passes through respective openings in the upper stop 390, and the insert boss 392 which passes through the nose plate 331 to enter an upper pin cavity 394. This configuration allows for the upper pin 349 to reversibly move in coordination with the upper contact trip 310. As the upper contact trip 310 moves toward the nose plate 331, a greater portion the length of the upper pin 349 enters the upper pin cavity 394. As the upper contact trip 310 moves away from the nose plate 331, then a lesser portion of its length is present in the upper pin cavity 394.

In the embodiment of FIG. 15G, the contact trip spring 330 can be placed coaxially with the depth adjustment rod 350 such that the contact trip spring 330 coils surround or encompass at least a portion of the depth adjustment rod 350 and the contact trip spring 330 can be located between the pin plate 342 and the upper stop 390.

Figure 15H:
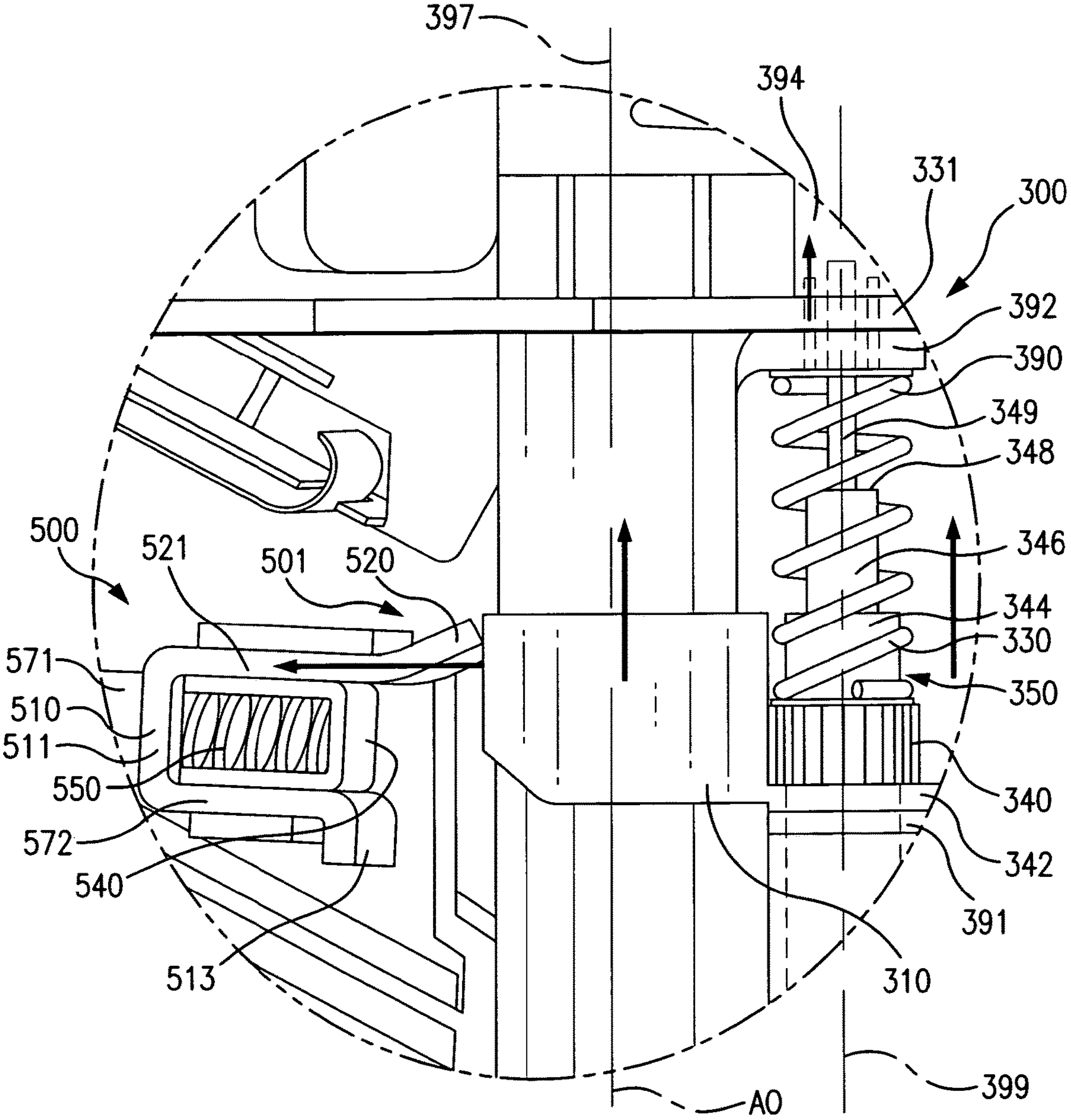
FIG. 15H is a nail-side detailed view of the upper contact trip contacting and pushing back a locking leg of the lockout mechanism.

The spring 200 is biased to provide a motive force to the pusher assembly 110 to push the lockout 500 into a locked out configuration as illustrated in FIG. 15H.

FIG. 15G illustrates a lockout 500 in a locked out configuration. In this embodiment, the lockout 500 is an angled lockout 501. The angled lockout 501 has an of the upper lock portion 521 with the locking leg 520 having the angle A. The angle A can be a wide range of angles. In this example, the angle A can be 27° from the plane LP1. In this example, the angle B can be 31.5° measured from plane PG1. The axis of operation AO in FIG. 15G of the upper contact trip 310 can be the same as that of the lower contact trip 320. In an embodiment, the axis of operation AO is collinear with a centerline 397. A force can be placed upon locking leg 520 which has been communicated via a contact trip such as that the lower contact trip 320 or the upper contact trip 320. An impact or force upon the lower contact trip 320 or the upper contact trip 320 can be collinear with AO, but can also be from other angles which are not collinear with AO.

The angled lockout 501 can use the lock 510 which has the upper lock portion 521 and the lock base end 511. The lockout pusher 571 of the pusher 112 is illustrated pushing up against the lock base end 511 in a direction toward the nosepiece shaft 370 (e.g. 15G-L) and against the bias of the lockout spring 550 which is located in the lock spring seat 540. FIG. 15G also illustrates the lower lock portion 572 optionally having a lower lock end 513.

In an embodiment, the upper contact trip 310 can be stopped against a down stop 391. In an embodiment, this position can be referred to as the "home" or "resting" position. In FIG. 15G, the pin plate 342 to which the upper contact trip 310 can be connected is stopped from downward motion by the down stop 391.

In an embodiment, the contact trip spring 330 can have a bias toward the down stop 391 (which can be a preload force) of 8.75 lbf bias toward the down stop 391. This can be the bias toward the down stop 391 when the tool is static and at rest. A wide range of values of bias toward the down stop 391 can be used, e.g. a value in a range of from 1 lbf to 25 lbf. When the nose tip 333 is pressed against e.g. a workpiece, the upper contact trip 310 and the pin plate 342 experience a force along the operating axis toward the nose plate 331. As the upper contact trip 310 and the pin plate 342 can move toward the nose plate 331 under force. In an embodiment, the spring compression can reach 12.5 lbf at the upper stop 390.

In an embodiment, a contact trip spring 330 can experience a compression force of 12.0 lbf. This compression force of 12.0 lbf can be experienced when the fastening tool is operating in sequential, bump or other modes.

In an embodiment, the compression force upon the contact trip spring 330 can be 1.25 times the weight of the tool as determined when the tool is not loaded with nails and the battery is reversibly attached to the tool to allow triggering of the driving or firing of a fastener. The ratio of a compression force upon the contact trip spring 330 to the weight of a fastening tool with no fasteners and a battery attached if a battery is used with the fastening tool can be a ratio in the range of from 1:1 to 5:1, such as for example 1.5:1 or 2.0:1 to allow triggering of the driving or firing of a fastener. The compression force ratios can be applied to a fastening tool not employing a battery as a power source.

In an embodiment, 12 mm of movement or less of an upper contact trip 310 can occur from an at rest position having no pressure from a workpiece upon the lower contact trip 320 to a compressed state of the contact trip spring 330 which can result in a fastener being driven.

The contact trip spring 330 can have a spring length SL (FIG. 15G) which is reduced when the contact trip spring 330 is compressed. In an embodiment, when compressed to trigger the driving of a nail, the spring length SL can be reduced by 12 mm. The reduction of spring length SL during a compression of the contact trip spring 330 to trigger the driving of a nail can have a wide range of values, for example the spring length SL can be reduced in a range of from 7.5 mm or less to 15 mm or greater for each compression leading to a nail being driven.

In an embodiment, 12 mm of movement or less can occur to upper pin 349 from an at rest position for a compression of the contact trip spring 330 which results in a nail being driven.

In an embodiment, a nosepiece length NL (FIG. 2A) can be reduced by 12 mm or less during a compression of the contact trip spring 330 leading to a nail being driven. The reduction of the nosepiece length NL during a compression of the contact trip spring 330 leading to a nail being driven can have a wide range of values, for example the reduction of the nosepiece length NL can range from 7.5 mm or less to 15 mm or greater during a compression leading to a nail being driven. In an embodiment, the reduction of nosepiece length NL can be 12.5 mm. In an embodiment, the reduction of the nosepiece length NL can be equal to the reduction of the spring length SL, for example 12.5 mm, or 12 mm. In an embodiment, the reduction of nosepiece length NL can be 12.5 mm during bump or sequential modes.

FIG. 15G1 is a nail-side detail view of an upper stop 390 having a bushing 389. FIG. 15G1 also illustrates a contact trip spring 330, an insert boss 392, a nose plate 331 and an upper pin 349. Like reference numbers in FIG. 15G identify like elements in FIG. 15G1.

FIG. 15H is a nail-side detailed view of the upper contact trip contacting and pushing back the locking leg 520 of the lockout 500. FIG. 15H illustrates that when the upper contact trip 310 is forced along an axis of operation AO toward the nose plate 331, then the lock 510 having the locking leg 520 is pushed away from the nosepiece shaft 370 such that a portion of the upper contact trip 310 can move beyond the locking leg 520 toward the nose plate 331. Like reference numbers in FIG. 15G identify like elements in FIG. 15H.

Figure 15I:
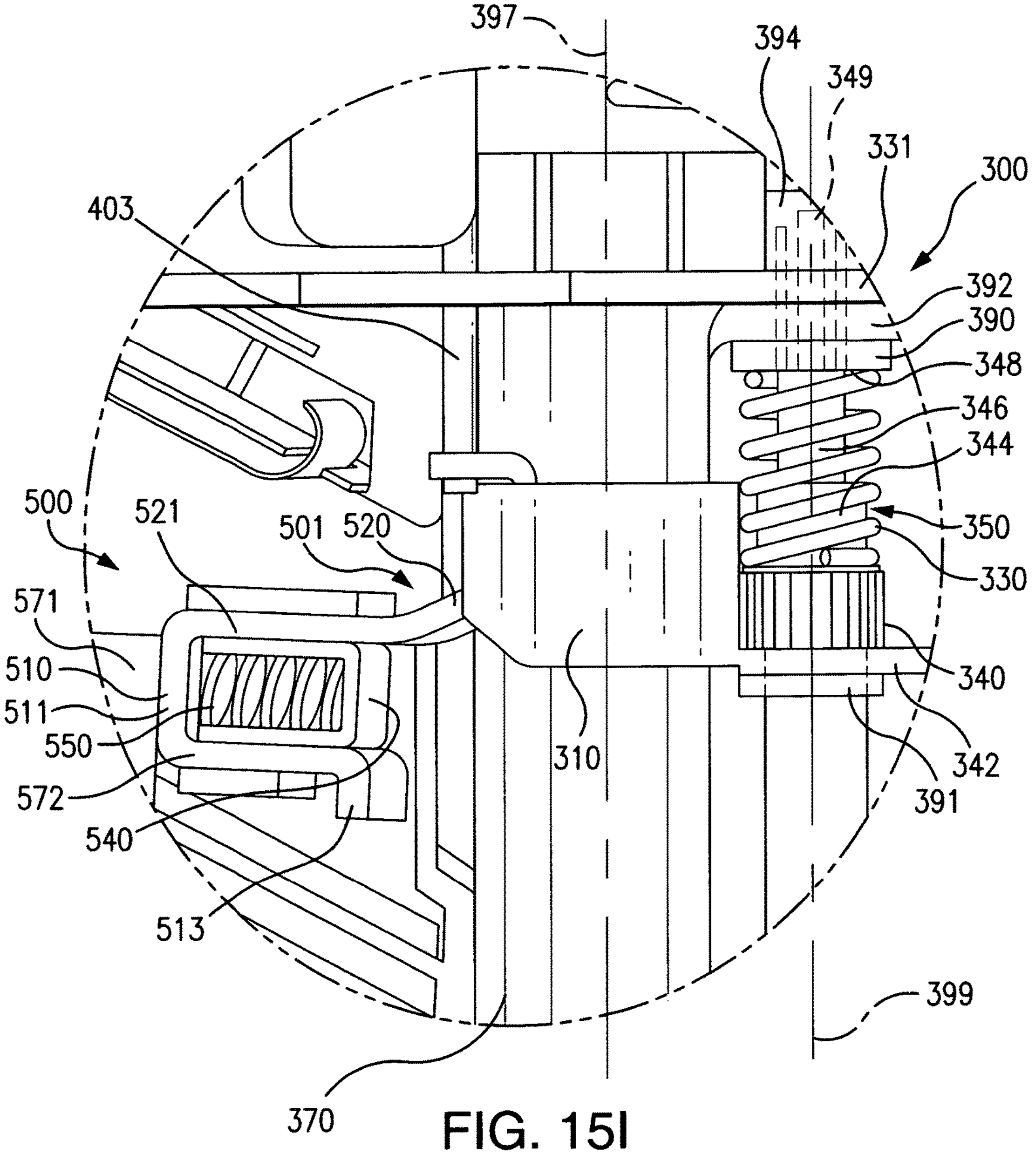
FIG. 15I is a nail-side detailed view of the upper contact trip in an up-stopped position having pushed back the locking leg of the lockout mechanism.

FIG. 15I is a nail-side detailed view of the upper contact trip 310 in an up-stopped position or override state after the upper contact trip 310 has pushed back the locking leg 520 of the lockout 500 and moved to the upper stop 390. FIG. 15I illustrates when the locking leg 520 pressing against the upper contact trip 310 of which a portion has moved beyond the locking leg 520 toward the nose plate 331. In an up-stopped position, the rod stop 348 is stopped by the upper stop 390. Like reference numbers in FIG. 15G identify like elements in FIG. 15I.

Figure 15J:
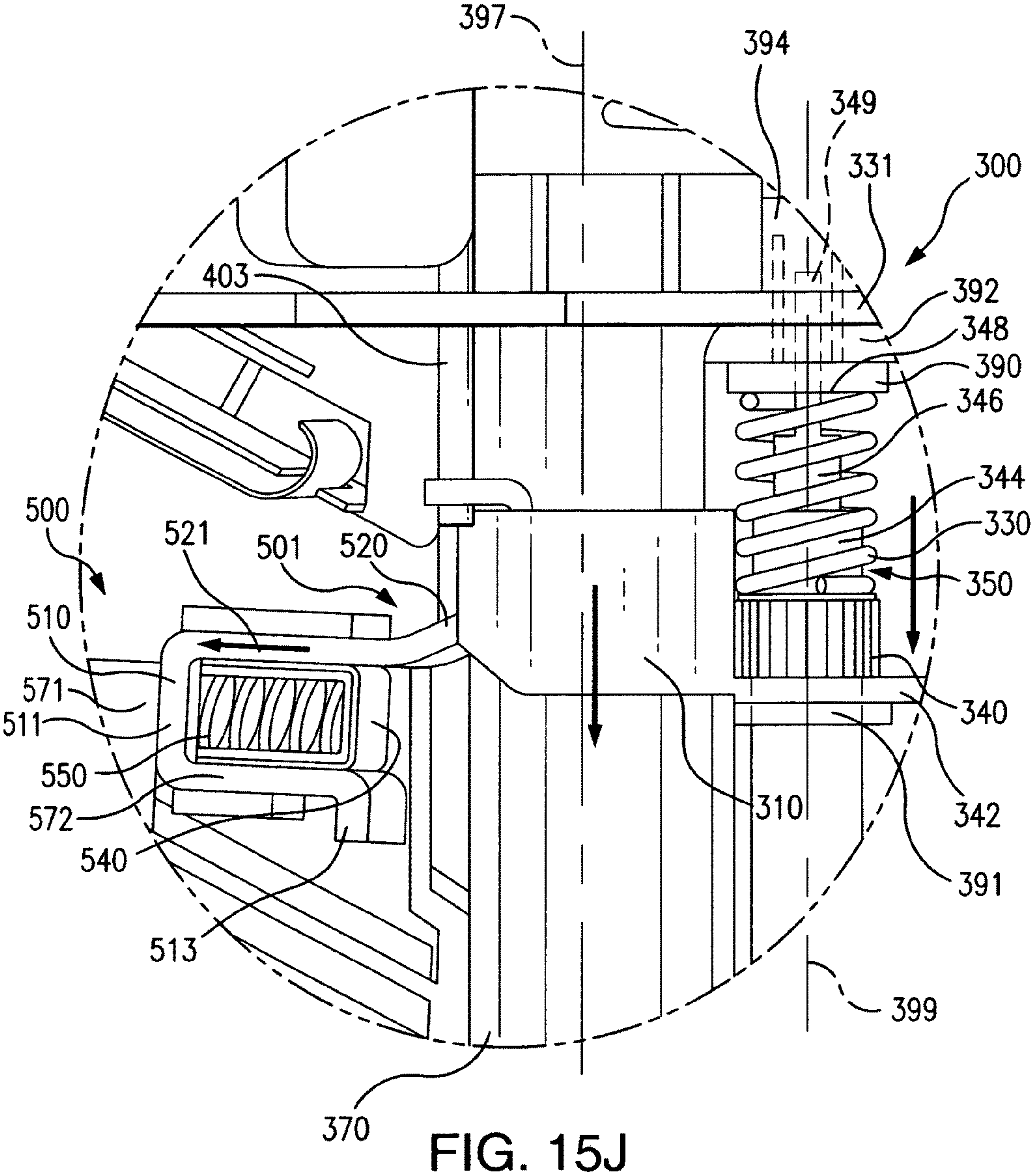
FIG. 15J is a nail-side detailed view of the upper contact trip returning from an up-stopped position.

FIG. 15J is a nail-side detailed view of the upper contact trip returning from an up-stopped position to a position not in contact with the lockout mechanism. FIG. 15J illustrates when the locking leg 520 is pressing against the upper contact trip 310 of which a portion has moved beyond the locking leg 520 toward the nose plate 331. FIG. 15J illustrates the movement of upper contact trip away from the nose plate 331 at least in part as a result of the bias of the contact trip spring 330. Like reference numbers in FIG. 15G identify like elements in FIG. 15J.

Figure 15K:
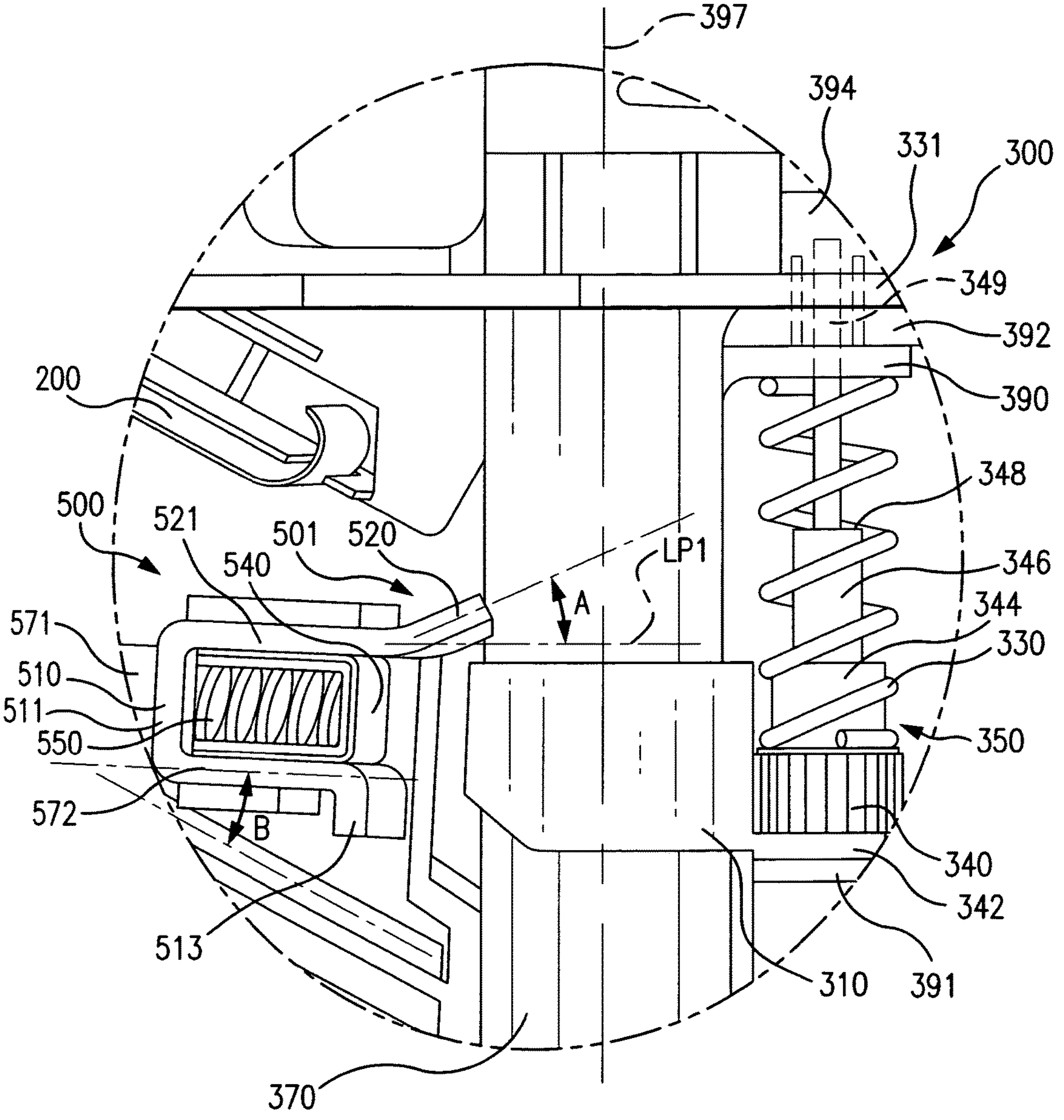
FIG. 15K is a nail-side detailed view of the upper contact trip having returned from contact with the lockout mechanism to a state again having no contact with the lockout mechanism.

FIG. 15K is a nail-side detailed view of the upper contact trip which has returned from contact with the lockout 500 to a state again having no contact with the lockout 500. FIG. 15K illustrates the locking leg 520 having returned to a locked out configuration of the angled lockout 501. FIG. 15K illustrates the upper contact trip 310 having returned to the nose tip 333 side of the locking leg 520. FIG. 15K illustrates the upper contact trip 310 and the locking leg 520 having returned to positions as depicting in FIG. 15G. It can be characterized that the upper contact trip 310 has returned to its home position as illustrated in FIG. 15G. Like reference numbers in FIG. 15G identify like elements in FIG. 15K.

Figure 17A:
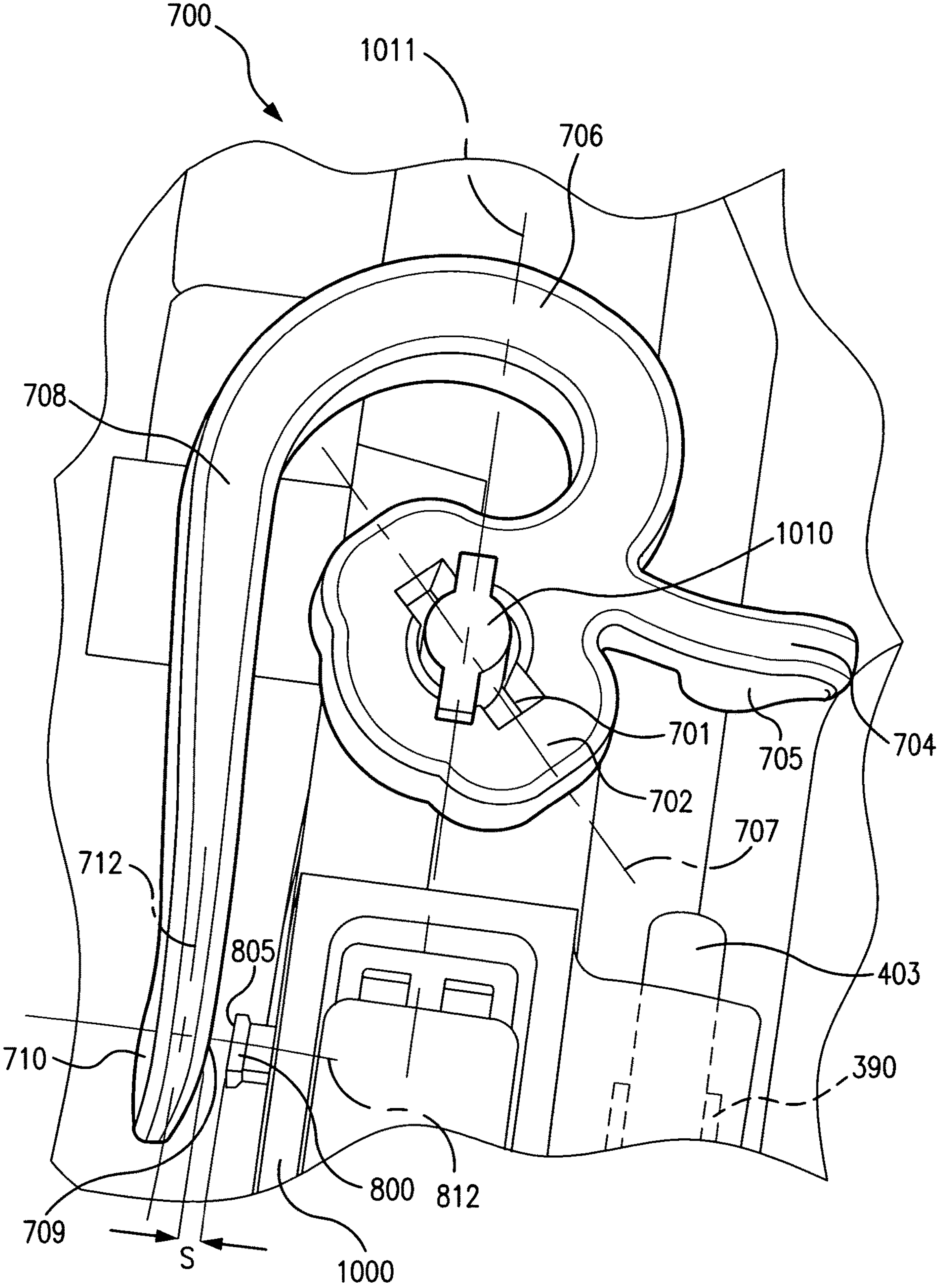
FIG. 17A illustrates an embodiment of a contact trip actuator.

A trip stop can be a stop which, when engaged or activated, prevents actuation of a contact trip or contact trip actuator, such as for example a contact trip actuator 700 (e.g. FIG. 17A). A contact trip can also be another means of preventing actuation of the driving of a loaded nail 53, such as a mechanical or electronic stop or interruption of an actuation of a contact trip actuator. In an embodiment, a nailer can have a trip stop and/or an upper stop 390 and a lockout 500.

FIG. 15L is knob-side view of pusher 310 in a down-stopped position and not in contact with the lockout mechanism. Like reference numbers in FIG. 15G identify like elements in FIG. 15L.

As illustrated in FIG. 15L, using a down stop 391 can achieve an on-axis stop point 395 along a centerline 399 which can be parallel to the centerline 397. The stop point 395 can be a point along a plane AS which can be perpendicular to the axis of operation AO. Axis of operation AO can optionally be collinear with the centerline 397 as illustrated by an angle F illustrated in FIG. 15L. In this example, angle F can be 90°. The down stop 391 can provide the on-axis stop point 395. This configuration of the down stop 391 and the on-axis stop point 395 can align the downward forces upon a pin plate 342 in a direction parallel to the centerline 399 and which can be parallel in direction to the centerline 397. This configuration can improve fastening tool performance and can improve the wear characteristics of the nosepiece assembly 12. Additionally, this configuration also improves the stability of the nosepiece assembly 12. For non-limiting example this configuration can reduce rocking and undesired movement of the upper contact trip 310 when moving or in contact with the down stop 391.

Stop point 395 can be positioned at a distance along the centerline 399 or the centerline 397 which intersects with a plane AS. The plane AS can be positioned at a location between the down stop 391 and the upper stop 390 at which position the upper contact trip 310 has an available distance to move to trigger the driving or firing of a fastener, e.g. a nail.

FIG. 16 is a sectional view from the nail-side 58 of the magazine 100 illustrating the pusher 112 in an engaged state and in which the pusher 112 has fed all of the plurality of nails 55 to the nosepiece assembly 12. In FIG. 16, the lockout 500 is in a locked out state (also herein as "locked out"). Like reference numbers in FIG. 14A identify like elements in FIG. 16.

This disclosure is to be broadly construed to encompass means to prevent undesired driving or firing of a fastener, e.g. a nail, by using a lockout or lockout mechanism. The means for achieving lockout can be using multiple locks, latches and other means of inhibiting the movement of a contact trip. Additionally, a lockout from firing can be achieved by electronic or software means. Means for physically protecting the nose also include but are not limited to lockout mechanisms which can be located in the nosepiece, magazine, or which have components distributed in both the nosepiece and magazine.

This disclosure also encompasses a method of inhibiting the undesired firing of a fastening tool. It additionally discloses a method of protecting a nosepiece 12 by using a lockout and equivalents thereof.

FIG. 17A illustrates an embodiment of a contact trip actuator 700. The contact trip actuator 700 can be a plastic compliant member. The contact trip actuator 700 can be used to control the amount of force which is applied to a tactile switch 800. Optionally, the tactile switch 800 can be mounted on a potting boat 1000. The contact trip actuator 700 can serve as a shock absorber and limit the force transmitted when the activation rod 403 contacts a leg face 705. In an embodiment, the activation rod 403 is connected to the upper contact trip 310 and moves in conjunction with the movement of the upper contact trip 310. The movement of the upper contact trip 310 toward the nose plate 331 can move the activation rod 403 to press against the leg face 705 (e.g. FIG. 15I).

Using the contact trip actuator 700 can increase the durability of a fastener tool's trigger mechanism by extending the life of the tactile switch 800. When switched or triggered, the tactile switch 800 can cause the fastening tool to drive a fastener, e.g. a nail. A fastener tool's trigger mechanism can be broadly construed to include all related elements which when triggered, activated or actuated cause a fastener to be driven. The life of the tactile switch 800 can achieve a large number of switching cycles through the use of trip actuator 700. In an embodiment, the use of the contact trip actuator 700 can achieve a life of the tactile switch 800 which is as long, or longer, than the life of the fastening tool in which it is used. A life of the tactile switch 800 can be considered to include in an aspect the total number of switching cycles which can occur before the failure of the tactile switch 800.

In an embodiment, the contact trip actuator 700 can at least in part be composed of a flexible material. In non-limiting example, the flexible material can be an acetal plastic. In an embodiment, an acetal polyoxymethylene (POM) homopolymer and/or copolymer can be used. In example embodiments, the flexible material can have a flexural modulus of 250,000 psi or greater; 420,000 psi or greater; or 600,000 psi or greater (ASTM D-790). In an example embodiment, the flexible material can have a flexural strength of 14,300 psi with a flexural modulus of 420,000 psi (ASTM D-790). In other embodiments, a flexural strength of, e.g. 10,000 psi, 12,500 psi, 15,000 psi, 20,000 psi, 30,000 psi, or greater, can be used, as well as a value of flexural strength from within the ranges of these numbers (e.g. a number between 10,000 psi to 30,000 psi, or subset ranges thereof; ASTM D-790). In an embodiment, the flexible material can have a strength yield of 10,000 psi or greater (ASTM D-368). In an embodiment, the flexible material can have a shear strength of 9,500 psi or greater (ASTM D-732). In an embodiment, the flexible material can have a specific gravity within a range of 1.1 and 3.0, e.g. 1.30, 1.42, 1.5 or 1.75 (ASTM D-792). An embodiment uses a specific gravity of 1.42 (ASTM D-792).

In an embodiment, the contact trip actuator 700 can have a flexible material which can at least in part be composed of Dupont™ Delrin® Acetal Resin (DuPont, BMP26-2363, Lancaster Pike & Route 141, Wilmington, Del. 19805 U.S.A.; common name "polyoxymethylene"). In an embodiment, Delrin® Acetal Resin melt flow series 100 is employed in the contact trip actuator 700. In other embodiments, Delrin® Acetal Resin melt flow series 300, 500 and 900 can be used at least in part to make the contact trip actuator 700. The Dupont™ Delrin® Acetal Resin can be cured when producing the contact trip actuator 700.

In an embodiment, the pressure exerted by the contact trip actuator 700 upon the tactile switch 800 equal to or less than 0.5 Kgf and the life cycle of the switch is 4,500,000 switchings or greater. In other embodiments, the pressure exerted by the contact trip actuator 700 upon the tactile switch 800 equal to or less than 0.3 Kgf and the life cycle of the switch is 800,000 switchings or greater. In other embodiments, the pressure exerted by the contact trip actuator 700 upon the tactile switch 800 equal to or less than 0.22 Kgf and the life cycle of the switch is 1,000,000 switchings or greater. In other embodiments, the pressure exerted by the contact trip actuator 700 upon the tactile switch 800 can be equal to or less than 0.15 Kgf and the life cycle of the switch can be 2,000,000 switchings or greater. In other embodiments, the pressure exerted by the contact trip actuator 700 upon the tactile switch 800 can be equal to or less than 0.10 Kgf and the life cycle of the switch can be 3,000,000 switchings or greater.

In the example embodiment of FIG. 17A, the contact trip actuator 700 can pivot on a potting boat axle 1010. In an embodiment, the potting boat axle 1010 can be an axle molded as a part of the potting boat 1000. In another embodiment, an axle for pivot of the contact trip actuator 700 is not a molded portion of the potting boat, but can be a member connected to the potting boat or elsewhere on the fastening tool.

In the example illustrated in FIG. 17A, the contact trip actuator 700 has an actuator hub 702 from which a contact leg 704 and an actuator spring curl 706 each extend. The actuator hub 702 can be rotationally mounted on a potting boat axle 1010 through a key hole 701 in the actuator hub 702. The actuator spring curl 706 can curve radially about at least a portion of the actuator hub 702. The actuator spring curl 706 can transitions from a curl to extend as an actuator switch contact leg 708 which can terminate with a tactile contact switch pad 710.

In an embodiment, a contact switch pad face 709 can be a distance of less than 5 mm, e.g. 2 mm, from a tactile switch face 805 when in a resting state. In an embodiment, in a resting state a distance S can be less than 3 mm. In another embodiment, in a resting state the distance S can be 2 mm, or less than 2 mm. In yet another embodiment, the S can be zero mm (0 mm), such that the contact switch pad face 709 rests in contact with the tactile switch face 805. In an embodiment, contact switch pad face 709 can be connected to the tactile switch face 805, or a unitary piece.

An application of force by the activation rod 403 to the contact leg face 705 can cause the contact switch pad face 709 to contact the tactile switch face 805. In an embodiment, if 5 N of force applied to the tactile switch face 805 by a contact from the switch pad face 709, then the tactile switch 800 can switch causing a signal which can activate the microprocessor to turn the motor and drive a fastener. In an embodiment, the force exerted upon the tactile switch is normal to the face plane FP of the tactile switch face 805. The amount of force applied by the contact switch pad face 709 to the tactile switch face 805 can widely vary. In an embodiment the force can have a value in a range of 1 N to 20 N. In another embodiment the force applied by the contact switch pad face 709 to the tactile switch face 805 can be a value in a range of 3 N to 8 N, e.g. 4 N or 6 N.

In another embodiment, a force limiting means can be employed which is different from, instead of or in addition to the contact trip actuator 700. Such a different force limiting means can be used at a location in the actuation mechanism between the activation rod 403 and the tactile switch 800. Such a means for force limiting can be or use, but is not limited to, a spring, a rubber shock absorber, a mechanical shock absorber, a liquid shock absorber, a gel shock absorber or a gear mechanism.

As illustrated in FIG. 17A, in an embodiment, a centerline 712 of the actuator switch contact leg 708 can be parallel to centerline 1011. A distance S between the contact switch pad face 709 (FIG. 17B) of the tactile contact switch pad 710 and the switch face 805 can be 10 mm or less. In an embodiment, a distance S can be measured along a centerline 812 of the tactile switch 800. The distance S can be 5 mm or less. In yet another embodiment distance S can be 3 mm or less, or 2 mm or less. The contact switch pad face 709 can also have a temporary contact or permanent contact with the switch face 805, such that the distance S is zero mm (0 mm).

Figure 17B:
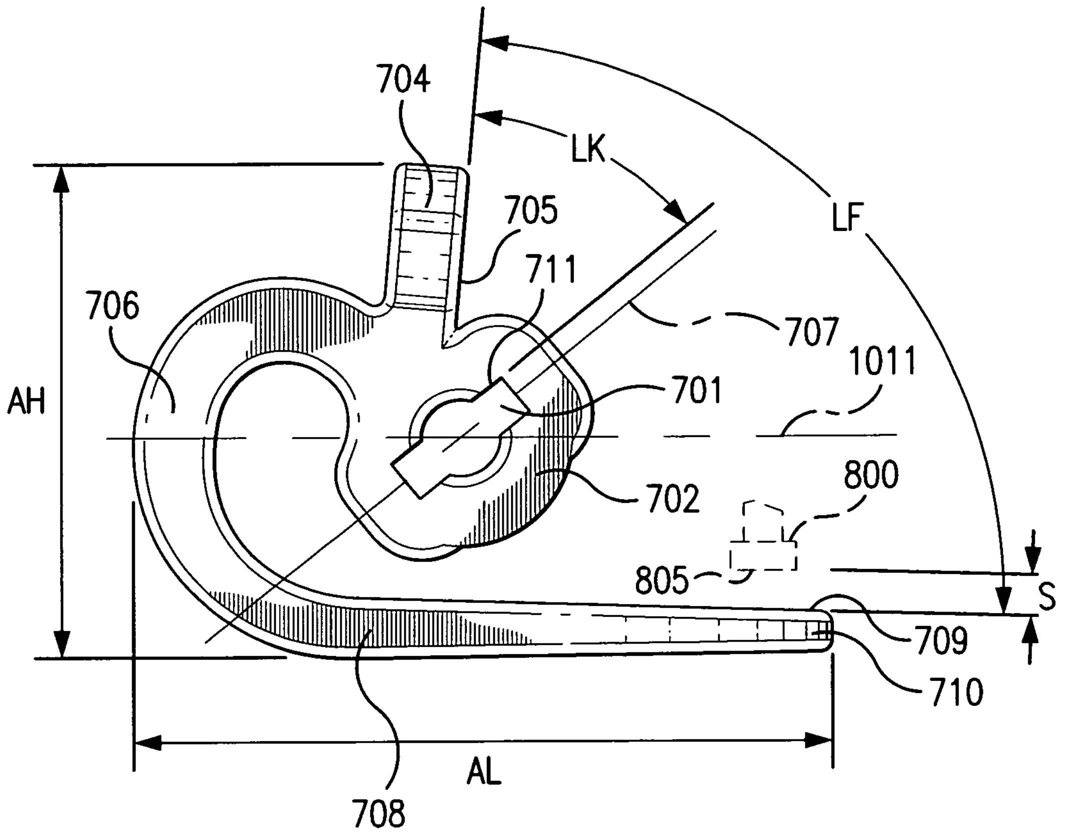
FIG. 17B illustrates an embodiment of angles of a contact trip actuator.

FIG. 17B illustrates embodiments of angles of a contact trip actuator 700. In an example embodiment, an angle LF can be measured from a contact leg face 705 to the contact switch pad face 709 and can have a value of 84°. The angle LF can have a value from a wide range of angles. In non-limiting example, the angle LF a value in a range of from 45° to 165°, or 90°. In an example embodiment, an angle LK can be measured from a contact leg face 705 to a face 711 of a key hole 701 and can have a value of 45°. The Angle LK can have a value from a wide range of angles. In non-limiting example, the angle LK can have a value in a range of from 0° to 180°, or 90°. Like reference numbers in FIG. 17A identify like elements in FIG. 17B.

Additional embodiments can employ additional or different force limiting mechanisms to prolong the life of the tactile switch 800. These include but are not limited to a shock absorbing element or material such as a foam, a cushion, a polymer, a gel, a rubber, a plastic or a spring, which in an embodiment can be in contact with an end of the activation rod 403, or placed elsewhere in the tactile switch 800 actuation mechanism. Alternatively, a shock absorbing element or material such as a foam, a cushion, a polymer, a gel, a rubber, a plastic or a spring can be added in a position such that it absorbs an amount of energy from the activation rod 403 which reduces the amount of force upon the tactile switch 800.

In an embodiment, the contact trip actuator 700 is not used and thus is not present in the actuation mechanism for the tactile switch 800. When the trip actuator 700 is not present, another type of shock absorber can be used to limit the force from the movement of a contract trip and/or nosepiece member and/or the activation rod 403 that can affect the tactile switch 800. Non-limiting examples of such shock absorbers include a foam, a cushion, a polymer, a gel, a rubber, a plastic or a spring.

A means to absorb force and/or mechanical energy affecting the tactile switch 800 can broadly vary and this disclosure broadly encompasses means in this. Additionally, this disclosure encompasses methods for controlling and absorbing force and/or mechanical energy which can affect the tactile switch 800.

Figure 17C:
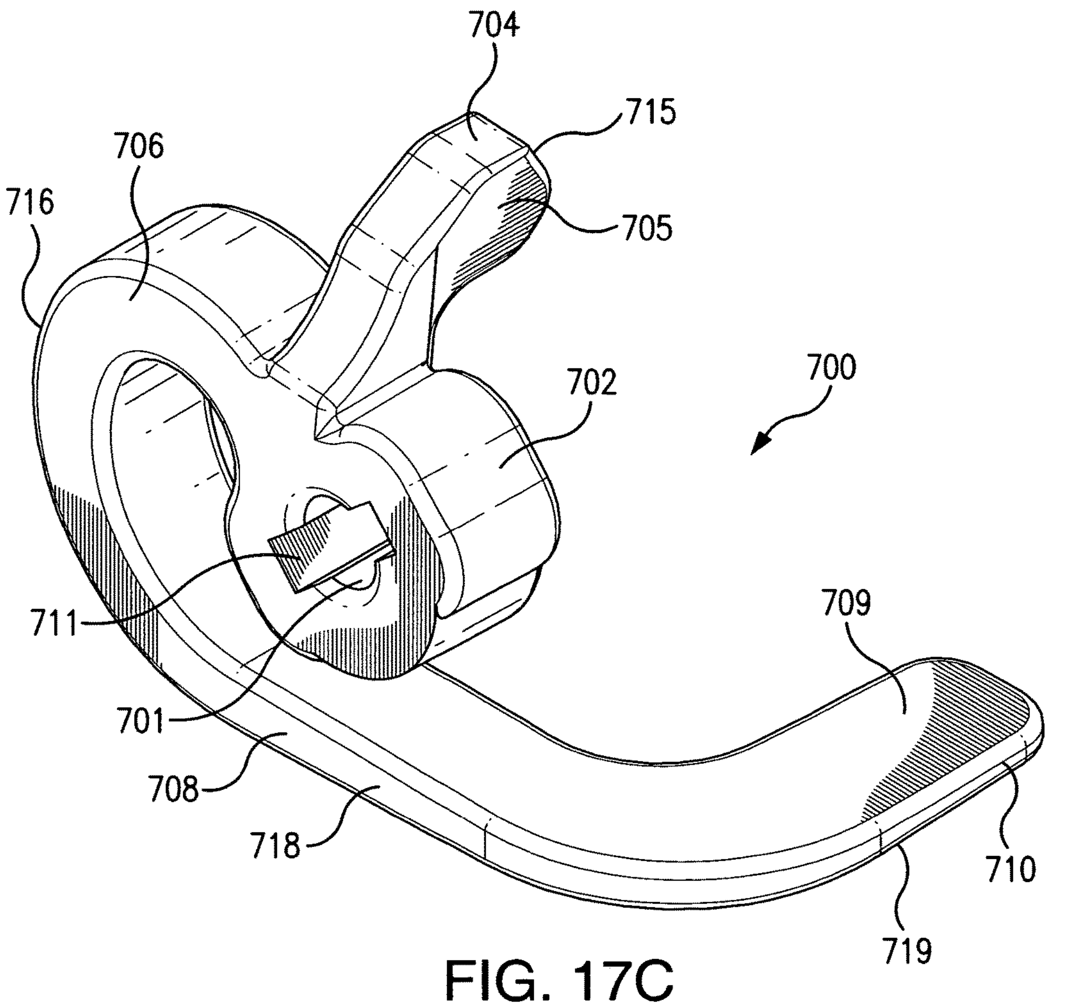
FIG. 17C illustrates a perspective view of a contact trip actuator.

FIG. 17C illustrates a perspective view of a contact trip actuator. FIG. 17C illustrates a contact trip actuator 700 having a switch pad end 719 and a spring curl end 716, as well as a contact leg side 718 and a leg face side 715. Like reference numbers in FIG. 17A identify like elements in FIG. 17C.

Figure 17D:
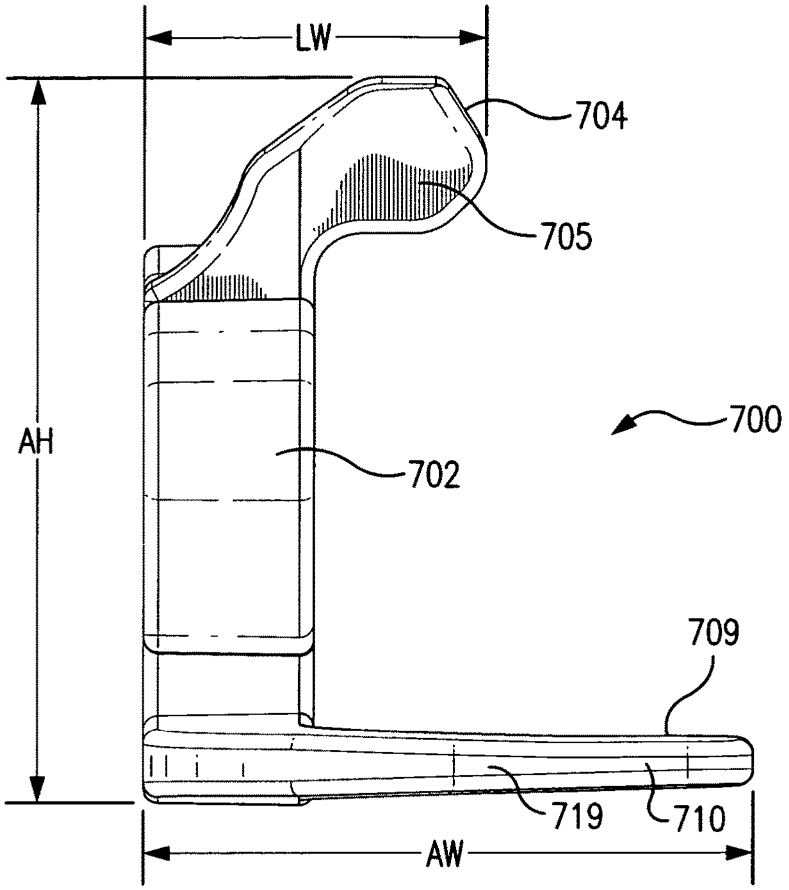
FIG. 17D illustrates a perspective view of a contact trip actuator from the contact switch pad end.

FIG. 17D illustrates a perspective view of a contact trip actuator from the contact switch pad end 719. FIG. 17D illustrates an actuator height AH, an actuator width AW and a contact leg width LW. The design of the contact trip actuator 700 achieves compact dimensions for this part, as well as for the actuation mechanism for the tactile switch 800. The actuator height AH can have a value in a range of 47.88 mm to 11.97 mm, or less. In an embodiment, the actuator height AH can have a value of 23.94 mm. The actuator width AW can have a value in a range of 40.50 mm to 10.13 mm, or less. In an embodiment, the actuator width AW can have a value of 20.25 mm. The contact leg width LW can have a value in a range of 22.80 mm to 5.7 mm, or less. In an embodiment, the contact leg width LW can have a value of 11.40 mm. The dimensions disclosed herein for the actuator height AH, the actuator width AW, the contact leg width LW and the actuator length AL can each have associated with them a tolerance of up to ±3.00 mm, or greater. In an embodiment, the actuator height AH, the actuator width AW, the contact leg width LW and the actuator length AL (FIG. 17E) can each have associated with them a tolerance of up to ±0.20 mm, or greater. Like reference numbers in FIG. 17A and FIG. 17C identify like elements in FIG. 17D.

Figure 17E:
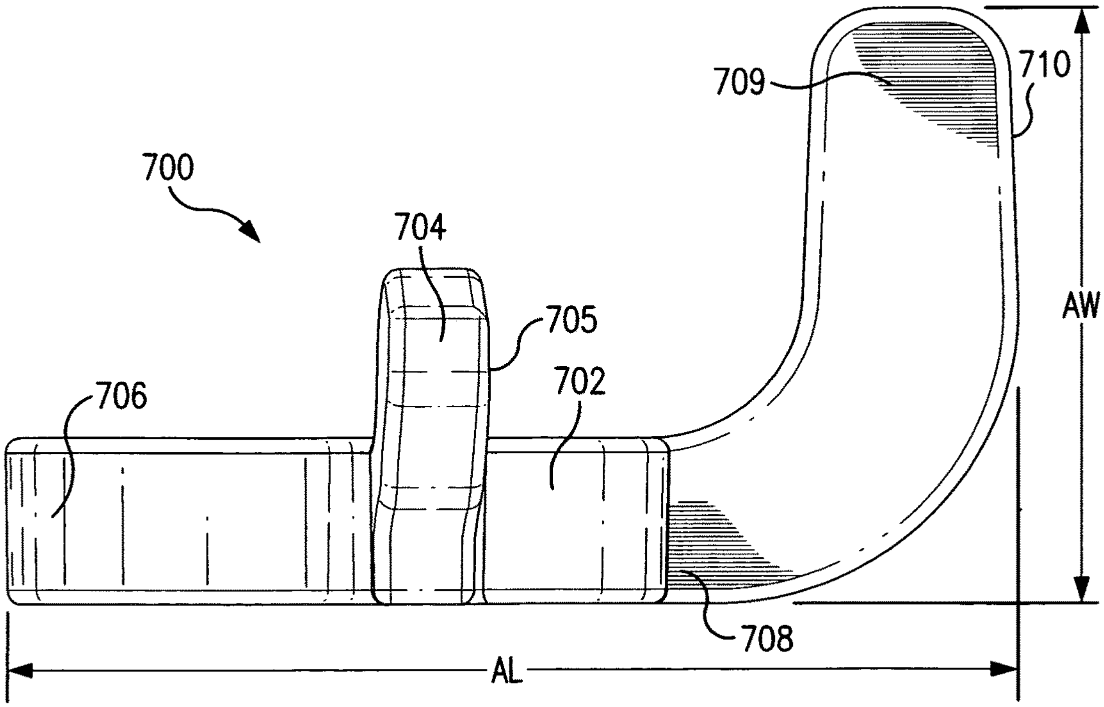
FIG. 17E illustrates a perspective view of a contact trip actuator from a view to the switch pad face.

FIG. 17E illustrates a perspective view of a contact trip actuator viewing the switch pad face 709. FIG. 17E illustrates the actuator width AW and the actuator length AL. As disclosed regarding FIG. 17D, the actuator width AW can have a value in a range of 40.50 mm to 10.13 mm, or less. In an embodiment, the actuator width AW can have a value of 20.25 mm. The actuator length AL can have a value in a range of 64.00 mm to 16.00 mm, or less. In an embodiment, the actuator length AL can have a value of 32.00 mm. Like reference numbers in FIGS. 17A and 17D identify like elements in FIG. 17E.

The dimensions of the contact trip actuator 700 are also referred to herein as follows: the actuator height AH as “AH”; the actuator width AW as “AW”; the contact leg width LW as “LW”: and the actuator length AL as “AL”. In an embodiment the ratio AW:AH:AL:LW can be 1.00:1.18:1.58:0.56. In an embodiment, the ratio of AH:AW can be 1:0.8. In an embodiment, the ratio of AH:AL can be 1:1.3. In an embodiment, the ratio of AL:AW can be 1:0.6. The ratios between each of the respective dimensions AW, AH, AL, and LW disclosed herein can widely vary. Each disclosed value of the ratios disclosed herein regarding AW, AH, AL, and LW can vary in a range of at least up to ±25 percent, or up to ±50 percent.

This disclosure is to be broadly construed to encompass means for controlling forces experience by a contact trip actuator. Additionally, this disclosure encompasses means for actuating the driving of a nail as set forth herein, as well as also without the use of a contact trip actuator. Such means include a broad variety of mechanisms including an actuation element which connects an activation rod 403 or equivalent to a tactile switch 800 or equivalent. The disclosure also encompasses a broad variety of means for absorbing shock in an actuation mechanism for driving a nail.

This disclosure encompasses the methods for controlling the forces experienced by a tactile switch 800 or equivalent, as well as methods to absorb shock within an actuation mechanism. Additionally, This disclosure encompasses the methods for actuating and controlling the actuation of a driving or firing of a fastener by a fastening tool This scope disclosure is to be broadly construed. It is intended that this disclosure disclose equivalents, means, systems and methods to achieve the devices, activities and mechanical actions disclosed herein. For each mechanical element or mechanism disclosed, it is intended that this disclosure also encompass in its disclosure and teaches equivalents, means, systems and methods for practicing the many aspects, mechanisms and devices disclosed herein. Additionally, this disclosure regards a fastening tool and its many aspects, features and elements. Such a tool can be dynamic in its use an operation, this disclosure is intended to encompass the equivalents, means, systems and methods of the use of the tool and its many aspects consistent with the description and spirit of the operations and functions disclosed herein. The claims of this application are likewise to be broadly construed.

The description of the inventions herein in their many embodiments is merely exemplary in nature and, thus, variations that do not depart from the gist of the invention are intended to be within the scope of the invention. Such variations are not to be regarded as a departure from the spirit and scope of the invention.

We claim:

1. A magazine for a fastening device, comprising:

a pusher assembly adapted to have an engaged state and a retracted state, the pusher assembly having a pusher assembly knob and a pusher;

a recess into which the pusher is reversibly retracted at least in part when the pusher assembly knob is moved to reversibly retract the pusher to achieve the retracted state;

a pusher guide track which guides the pusher, the pusher guide track configured to reversibly guide the pusher along at least a portion of a nail track to achieve the retracted state in which the pusher is configured to occupy said recess at least in part; and a detent adapted to reversibly maintain the pusher assembly in the retracted state;

wherein the pusher assembly knob is adapted to reversibly latch to the detent;

wherein the pusher is configured to occupy at least a portion of a nail track when the pusher assembly is in the engaged state, and wherein the pusher has a portion adapted to contact a fastener and to impart a force upon the fastener in a direction toward a nose end of the magazine when the pusher assembly is in the engaged state.

2. The magazine for a fastening device according to claim 1, wherein the detent has a latch portion to which the pusher assembly knob is reversibly latched when the pusher assembly is in the retracted state.

3. The magazine for a fastening device according to claim 1, wherein the detent has a detent base end to which the pusher assembly knob is reversibly latched when the pusher assembly is in the retracted state.

4. The magazine for a fastening device according to claim 1, wherein the detent has a spring latch to which the pusher assembly knob is reversibly latched when the pusher assembly is in the retracted state.

5. The magazine for a fastening device according to claim 1, wherein the pusher assembly comprises a spring located between the pusher assembly knob and the pusher, the spring allowing the pusher assembly knob to be tilted to achieve an unlatched state from a latched state.

6. The magazine for a fastening device according to claim 1, wherein the pusher assembly is free of a compressive spring between the pusher assembly knob and a portion of the pusher.

7. The magazine for a fastening device according to claim 1, wherein the pusher assembly knob can be pivoted to release the pusher assembly knob from the detent to achieve an unlatched state from a latched state.

8. The magazine for a fastening device according to claim 1, wherein the pusher assembly further comprises a pivot about which a pivot stem can move to release the pusher assembly knob from the detent to achieve an unlatched state from a latched state.

9. The magazine for a fastening device according to claim 1, wherein the pusher assembly knob has a knob clearance of 0.05 mm or greater when the pusher assembly is in an engaged state.

10. The magazine for a fastening device according to claim 1, wherein a guide frame comprises the detent.

11. The magazine for a fastening device according to claim 1, wherein the detent is located proximate to a pusher assembly guide path.

12. The magazine for a fastening device according to claim 1, wherein the pusher assembly is biased by a constant force spring.

13. The magazine for a fastening device according to claim 1, in which the fastening tool is a nailer and the fastener is a nail.

14. A fastening device, comprising:

a nosepiece adapted to receive a fastener from a magazine;

a power source adapted to power a fastener driving mechanism to drive the fastener into a workpiece when triggered;

a pusher assembly adapted to have an engaged state and a retracted state, the pusher assembly having a pusher assembly knob and a pusher;

a pusher guide track which guides the pusher along at least a portion of the nail track, the pusher guide track configured to reversibly guide the pusher to achieve the retracted state in which the pusher is configured to occupy said recess at least in part;

a recess into which the pusher is reversibly retracted at least in part when the pusher assembly knob is moved to reversibly retract the pusher to achieve the retracted state;

a detent adapted to reversibly maintain the pusher assembly in the retracted state;

wherein the pusher is configured to occupy at least a portion of a nail track when the pusher assembly is in the engaged state; and wherein the pusher has a portion adapted to contact a fastener and to impart a force upon the fastener in a direction toward the nosepiece when the pusher assembly is in the engaged state.

15. The fastening device according to claim 14, wherein the detent has a latch to which the pusher assembly knob is reversibly latched when the pusher is in the retracted state.

16. The fastening device according to claim 15, wherein the latch comprises a spring latch.

17. The fastening device according to claim 14, wherein the fastening tool is a nailer and the fastener is a nail.

* * * * *